US012728098B2

(12) United States Patent
Bourdeau et al.

(10) Patent No.: US 12,728,098 B2
(45) Date of Patent: Sep. 8, 2026

(54) METHODS OF PRODUCING EXTRACELLULAR VESICLES

(71) Applicant: LONZA SALES AG, Basel (CH)

(72) Inventors: Raymond Bourdeau, Cambridge, MA (US); Su Chul Jang, Cambridge, MA (US); Rane Harrison, Cambridge, MA (US); Conlin O'Neil, Cambridge, MA (US); Aaron Noyes, Cambridge, MA (US)

(73) Assignee: LONZA SALES AG, Basel (CH)

( * ) Notice: Subject to any disclaimer, the term of this patent is extended or adjusted under 35 U.S.C. 154(b) by 1113 days.

(21) Appl. No.: 17/754,174

(22) PCT Filed: Sep. 25, 2020

(86) PCT No.: PCT/US2020/052901
§ 371 (c)(1),
(2) Date: Mar. 25, 2022

(87) PCT Pub. No.: WO2021/062290
PCT Pub. Date: Apr. 1, 2021

(65) Prior Publication Data

US 2023/0103726 A1 Apr. 6, 2023

Related U.S. Application Data

(60) Provisional application No. 63/066,654, filed on Aug. 17, 2020, provisional application No. 63/059,754, filed on Jul. 31, 2020, provisional application No. 62/906,023, filed on Sep. 25, 2019.

(51) Int. Cl.
*A61K 31/7084* (2006.01)
*A61K 9/51* (2006.01)
*B01D 15/38* (2006.01)

(52) U.S. Cl.
CPC .......... *A61K 9/5192* (2013.01); *A61K 9/5176* (2013.01); *A61K 31/7084* (2013.01); *B01D 15/3847* (2013.01)

(58) Field of Classification Search
CPC ............................ B01D 15/3847; C07H 21/02
See application file for complete search history.

(56) References Cited

U.S. PATENT DOCUMENTS

| | | | |
|---|---|---|---|
| 10,195,290 B1 | 2/2019 | Dooley et al. | |
| 2018/0230177 A1* | 8/2018 | Zhong | A61P 31/00 |
| 2019/0202892 A1 | 7/2019 | Lewis et al. | |

FOREIGN PATENT DOCUMENTS

| | | |
|---|---|---|
| WO | 2014/093936 A1 | 6/2014 |
| WO | 2014/179335 A1 | 11/2014 |
| WO | 2014/179760 A1 | 11/2014 |
| WO | 2014/189805 A1 | 11/2014 |
| WO | 2014/189806 A1 | 11/2014 |
| WO | 2015/017652 A1 | 2/2015 |
| WO | 2015/077354 A1 | 5/2015 |
| WO | 2015/185565 A1 | 12/2015 |
| WO | 2016/120305 A1 | 1/2016 |
| WO | 2016/096174 A1 | 6/2016 |
| WO | 2016/096577 A1 | 6/2016 |
| WO | 2016/145102 A1 | 9/2016 |
| WO | 2017/027645 A1 | 2/2017 |
| WO | 2017/027646 A1 | 2/2017 |
| WO | 2017/075477 A1 | 5/2017 |
| WO | 2017/175147 A1 | 10/2017 |
| WO | 2017/175156 A1 | 10/2017 |
| WO | 2018/100558 A2 | 6/2018 |
| WO | 2019/099942 A1 | 5/2019 |
| WO | 2019/133842 A1 | 7/2019 |
| WO | 2020/101740 A1 | 5/2020 |
| WO | 2020/191369 A1 | 9/2020 |

OTHER PUBLICATIONS

Corrales et al., "Direct Activation of STING in the Tumor Microenvironment Leads to Potent and Systemic Tumor Regression and Immunity," Cell Reports 11(7): 1018-1030 (2015).
Corso et al., "Reproducible and scalable purification of extracellular vesicles using combined bind-elute and size exclusion chromatography," Scientific Reports 7(1) (2017).
Dooley et al., "Abstract 2150: engEx: A novel exosome engineering platform enabling targeted transfer of pharmacological molecules," Cancer Res. 79(13_Suppl):2150 (2019).
Dusoswa et al., "Glycan modification of glioblastoma-derived extracellular vesicles enhances receptor-mediated targeting of dendritic cells," J. Extracell. Vesicles 8(1):1648995 (2019).
Hanson et al., "Nanoparticulate STING agonists are potent lymph node-targeted vaccine adjuvants," The Journal of Clinical Investigation 125(6):2532-2546 (2015).
Kleffel et al., "Melanoma Cell-Intrinsic PD-1 Receptor Functions Promote Tumor Growth Cell," Cell 162:1242-1256 (2015).
Klinghoffer et al., "A technology platform to assess multiple cancer agents simultaneously within a patient's tumor," Sci. Transl. Med. 7(284):284ra58 (2015).
Kreiter et al., "Mutant MHC class II epitopes drive therapeutic immune responses to cancer," Nature 520:692-696 (2015).
Kuypers et al., "Survival of rabbit and horse erythrocytes in vivo after changing the fatty acyl composition of their phosphatidylcholine," Biohim Biophys Acta 819(2):170-178 (1985).
Luan et al., "Engineering exosomes as refined biological nanoplatforms for drug delivery," Acta Pharmacol. Sin. 38, 754-763 (2017).

(Continued)

*Primary Examiner* — Jezia Riley

(74) *Attorney, Agent, or Firm* — MEDLER FERRO WOODHOUSE & MILLS PLLC

(57) ABSTRACT

Provided herein are methods of preparing EVs, e.g., exosomes, associated with or encapsulated various cyclic dinucleotides, including STING agonists. Also provided herein are methods of loading EVs, e.g., exosomes, with various cyclic dinucleotides, including STING agonists.

19 Claims, 42 Drawing Sheets

(56) References Cited

OTHER PUBLICATIONS

Mei et al., "Rational design of a fully active, long-acting PEGylated factor VIII for hemophilia A treatment," Blood 116(2):270-79 (2010).
Meric-Bernstam et al., "Phase Ib study of MIW815 (ADU-S100) in combination with spartalizumab (PDR001) in patients (pts) with advanced/metastatic solid tumors or lymphomas," J. Clin. Oncol. 37(15_suppl), 2507 (2019).
Ohkuri et al., "Effects of STING stimulation on macrophages: STING agonists polarize into "classically" or "alternatively" activated macrophages?" Hum. Vaccin. Immunother. 14(2):285-287 (2018).
Ordikhani et al., "Targeting antigen-presenting cells by anti-PD-1 nanoparticles augments antitumor immunity," JCI Insight 3(20):e122700 (2018).
Reiter et al., "Separation of virus-like particles and extracellular vesicles by flow-through and heparin affinity chromatography," Journal of Chromatography A 1588:77-74 (2019).
Shoiw et al., "CD69 acts downstream of interferon-alpha/beta to inhibit S1P1 and lymphocyte egress from lymphoid organs," Nature 440, 540-544 (2006).
Siddiqui et al., "Intratumoral Tcf1+PD-1+CD8+ T Cells with Stem-like Properties Promote Tumor Control in Response to Vaccination and Checkpoint Blockade Immunotherapy," Immunity 50(1):195-211.e10 (2019).
Sivick et al., "Magnitude of Therapeutic STING Activation Determines CD8+ T Cell-Mediated Anti-tumor Immunity," Cell Rep. 25:3074-3085 (2018).
Szabo et al., "A novel transcription factor, T-bet, directs Th1 lineage commitment," Cell 100:655-669 (2000).
Tang et al. "Agonist-Mediated Activation of STING Induces Apoptosis in Malignant B Cells," Cancer Res. 76(8):2137-2152 (2016).
Ugel et al., "Tumor-induced myeloid deviation: when myeloid-derived suppressor cells meet tumor-associated macrophages," J Clin. Invest. 125(9):3365-3376 (2015).
Zhang et al., "Mixed-mode chromatography in pharmaceutical and biopharmaceutical applications," Journal of Pharmaceutical and Biomedical Analysis 128:73-88 (2016).

* cited by examiner

IFNβ (RLU)
CDN (μM)
CDN1
exoCDN1
CDN2
exoCDN2

EC50 IFNβ production (PBMC)
concentration (μM)
****
CDN1
exoCDN1

IFNβ (RLU)
CDN (μM)
CDN1 ①
CDN1 + Exo ②
exoCDN1 ③

Tumor Volume (mm3)
Days
PBS ①
CDN1 20μg ②
CDN1 (0.2 μg) ③
exoCDN1 (0.2 μg) ④

Tumor Volume (mm³)
2500
2000
1500
1000
500
0
6 7 8 9 10 11 12 13 14 15 16 17 18 19 20
Days
PBS ①
CDN2 (20 μg) ②
CDN2 (0.1 μg) ③
CDN2 (0.1 μg) + Exo ④
exoCDN2 (0.1 μg) ⑤
① ② ③ ④ ⑤

PBS ①
CDN2 (20 µg) ②
CDN2 (0.012 µg) ③
exoCDN2 (0.012 µg) ④
exoCDN2 (0.12 µg) ⑤
Tumor Volume (mm³)
2000
1500
1000
500
0
5
6
7
8
9
10
11
12
13
14
15
16
17
18
Days
****

PBS
CDN2 (20 ug)
exoCDN2 (0.12 ug)
ANL
Tumor cells
Immune cells

| Treatment | Complete responses in lungs |
|---|---|
| PBS | 0/8 |
| CDN2 (20 µg) | 1/8 |
| CDN2 (0.012 µg) | 0/7 |
| exoCDN2 (0.012 µg) | 4/8 |
| exoCDN2 (0.12 µg) | 4/8 |

B16F10

Exosomes + IgG ①
Exosomes + Anti-CD8 ②
exoCDN2 (0.1 μg) + IgG ③
exoCDN2 (0.1 μg) + Anti-CD8 ④

Tumor Volume ($mm^3$)
1800
1500
1200
900
600
300
0
7 8 9 10 11 12 13 14 15 16 17
Days CDN2 (30 µg) ①
CDN2 (0.3 µg) ②
exoCDN2 (0.3 µg) ③
CDN2 (nM)
1000000
100000
10000
1000
100
10
0
20
40
60
Time (h)
LLCQ % positive area of IFN-β
15
10
5
0
Exosomes
4h
24h
1 dose
4h
24h
2 doses
CDN2 (20 μg)
4h
24h
1 dose
4h
24h
2 doses
exoCDN2 (0.1 μg)
*
n.s.

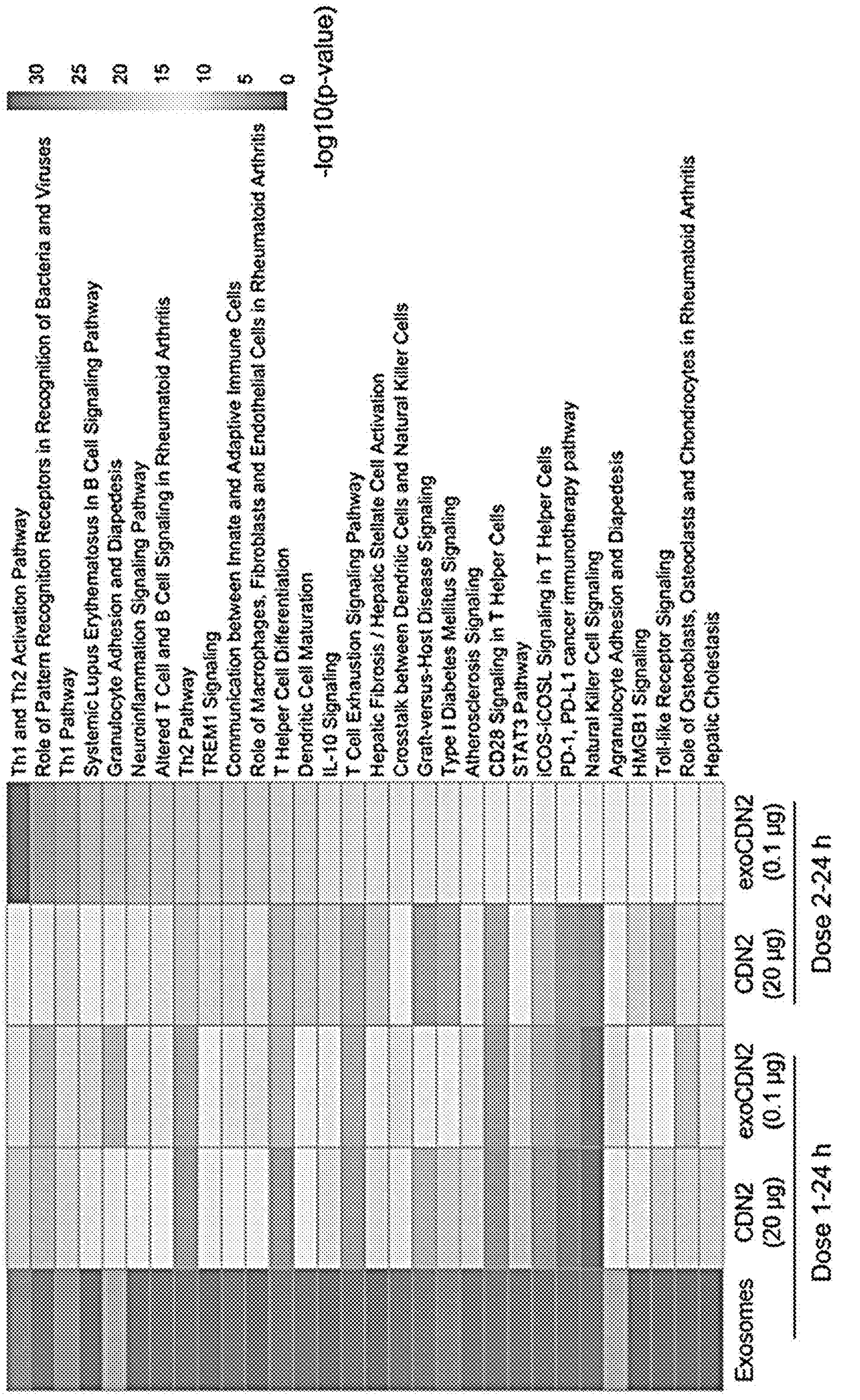

Fig. 16D
Th1 and Th2 Activation Pathway
Role of Pattern Recognition Receptors in Recognition of Bacteria and Viruses
Th1 Pathway
Systemic Lupus Erythematosus In B Cell Signaling Pathway
Granulocyte Adhesion and Diapedesis
Neuroinflammation Signaling Pathway
Altered T Cell and B Cell Signaling in Rheumatoid Arthritis
Th2 Pathway
TREM1 Signaling
Communication between Innate and Adaptive Immune Cells
Role of Macrophages, Fibroblasts and Endothelial Cells in Rheumatoid Arthritis
T Helper Cell Differentiation
Dendritic Cell Maturation
IL-10 Signaling
T Cell Exhaustion Signaling Pathway
Hepatic Fibrosis / Hepatic Stellate Cell Activation
Crosstalk between Dendritic Cells and Natural Killer Cells
Graft-versus-Host Disease Signaling
Type I Diabetes Mellitus Signaling
Atherosclerosis Signaling
CD28 Signaling in T Helper Cells
STAT3 Pathway
iCOS-iCOSL Signaling in T Helper Cells
PD-1, PD-L1 cancer immunotherapy pathway
Natural Killer Cell Signaling
Agranulocyte Adhesion and Diapedesis
HMGB1 Signaling
Toll-like Receptor Signaling
Role of Osteoblasts, Osteoclasts and Chondrocytes in Rheumatoid Arthritis
Hepatic Cholestasis
30
25
20
15
10
5
0
-log10(p-value)
Exosomes
CDN2 (20 μg)
exoCDN2 (0.1 μg)
CDN2 (20 μg)
exoCDN2 (0.1 μg)
Dose 1-24 h
Dose 2-24 h

METHODS OF PRODUCING EXTRACELLULAR VESICLES

CROSS-REFERENCE TO RELATED APPLICATIONS

This application claims priority benefit of U.S. Provisional Application Nos. 62/906,023, filed Sep. 25, 2019; 63/059,754, filed Jul. 31, 2020; and 63/066,654, filed Aug. 17, 2020, each of which is herein incorporated by reference in its entirety.

REFERENCE TO SEQUENCE LISTING SUBMITTED ELECTRONICALLY VIA EFS-WEB

The content of the electronically submitted sequence listing in ASCII text file (Name: 4000_068PC03_Seqlisting_ST25.txt; Size: 31,579 bytes; and Date of Creating: Sep. 24, 2020), filed with the application, is incorporated herein by reference in its entirety.

FIELD OF DISCLOSURE

The present disclosure relates to extracellular vesicles (EVs), e.g., exosomes, comprising a cyclic dinucleotide such as a STING-agonist. The present disclosure also relates to methods of manufacturing the EVs.

BACKGROUND

The innate immune system recognizes pathogen associated molecular patterns (PAMPs) via pattern recognition receptors (PRRs) that induce an immune response. PRRs recognize a variety of pathogen molecules including single and double stranded RNA and DNA. PRRS such as retinoic acid-inducible gene-I (RIG-I)-like receptors (RLRs) and some toll-like receptors (TLRs) recognize RNA ligands. DNA ligands are recognized by cyclic GMP-AMP synthase (cGAS), AIM2 and other TLRs. The TLRs, RLRs, and AIM2 directly interact with other signal cascade adaptor proteins to activate transcription factors, while cGAS produces cGAMP, a cyclic dinucleotide molecule that activates the stimulator of interferon gene (STING) receptor. Both STING and the RLRs activate the adaptor kinase TBK1 which induces activation of transcription factors IRF3, and NF-κB, and result in the production of type I IFNs and pro-inflammatory cytokines. Cyclic dinucleotides (CDNs) were first identified as bacterial signaling molecules characterized by two 3', 5' phosphodiester bonds, such as in the molecule c-di-GMP. While STING can be activated by bacterial CDNs, the innate immune response in mammalian cells is also mediated by the CDN signaling molecule cGAMP which is produced by cGAS. cGAMP is characterized by a mixed 2', 5' and 3', 5' phosphodiester linkage. Both bacterial and mammalian CDNs directly interact with STING to induce the pro-inflammatory signaling cascade that results in the production of type I IFNs, such as IFNα and IFN-β. Stimulator of Interferon Genes (STING) is a cytosolic sensor of cyclic dinucleotides that is typically produced by bacteria. Upon activation, it leads to the production of type I interferons and initiates an immune response. Agonism of STING has been shown as a promising approach for generating an immune response against tumors pre-clinically. Unfortunately, given the broad expression profile of STING, systemic delivery of STING agonists leads to systemic inflammation. This limits the dose that can be given which in turn limits the therapeutic efficacy. An alternative approach to systemic delivery is to inject the STING agonist directly into the tumor. Intra-tumoral injections are quite effective; however, they are limited to solid tumors that can be reached with a needle and lead to tissue damage. Improved methods of delivering STING agonists are therefore needed.

SUMMARY OF THE DISCLOSURE

In some aspects, the disclosure is related to a method of preparing a composition comprising extracellular vesicles (EVs) associated with one or more cyclic dinucleotides (CDNs), comprising incubating the EVs with a loading concentration of cyclic dinucleotides (CDNs) in a mixture, wherein, after the incubation, the composition comprises EVs with loaded CDNs and free CDNs and wherein the free CDNs are removed by a multimodal chromatography. In some aspects, the EVs have potency higher than reference EVs (EVs that are loaded with 5 μM and did not go through the multimodal chromatography). In some aspects, the composition after the chromatography comprises CDNs at a final concentration between 1 μM and 10 μM. In some aspects, the composition after the chromatography comprises CDNs at a concentration between about 2 μM and about 10 μM, between about 2 μM and about 9 μM, between about 3 μM and about 9 μM, between about 3 μM and about 8 μM, between about 4 μM and about 8 μM, between about 4 μM and about 7 μM, between about 4 μM and about 6 μM, between about 4 μM and 5 μM, or between about 5 μM and 6 μM. In some aspects, the composition after the chromatography comprises CDNs at a concentration of about 4 μM, about 5 μM, about 6 μM, or about 7 μM. In some aspects, the loading concentration of the CDNs is at least about 500 μM, at least about 600 μM, at least about 700 μM, at least about 800 μM, at least about 900 μM, at least about 1000 μM, at least about 1100 μM, at least about 1200 μM, at least about 1300 μM, at least about 1400 μM, at least about 1500, at least about 1600 μM, at least about 1700 μM, at least about 1800 μM, at least about 1900 μM, or at least about 2000 μM. In some aspects, the loading concentration of the CDNs is between about 700 μM and about 2 mM, between about 700 μM and about 1.9 mM, between about 700 μM and about 1.8 mM, between about 700 μM and about 1.7 mM, between about 700 μM and about 1.6 mM, between about 700 μM and about 1.5 mM, between about 700 μM and about 1.4 mM, between about 700 μM and about 1.3 mM, between about 700 μM and about 1.2 mM, between about 700 μM and about 1.1 mM, between about 700 μM and about 1 mM, between about 800 μM and about 2 mM, between about 800 μM and about 1.9 mM, between about 800 μM and about 1.8 mM, between about 800 μM and about 1.7 mM, between about 800 μM and about 1.6 mM, between about 800 μM and about 1.5 mM, between about 800 μM and about 1.4 mM, between about 800 μM and about 1.3 mM, between about 800 μM and about 1.2 mM, between about 800 μM and about 1.1 mM, between about 800 μM and about 1 mM, between about 900 μM and about 2 mM, between about 900 μM and about 1.9 mM, between about 900 μM and about 1.8 mM, between about 900 μM and about 1.7 mM, between about 900 μM and about 1.6 mM, between about 900 μM and about 1.5 mM, between about 900 μM and about 1.4 mM, between about 900 μM and about 1.3 mM, between about 900 μM and about 1.2 mM, between about 900 μM and about 1.1 mM, or between about 900 μM and about 1 mM. In some aspects, the loading concentration of the CDNs is about 900 μM, about 1000 μM, about 1100 μM, about 1200 μM, about 1300 μM, about 1400 μM, or about 1500 μM.

In some aspects, after the multimodal chromatography, the percentage of free CDNs present in the composition is less than about 1 percent, less than about 5 percent, less than about 10 percent, less than about 15 percent, less than about 20 percent, less than about 25 percent, less than about 30 percent, less than about 35 percent, less than about 40 percent, less than about 45 percent, less than about 50 percent, less than about 55 percent, less than about 60 percent, less than about 65 percent, less than about 70 percent, less than about 75 percent, less than about 80 percent, less than about 85 percent, less than about 90 percent, or less than about 55 percent. In some aspects, after the incubation, the percentage of EVs loaded with a CDN is about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 75%, about 70%, about 65%, about 60%, about 55%, about 50%, about 45%, about 40%, about 35%, about 30%, about 25%, about 20%, or about 10%.

In some aspects, the present disclosure is related to a method of improving potency of cyclic dinucleotides (CDNs) in association with an EV, comprising: incubating the EV with the CDNs at a loading concentration of at least about 0.5 mM in a composition, wherein the composition, after the incubation, comprises the EVs with loaded CDNs and free CDNs, and removing the free CDNs from the EVs, wherein after the separation, the loaded CDNs are at a concentration between about 0.5 μM and about 10 μM. In some aspects, the loading concentration of CDNs is between about 700 μM and about 2 mM, between about 700 μM and about 1.9 mM, between about 700 μM and about 1.8 mM, between about 700 μM and about 1.7 mM, between about 700 μM and about 1.6 mM, between about 700 μM and about 1.5 mM, between about 700 μM and about 1.4 mM, between about 700 μM and about 1.3 mM, between about 700 μM and about 1.2 mM, between about 700 μM and about 1.1 mM, between about 700 μM and about 1 mM, between about 800 μM and about 2 mM, between about 800 μM and about 1.9 mM, between about 800 μM and about 1.8 mM, between about 800 μM and about 1.7 mM, between about 800 μM and about 1.6 mM, between about 800 μM and about 1.5 mM, between about 800 μM and about 1.4 mM, between about 800 μM and about 1.3 mM, between about 800 μM and about 1.2 mM, between about 800 μM and about 1.1 mM, between about 800 μM and about 1 mM, between about 900 μM and about 2 mM, between about 900 μM and about 1.9 mM, between about 900 μM and about 1.8 mM, between about 900 μM and about 1.7 mM, between about 900 μM and about 1.6 mM, between about 900 μM and about 1.5 mM, between about 900 μM and about 1.4 mM, between about 900 μM and about 1.3 mM, between about 900 μM and about 1.2 mM, between about 900 μM and about 1.1 mM, or between about 900 μM and about 1 mM. In some aspects, the concentration of the loaded CDNs is between about 4 μM and about 7 μM. In some aspects, the final concentration after the chromatography is between about 2 μM and about 10 μM, between about 2 μM and about 9 μM, between about 3 μM and about 9 μM, between about 3 μM and about 8 μM, between about 4 μM and about 8 μM, between about 4 μM and about 7 μM, between about 4 μM and about 6 μM, between about 4 μM and about 5 μM, or between about 5 μM and about 6 μM. In some aspects, the final concentration after the chromatography is about 4 μM, about 5 μM, about 6 μM, or about 7 μM. In some aspects, the loading concentration of the EVs is at least about $2\times10^{12}$ particles/mL, at least about $2.5\times10^{12}$ particles/mL, at least about $3\times10^{12}$ particles/mL, at least about $3.50\times10^{12}$ particles/mL, at least about $4\times10^{12}$ particles/mL, at least about $4.5\times10^{12}$ particles/mL, at least about $5\times10^{12}$ particles/mL, at least about $5.50\times10^{12}$ particles/mL, at least about $6\times10^{12}$ particles/mL, at least about $6.50\times10^{12}$ particles/mL, at least about $7\times10^{12}$ particles/mL, at least about $7.5\times10^{12}$ particles/mL, at least about $8\times10^{12}$ particles/mL, or at least about $8.5\times10^{12}$ particles/mL. In some aspects, the loading concentration of the EVs is between about $3\times10^{12}$ particles/mL and about $9\times10^{12}$ particles/mL, between about $3.5\times10^{12}$ particles/mL and about $9\times10^{12}$ particles/mL, between about $4\times10^{12}$ particles/mL and about $9\times10^{12}$ particles/mL, between about $4.5\times10^{12}$ particles/mL and about $9\times10^{12}$ particles/mL, between about $5\times10^{12}$ particles/mL and about $9\times10^{12}$ particles/mL, between about $5.5\times10^{12}$ particles/mL and about $9\times10^{12}$ particles/mL, or between about $5.5\times10^{12}$ particles/mL and about $8.5\times10^{12}$ particles/mL. In some aspects, the loading concentration of CDNs is between 0.9 mM and 1.1 mM. In some aspects, the loading concentration of the EVs is between about $2\times10^{12}$ particles/mL and about $8\times10^{12}$ particles/mL, between about $2.5\times10^{12}$ particles/mL and about $7.5\times10^{12}$ particles/mL, between about $2.5\times10^{12}$ particles/mL and about $7\times10^{12}$ particles/mL, between about $2.5\times10^{12}$ particles/mL and about $6.5\times10^{12}$ particles/mL, between about $3\times10^{12}$ particles/mL and about $7.5\times10^{12}$ particles/mL, between about $3\times10^{12}$ particles/mL and about $7\times10^{12}$ particles/mL, between about $3\times10^{12}$ particles/mL and about $6.5\times10^{12}$ particles/mL, between about $3.5\times10^{12}$ particles/mL and about $7.5\times10^{12}$ particles/mL, between about $3.5\times10^{12}$ particles/mL and about $7\times10^{12}$ particles/mL, or between about $3.5\times10^{12}$ particles/mL and about $6.5\times10^{12}$ particles/mL. In some aspects, the loading concentration of CDNs is between 0.9 mM and 1.1 mM. In some aspects, after the incubation of the EV with the CDN, the percentage of EVs loaded with a CDN about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 75%, about 70%, about 65%, about 60%, about 55%, about 50%, about 45%, about 40%, about 35%, about 30%, about 25%, about 20%, or about 10%.

In some aspects, the free CDNs are separated from the EVs by a chromatography. In some aspects, the chromatography is a multimodal chromatography. In some aspects, the multimodal chromatography is a CaptoCore 700, Capto MMC, or Capto MMC ImpRes. In some aspects, the multimodal chromatography is a CaptoCore 700. In some aspects, after the chromatography, the percentage of free CDNs present in the composition is less than about 1 percent, less than about 5 percent, less than about 10 percent, less than about 15 percent, less than about 20 percent, less than about 25 percent, less than about 30 percent, less than about 35 percent, less than about 40 percent, less than about 45 percent, less than about 50 percent, less than about 55 percent, less than about 60 percent, less than about 65 percent, less than about 70 percent, less than about 75 percent, less than about 80 percent, less than about 85 percent, less than about 90 percent, or less than about 55 percent.

The present disclosure is also related to a method of removing free cyclic purine dinucleotides (CDNs) in a mixture of EVs and free CDNs, comprising separating the EVs from the free CDNs at a pH lower than 7.6 in a multimodal chromatography. In some aspects, the removing the free CDNs is at a pH lower than about 7.5, about 7.4, about 7.3 about 7.2, about 7.1, about 7.0, about 6.9, or about 6.8. In some aspects, the removing the free CDNs is at a pH lower than about 7.2. In some aspects, the pH is about 6.8. In some aspects, the removal of free CDNs is improved as compared to a reference separation wherein the pH is lower than the reference separation, and the multimodal chromatography comprises an anion-exchange functional group. In some aspects, after the multimodal chromatography, the percentage of free CDNs present in the mixture is less than about 1 percent, less than about 5 percent, less than about 10 percent, less than about 15 percent, less than about 20 percent, less than about 25 percent, less than about 30 percent, less than about 35 percent, less than about 40 percent, less than about 45 percent, less than about 50 percent, less than about 55 percent, less than about 60 percent, less than about 65 percent, less than about 70 percent, less than about 75 percent, less than about 80 percent, less than about 85 percent, less than about 90 percent, or less than about 55 percent.

In some aspects, the lower pH improves the retention of free CDNs on the column as compared to a reference separation. In some aspects, the EV comprises a scaffold protein. In some aspects, the scaffold protein is a type I transmembrane protein or a type II transmembrane protein. In some aspects, the scaffold protein is prostaglandin F2 receptor negative regulator (the PTGFRN protein) or a fragment thereof. In some aspects, the scaffold protein is not associated with the one or more CDNs. In some aspects, the mixture comprises a buffer. In some aspects, the buffer is phosphate, phosphate-buffered saline, citrate, formate, acetate, or Tris (hydroxymethyl)-aminomethane ("Tris") buffer. In some aspects, the EVs are exosomes. In some aspects, the cyclic dinucleotide (CDN) is a STING agonist. In some aspects, the STING agonist is physically and/or chemically modified. In some aspects, the EVs overexpress a PTGFRN protein. In some aspects, the EVs express the PTGFRN protein at least about 100 fold, at least about 110 fold, at least about 120 fold, at least about 130 fold, at least about 140 fold, at least about 150 fold, at least about 160 fold, at least about 170 fold, at least about 180 fold, at least about 190 fold, or at least about 200 fold. In some aspects, the modified STING agonist has a polarity and/or a charge different from the corresponding unmodified STING agonist. In some aspects, the STING agonist comprises:

Formula 1

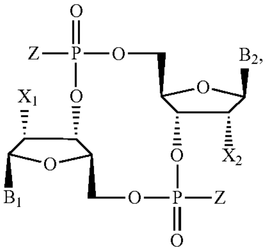

-continued

Formula 2

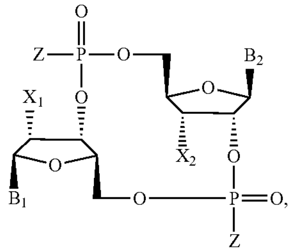

or

Formula 3

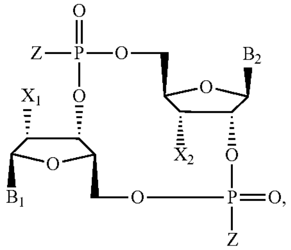

wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

Bi and B2 are bases chosen from:

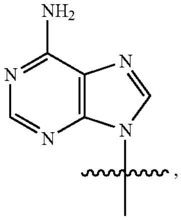

Adenine

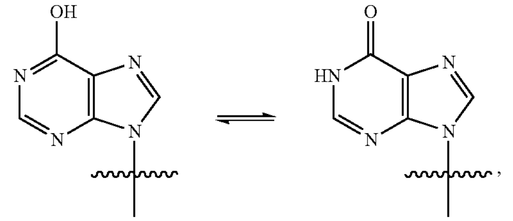

or

Hypoxanthine

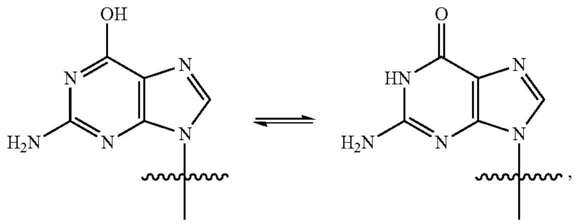

Guanine

With the proviso that:

in Formula (I): $X_1$ and $X_2$ are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH, or a pharmaceutically acceptable salt thereof.

In some aspects, the STING agonist is selected from the group consisting of:

CL606

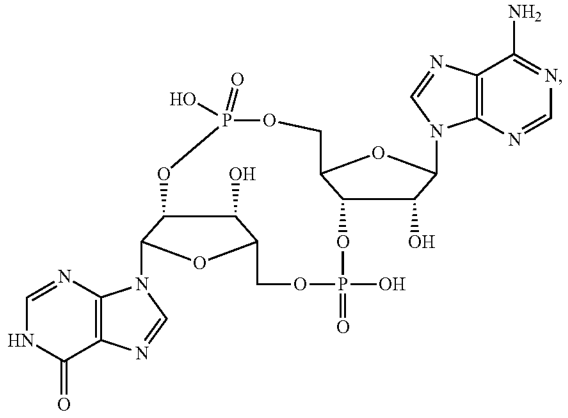

(3′,2′)c-AIMP

CL611

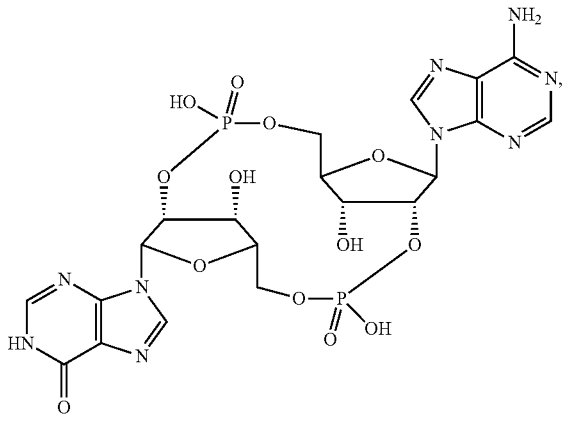

(2′,2′)c-AIMP

-continued

CL602

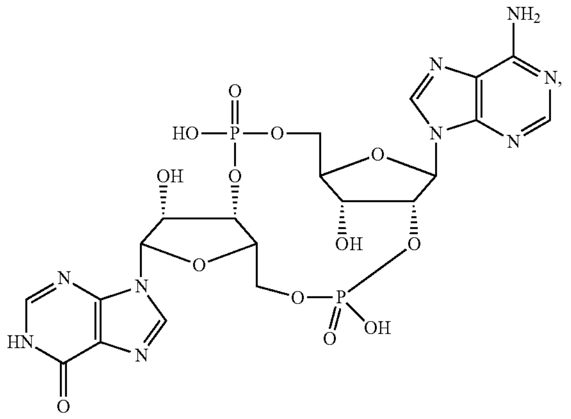

(2′,3′)c-AIMP

CL655

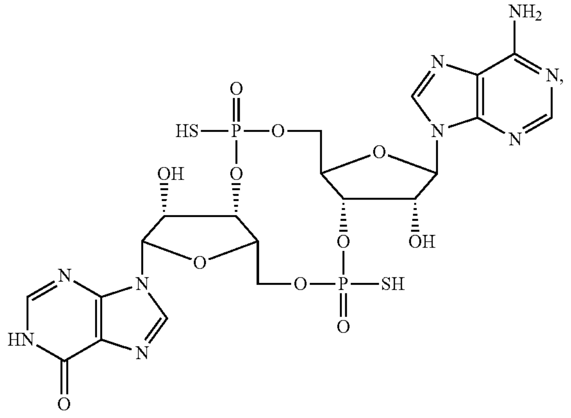

c-AIMP(S)

CL604

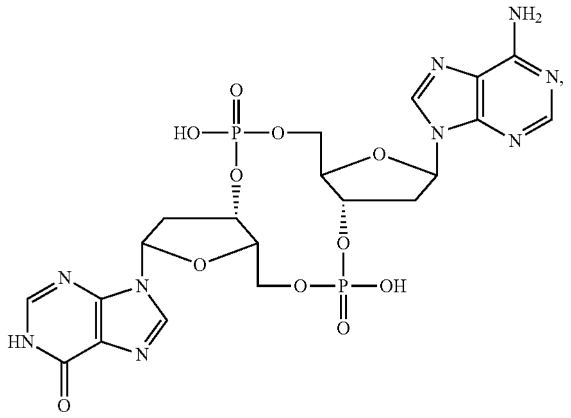

c-(dAMP-dIMP)

-continued
CL609
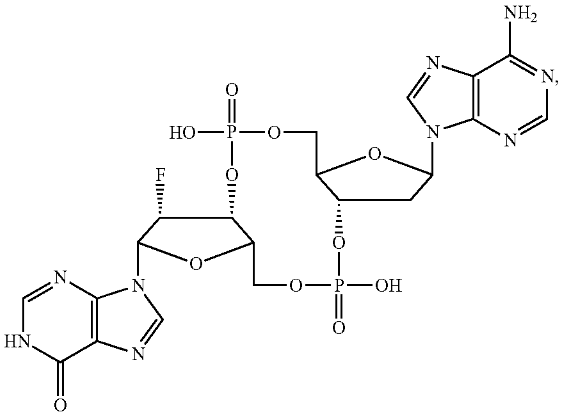
c-(dAMP-2′FdIMP)
CL614
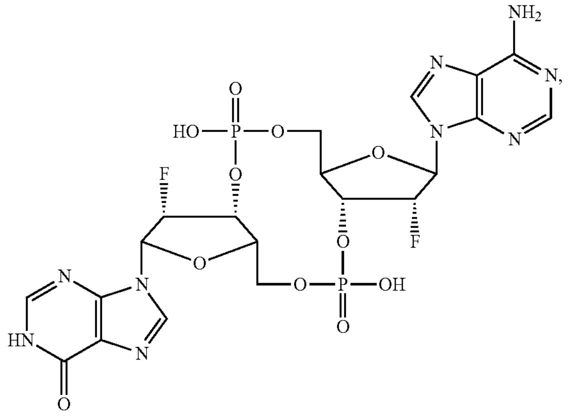
c-(2-FdAMP-2′FdIMP)
CL656
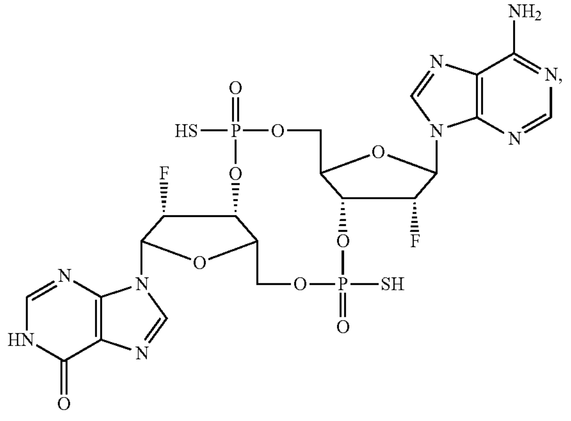
c-[2′-FdAMP(S)-2′FdIMP(S)]
-continued
CL647
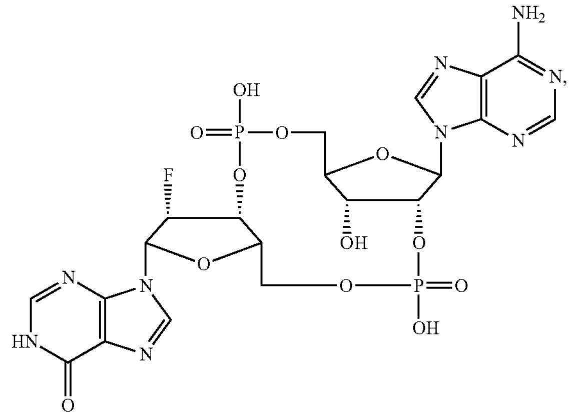
(2′,3′)c-(AMP-2′FdIMP)
CL626
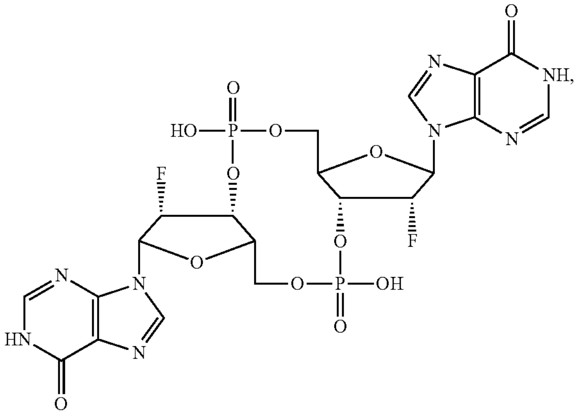
c-di(2′-FdIMP)
CL629
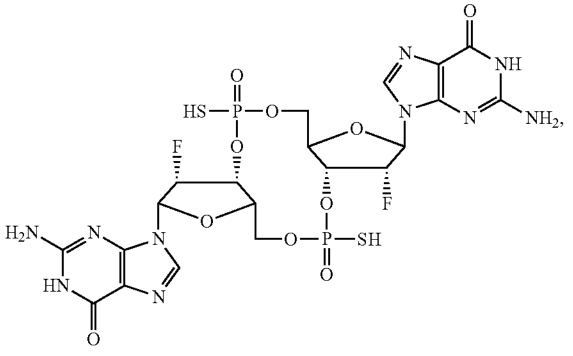
c-di(2′-FdGMP)

-continued

CL603

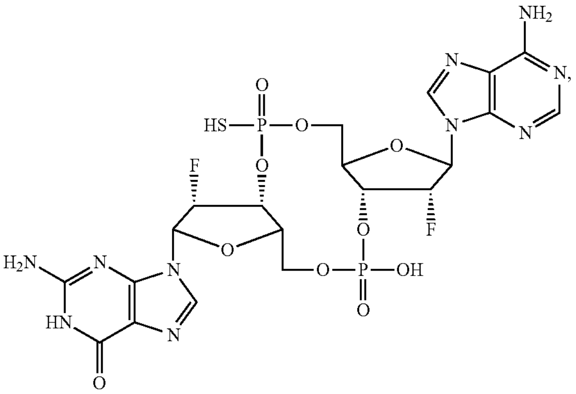

c-(2′-FdGMP-2′FdAMP)

CL632

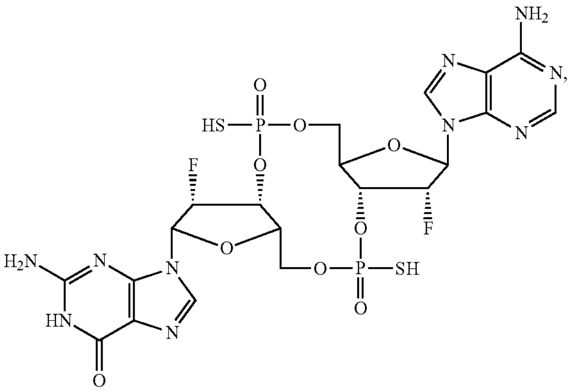

c-[2′FdGMP(S)-2′FdAMP(S)]

CL633

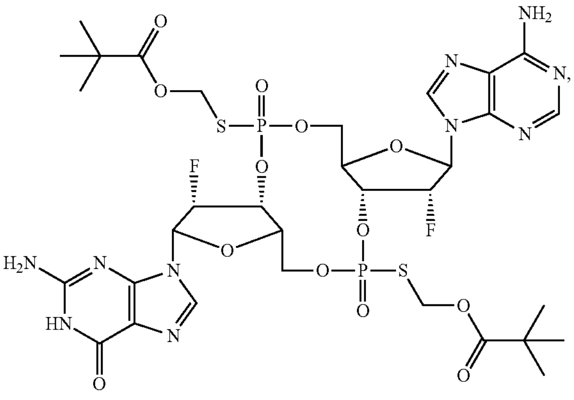

c-[2′FdGMP(S)-2′FdAMP(S)](POM)$_2$

-continued

CL659

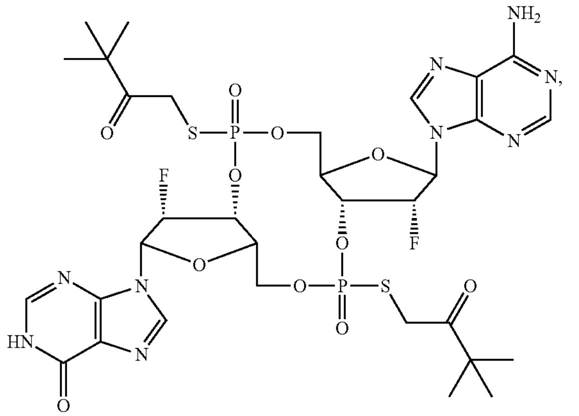

c-[2′FdGMP(S)-2′FdIMP(S)](POM)$_2$ and a pharmaceutically acceptable salt thereof.

In some aspects, the STING agonist is:

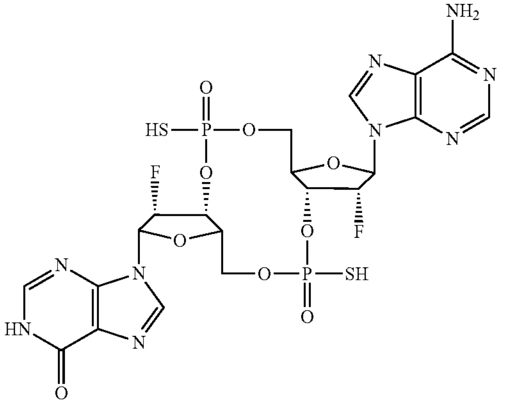

CL656
c-[2'FdAMP(S)-2'FdIMP(S)]

In some aspects, the STING agonist is:

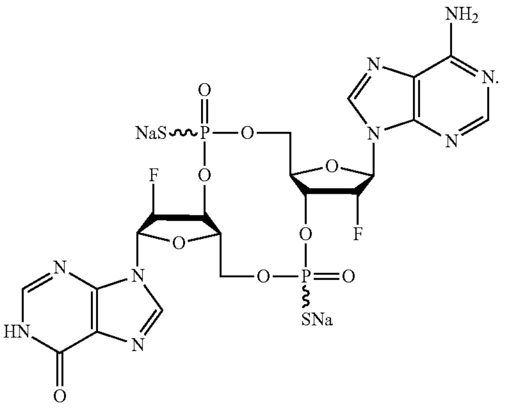

In some aspects, the EVs are formulated in a pharmaceutical composition. In some aspects, the pharmaceutical composition comprises at least about 1 μM, at least about 2 μM, at least about 3 μM, at least about 4 μM, at least about 5 μM, at least about 6 μM, at least about 7 μM, at least about 8 μM, at least about 9 μM, or at least about 10 μM of CDNs. In some aspects, the pharmaceutical composition comprises at least about 5 μM. In some aspects, the pharmaceutical composition is more potent than a reference composition comprising EVs and the same concentration of CDNs, wherein the reference composition is not subjected to a clean-up process to remove free CDNs. In some aspects, the reference composition is incubated in a mixture at a reference CDN concentration at a desired reference composition final cyclic dinucleotide concentration. In some aspects, the pharmaceutical composition comprises a monosaccharide, a disaccharide, a trisaccharide, an oligosaccharide, a polysaccharide, a sugar alcohol, or any combination thereof. In some aspects, the saccharide comprises lactose, glucose, sucrose, trehalose, dextrose, and/or combinations thereof. In some aspects, the saccharide is a sucrose or trehalose. In some aspects, the pharmaceutical composition has improved stability compared to a reference composition comprising a sucrose or trehalose. In some aspects, the saccharide is present in the composition at a concentration of from about 5% w/w to about 10% w/w. In some aspects, the saccharide is present in the composition at a concentration of about 5% w/w. In some aspects, the sugar alcohol comprises glycerol, sorbitol, mannitol, xylitol, and/or combinations thereof. In some aspects, the pharmaceutical composition further comprises sodium chloride. In some aspects, the pharmaceutical composition comprises sodium chloride at a concentration of from about 1 mM to about 100 mM. In some aspects, the sodium chloride is at a concentration of about 1 mM, about 10 mM, about 20 mM, about 30 mM, about 40 mM, about 50 mM, about 60 mM, about 70 mM, about 80 mM, about 90 mM, or about 100 mM. In some aspects, the pharmaceutical composition is further diluted into a buffer and remains potent as compared to a reference composition comprising EVs and the same amount of CDNs, wherein the pharmaceutical composition was not subjected to a clean-up process. In some aspects, the buffer is phosphate-buffered saline, phosphate, citrate, formate, acetate, or Tris (hydroxymethyl)-aminomethane ("Tris") buffer. In some aspects, the buffer is phosphate-buffered saline. In some aspects, the pharmaceutical composition further comprises an anti-oxidant. In some aspects, the anti-oxidant is selected from the group consisting of methionine, L-methionine, ascorbic acid, erythorbic acid, Na ascorbate, thioglycerol, cysteine, acetylcysteine, cystine, dithioerythreitol, dithiothreitol, glutathione, tocopherols, butylated hydroxyanisole (BHA), butylated hydroxytoluene (BHT), and sodium thiosulfate. In some aspects, the antioxidant is L-Methionine. In some aspects, the composition has reduced aggregation as compared to a reference composition comprising EVs and the same amount of CDNs, wherein the pharmaceutical composition was not subjected to a clean-up process. In some aspects, the composition is not lyophilized.

BRIEF DESCRIPTION OF THE DRAWINGS

FIGS. 10A and 10B show IFN-β and CXCL9 an expression response and upregulation in response to various combinations of exosome and STING agonist incubations. The 3 mM, 2 mM, 1 mM, and 1 mM Spike columns represent the concentration of STING agonist (CP-201) used during the incubation with exosomes. 1 mM Spike represents a 1 mM incubation plus an additional 40 uM addition of free STING agonist (CP-201) to the mixture. The data points (8E12/ml, 4E12 ml, 2E12/ml and 1E12/ml) represent the concentration of exosome particles incubated with the various concentrations of CP-201. Final concentrations after chromatography cleanup varied, and therefore in order to normalize a dose of 200 ng of CP-201 per mouse, various volumes from each sample were used and are detailed in the Exosomes per mouse ($\times 10^{10}$) and injection volume of the sample (μL). In order to normalize delivery volume, the final injection volume was adjusted to 200 μL before injection. FIGS. 10C and 10D show the IFN-β and CXCL9 response using two test samples. Sample 1 had an EV count of 1.2E12/mL, a STING agonist (CP-201) concentration of 0.74 g/L, and an injection volume of 10 μL. Sample 2 had an EV count of 8E12/mL, a STING agonist (CP-201) concentration of 1.48 g/L, and an injection volume of 13.2 μL. 20 ng of CP-201 was delivered per mouse, and the final injection volume was adjusted to 200 μL before injection.

FIG. 12A shows representative dose-response curves of IFN-β production in human PMBC supernatant after treating with two different CDN-loaded exosomes, exoCDN1 and exoCDN2, comparing with free CDNs. FIG. 12B shows $EC_{50}$ value of IFN-β production in human PBMC after treating with free CDN1 and exoCDN1 (n=12 healthy donors). FIG. 12C shows representative dose-response curves of IFN-β production in PBMC after treating with free CDN1, free CDN1 with exosomes, and exoCDN1. **, P<0.0001 by unpaired t-test. C57BL/6 mice were implanted subcutaneously with $1\times10^6$ B16F10 cell on right flank of mice. Additional implantation of tumors is specified in each legend. When tumor volumes reached 50-100 $mm^3$, testing agents were injected intratumorally 3 times with 3 days interval. Red arrows in the graph indicate IT injection days. Tumor growth were measured over time. n=5 per group. CDN1: MR SS-2 CDA, CDN2: cAIM(PS)2 Difluor (Rp/Sp). RLU: Relative Luminescent Unit. , P<0.0001 by two-way ANOVA with Tukey's multiple comparison test for tumor growth studies. Data are presented as means±s.e.m. (FIGS. 12D-12**F).

FIG. 13A shows tumor growth curves of subcutaneous tumors. FIG. 13B provides representative H&E stained images from PBS, CDN2 (20 μg), and exoCDN2 (0.12 μg) treated samples. FIG. 13C is a table showing the number of complete responders by histopathological analysis. FIG. 13D is a graphical representation of injected and contralateral (control) tumor growth following intratumoral injection with PBS, empty exosomes, CDN1 (100 μg), or exoCDN2 (0.2 μg). FIG. 13E is a graphical representation of tumor growth following treatment with PBS (n=5), empty exosomes (n=5), CDN1 (100 μg) (n=10), and exoCDN2 (0.2 μg) (n=15) of B16F10 cells ($1\times10^6$ cells) implanted mice that had CR and naïve mice (n=5) on day 50. FIG. 13F is a graphical representation of tumor growth after CD8 T cell depletion in B16F10 tumor bearing mice following administration of the IgG (10 mg/kg) or anti-CD8 antibody (10 mg/kg) intraperitoneally, one day before IT injection (n=5 per group). Blue arrows indicate intraperitoneal injection days (FIG. 13F). FIG. 13G is a bar graph illustrating tumor specific IFN-γ response after PBS, CDN1 (0.2 or 20 μg), and exoCDN1 (0.2 μg) treatment to B16F10 tumor. *, P<0.05; , P<0.01; *, P<0.001; **, P<0.0001 by one-way ANOVA for (FIG. 13**G) and two-way ANOVA with Tukey's multiple comparison test for tumor growth studies. Data are presented as means±s.e.m.

FIGS. 14A and 15B are graphical representations showing the concentration of CDN2 in tumors (FIG. 14A) and plasma (FIG. 14B) as measured by LC-MS/MS at 5 minutes, 30 minutes, 2 hours, 6 hours, 24 hours, and 48 hours after single IT injection (n=3 per group at each time point) in C57BL/6 mice implanted subcutaneously with $1\times10^6$ B16F10 cells. FIGS. 14C-14E are graphs showing the relative expression of IFN-β (FIG. 14C), CXCL9 (FIG. 14D), and CXCL10 (FIG. 14E) genes as measured by RT-qPCR, normalized against the housekeeping gene RPS13. FIGS. 14F-14H are graphs showing serum levels of IFN-β (FIG. 14F), TNF-α (FIG. 14G), and IL-6 (FIG. 14H) (n=5 per group). Data are presented as means±s.e.m. *, P<0.05; , P<0.01; *, P<0.001; ****, P<0.0001 by one-way ANOVA with Tukey's multiple comparison test.

FIGS. 15A-15E show that exoSTING increases T cell infiltration in the tumor microenvironment without immune cell ablation. FIG. 15A shows images of tumor sections stained with H&E, IFN-β mRNA, CD8, and F4/80 following intratumoral administration of CDN2 (20 μg) or exoCDN2 (0.1 μg). FIG. 15 is a graphical representation of IFN-β positive area. FIG. 15C is a graphical representation of CD8 positive cells. FIGS. 15D-15E are graphical representations of the percentage of CD8 T cells in live $CD45^+$ cells in tumors (FIG. 15D) and CD86 expression on dendritic cells (FIG. 15E) as measured by flow cytometry after 2 doses of PBS, CDN2 (20 μg), and exoCDN2 (0.2 μg) into B16F10 tumors (n=5 per group). *, P<0.05; , P<0.01; **, P<0.0001 by one-way ANOVA with Tukey's multiple comparison test; n.s., non-significant.

FIGS. 16A-16H show that exoSTING induced interferon stimulated gene signatures. FIGS. 16A-16C are box plots showing the relative expression of IFN-β (FIG. 16A), CD274 (FIG. 16B), and CXCL9 (FIG. 16C) as measured by NanoString in RNA samples collected four hours after IT injection of PBS, CDN2 (0.1, 20, or 100 μg), and exoCDN2 (0.001, 0.01, or 0.1 μg) into B16F10 tumors. Data are presented as means±s.e.m. *, P<0.05; , P<0.01; *, P<0.001; **, P<0.0001 by one-way ANOVA with Tukey's multiple comparison test. FIG. 16D shows comparative pathway analysis of the global gene expression changes, analyzed by RNA sequencing, 24 h after 1 or 2 IT injections of CDN2 (20 μg) and exoCDN2 (0.1 μg) into B16F10 tumors. All genes were compared to PBS treatment. FIG. 16E shows normalized expression level of Th1 transcription factors, T-bet and Tcf7. Adjusted P values are indicated. FIG. 16F-16**H shows Gene Set Enrichment Analysis of 3 gene sets that are upregulated by exoCDN2.

FIGS. 17A-17B are graphical representations of activation of purified B cells, T cells, NK cells, and Monocytes from PBMCs after treatment of exoCDN2 (FIG. 17A) or free CDN2 (FIG. 17B). CD86 expression was assessed as a cell activation marker for monocytes, whereas CD69 was used as an activation marker for T cells, NK cells, and B cells.

Figure 17A:
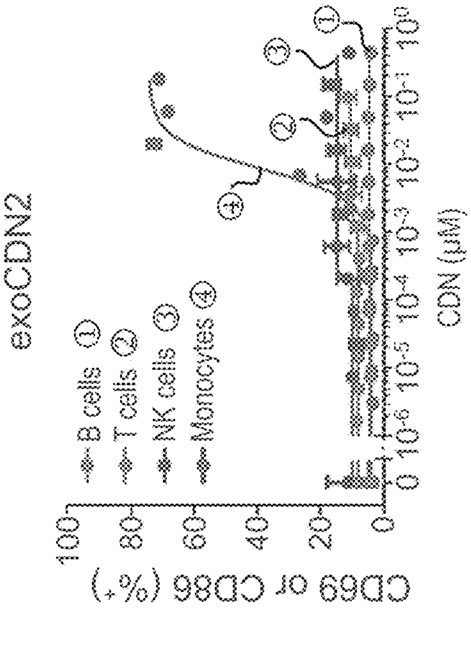
FIGS. 17A-17I show preferential uptake and activation of STING pathway in antigen presenting cells by exoSTING.
Figure 17B:
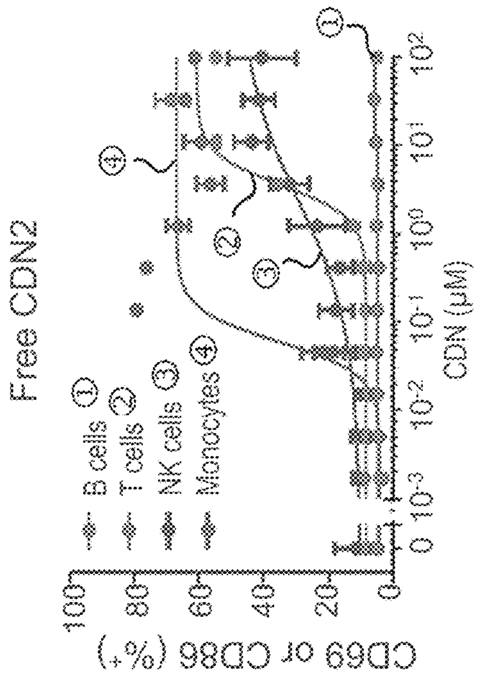
Figure 17C:
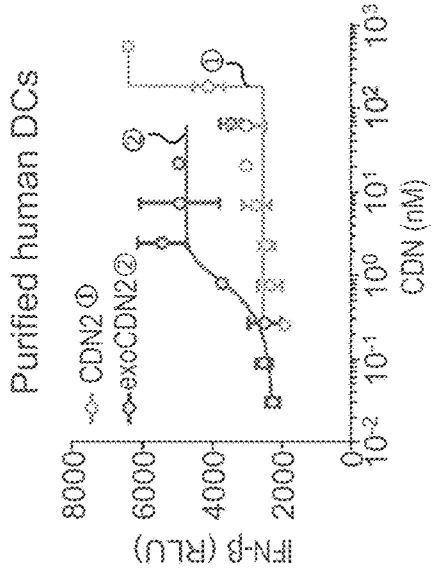
Figure 17D:
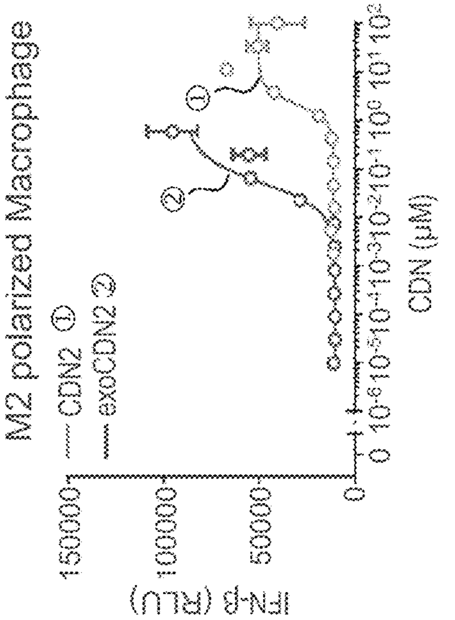
Figure 17E:
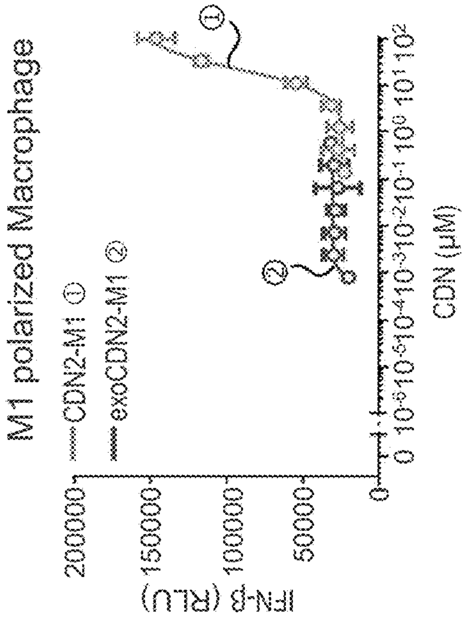

FIG. 17C shows representative dose-response curves of IFN-β production in purified human DCs after treating with exoCDN2 and free CDN2 (n=4). FIGS. 17D and 17E show representative dose-response curves of IFN-β production in M2 polarized human macrophages (FIG. 17D) and M1 polarized human macrophages (FIG. 17E) after treating with exoCDN2 and free CDN2 (n=3).

Figure 17F:
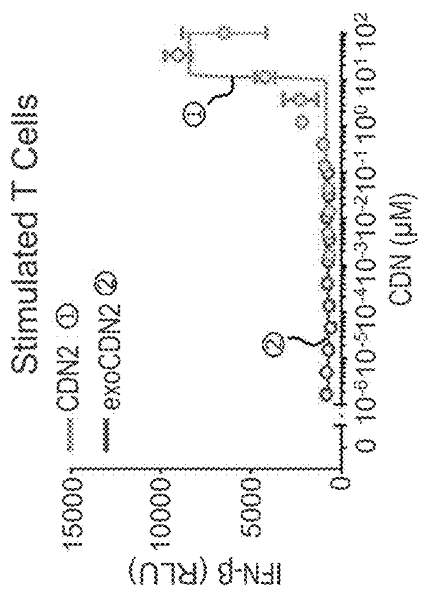
Figure 17G:
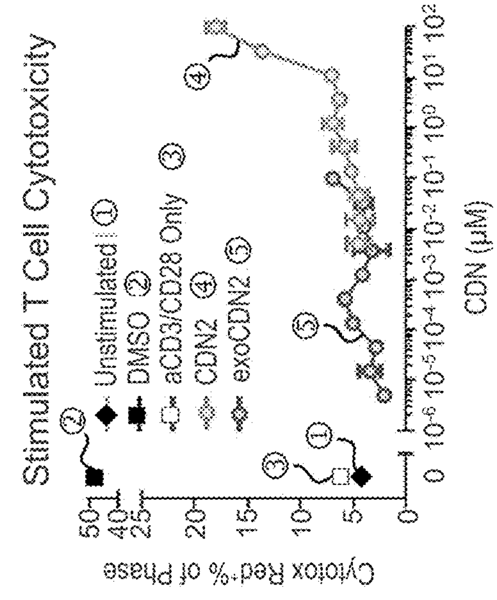

FIGS. 17F and 17G show representative dose-response curves of IFN-β production (FIG. 17F) and cytotoxicity (FIG. 17G) in stimulated T cells after treating with free CDN2 and exoCDN2. T cells were purified from human PBMCs and stimulated with anti-CD3/anti-CD28.

Figure 17H:
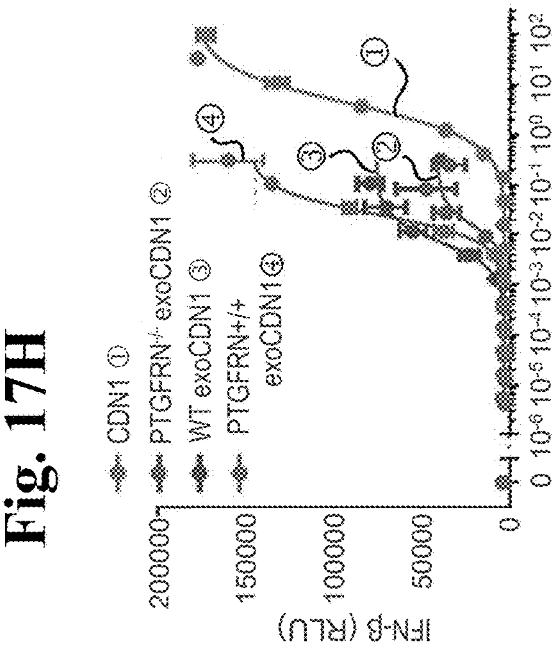
Figure 17I:
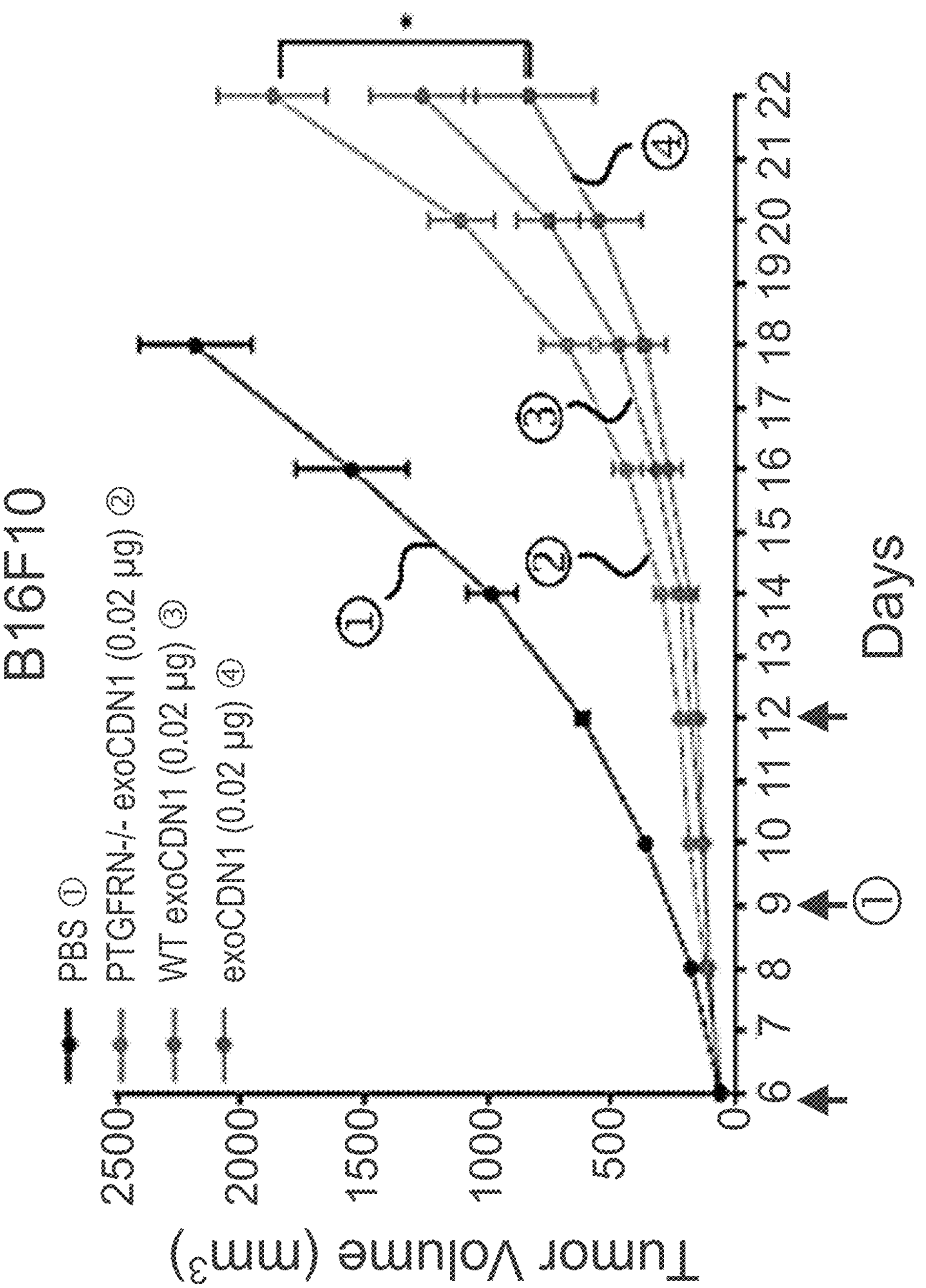

FIG. 17H shows representative dose-response curves of IFN-β production in human PBMC supernatant after incubating with $PTGFRN^{-/-}$ exoCDN1, WT exoCDN1, and $PTGFRN^{+/+}$ exoCDN1 (n=4). FIG. 17I shows B16F10 tumor growth measured after intratumor injection of $PTGFRN^{-/-}$ exoCDN1, WT exoCDN1, and $PTGFRN^{+/+}$ exoCDN1 (n=5 per group). Data are presented as means±s.e.m. RLU: Relative Luminescent Unit.

Figure 18A:
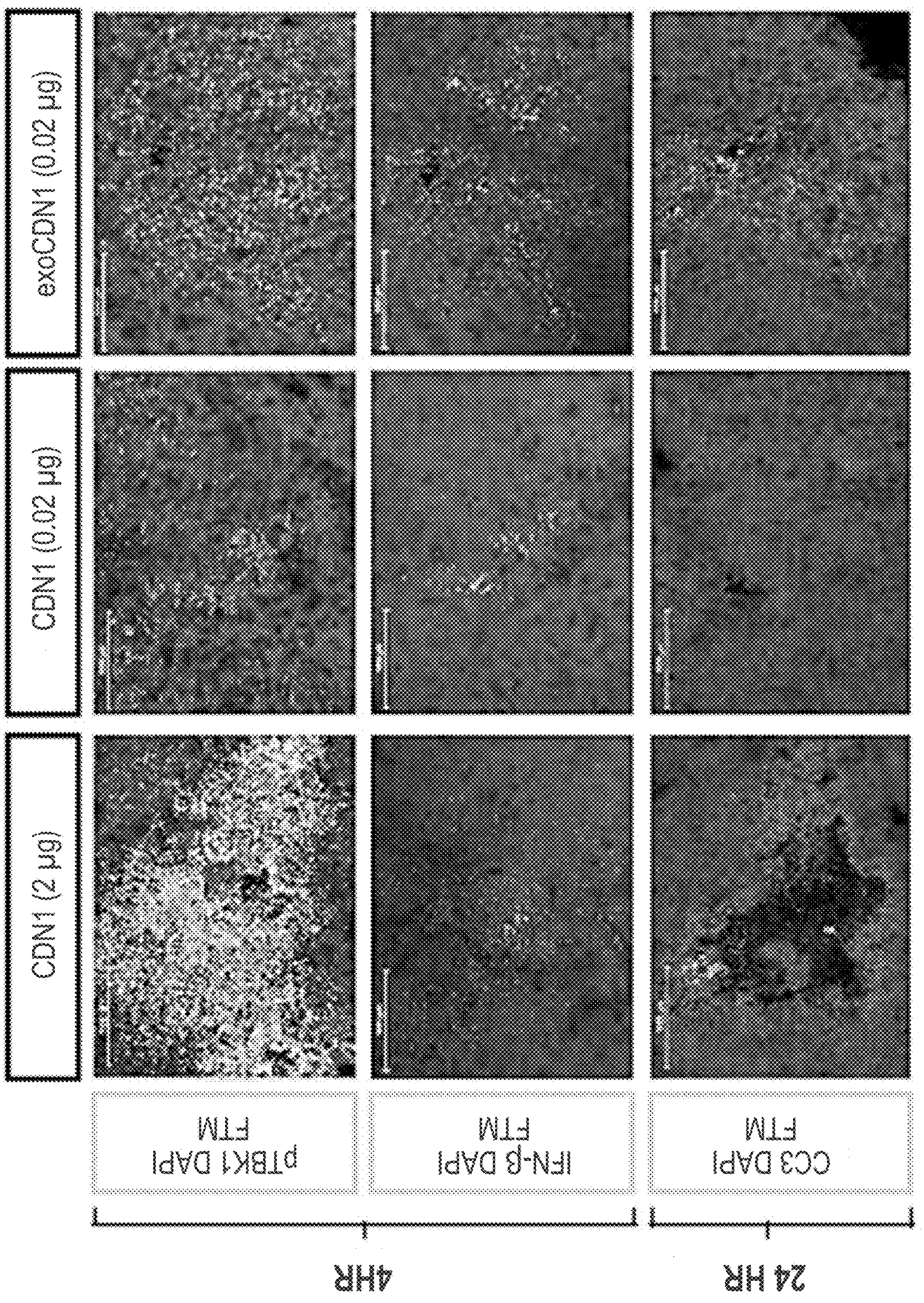
Figure 18B:
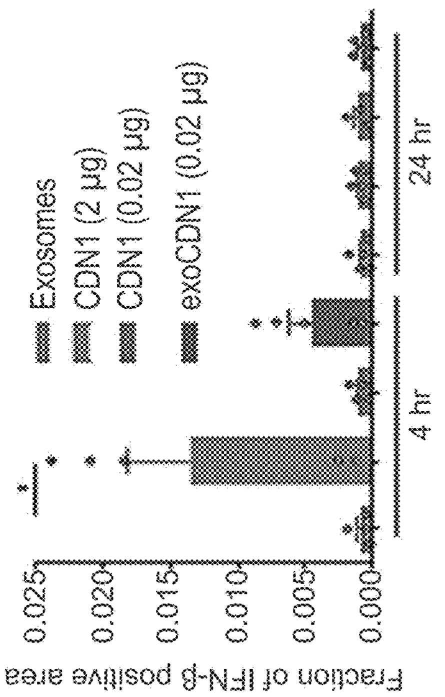
Figure 18C:
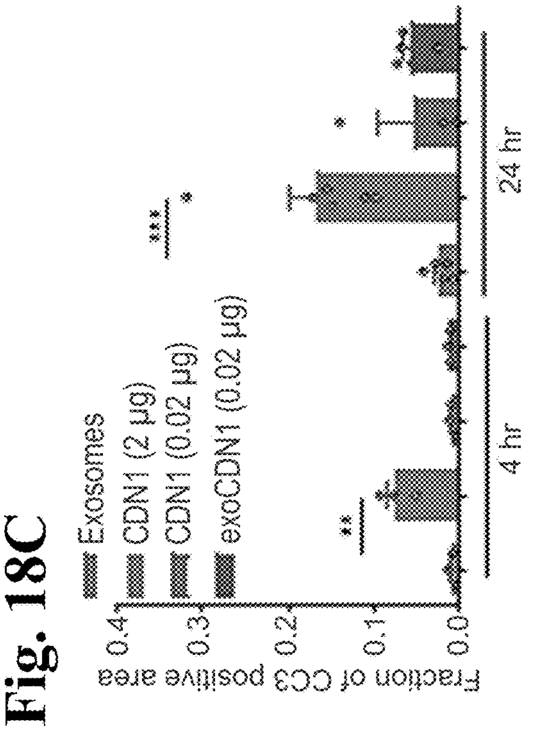
Figure 18D:
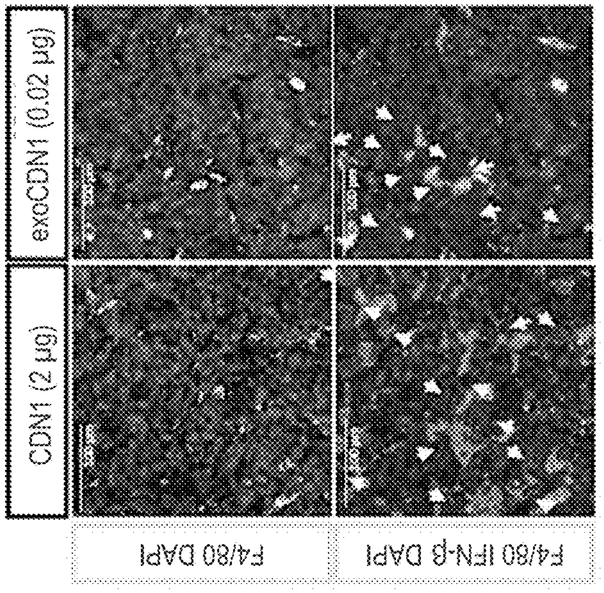

FIGS. 18A-18D show that exoSTING activates STING pathway in APCs without collateral damage of tumors. FIG. 18A shows images of tumor sections stained with pTBK1, IFN-β mRNA, and cleaved caspase 3 (CC3), collected from BALB/cAnNHsd mice that were implanted subcutaneously with A20 B cell lymphoma cells ($1\times10^6$ cells), and administered Intratumorally CDN1 (2 or 0.02 μg) or exoCDN1 (0.02 μg) (n=6) via the CIVO platform. After 4 and 24 hours, tumor sections were stained with pTBK1, IFN-β mRNA, and cleaved caspase 3 (CC3) (FIG. 18A). FIGS. 18B-18C show IFN-β positive area (FIG. 18B) and CC3 positive area (FIG. 18C). *, P<0.05; , P<0.01; *, P<0.001 by one-way ANOVA with Turkey's multiple comparison test. FIG. 18D shows co-localization of F4/80 (yellow) and IFN-β (red) after free CDN (2 μg) and exoCDN1 (0.02 μg) treatment. White arrows indicate the co-localization of F4/80 and IFN-β.

Figure 19:
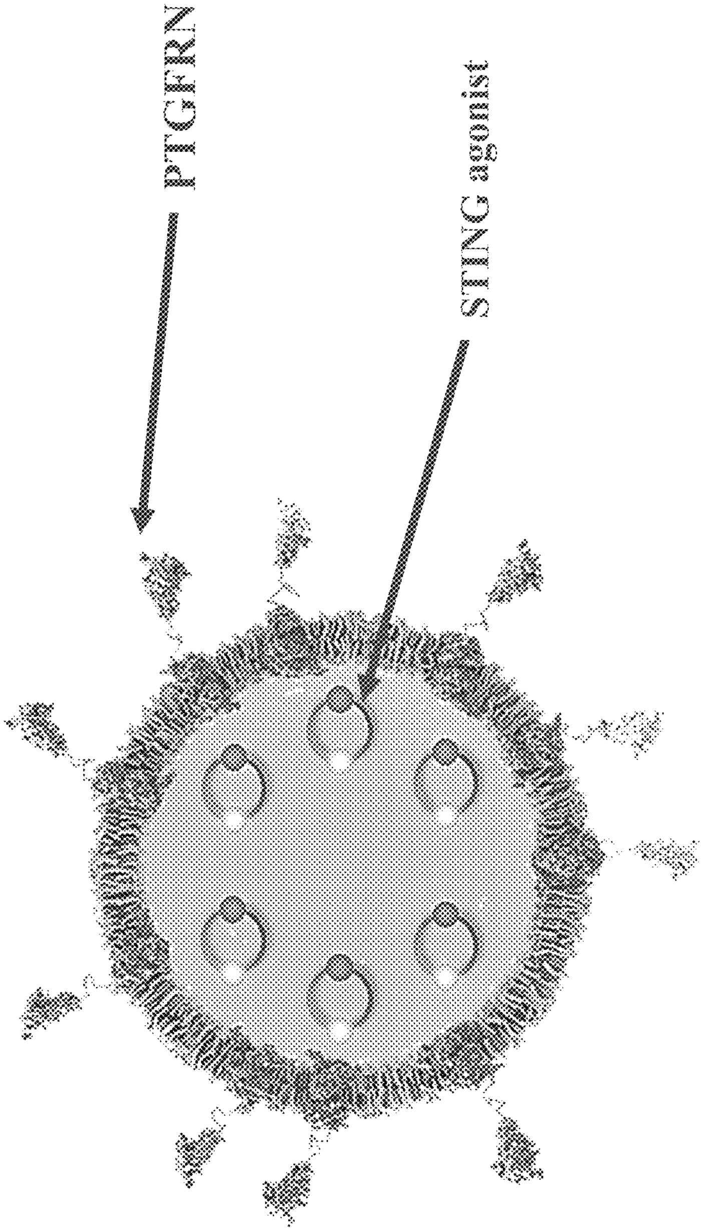

FIG. 19 shows a drawing of an engineered exosome expressing PTGFRN and containing a STING agonist (ExoSTING™).

Figure 20:
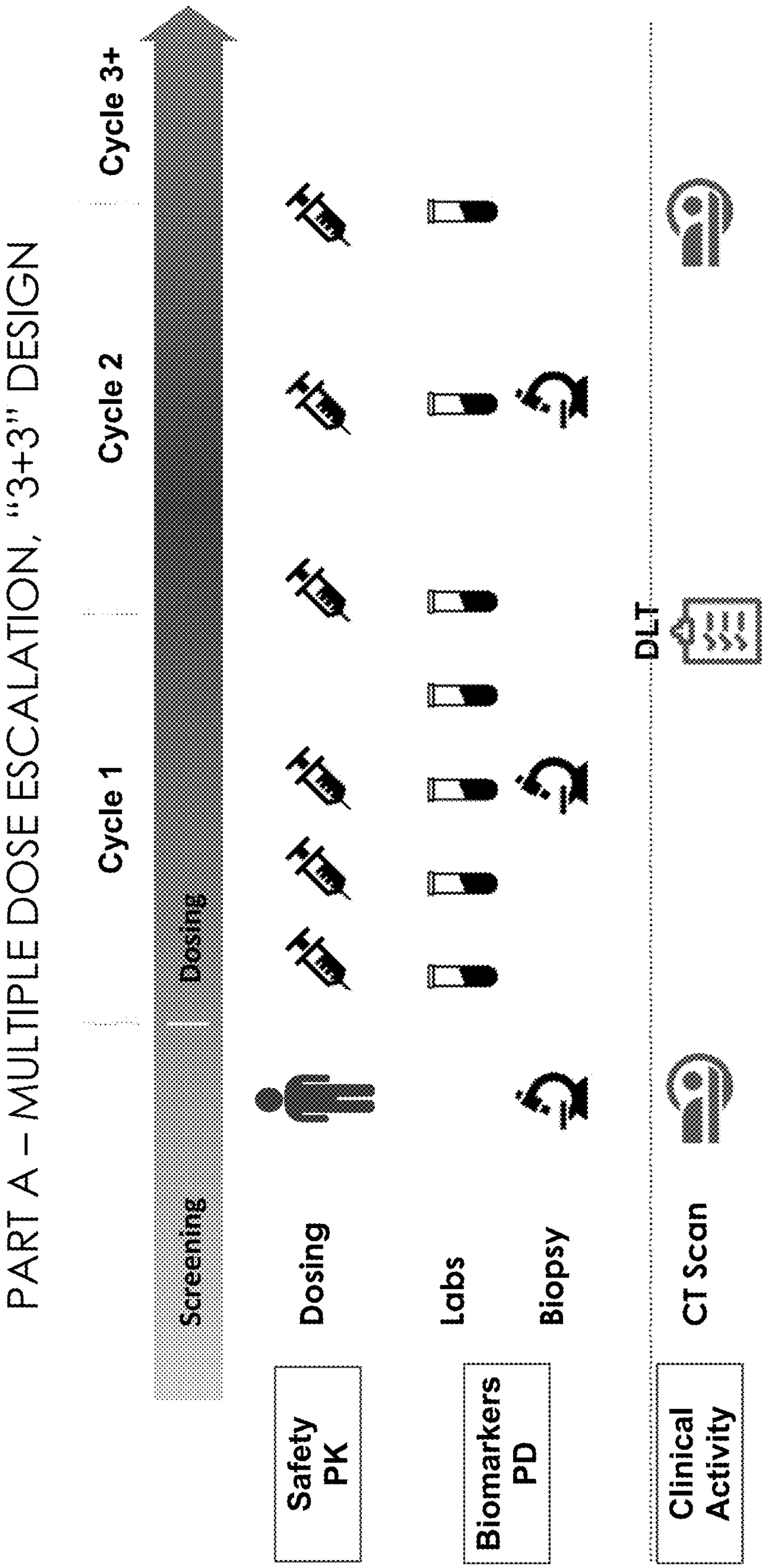

FIG. 20 is a schematic representation of a clinical study assessing the safety and efficacy of exoSTING treatment in cancer patients.

Figure 21B:
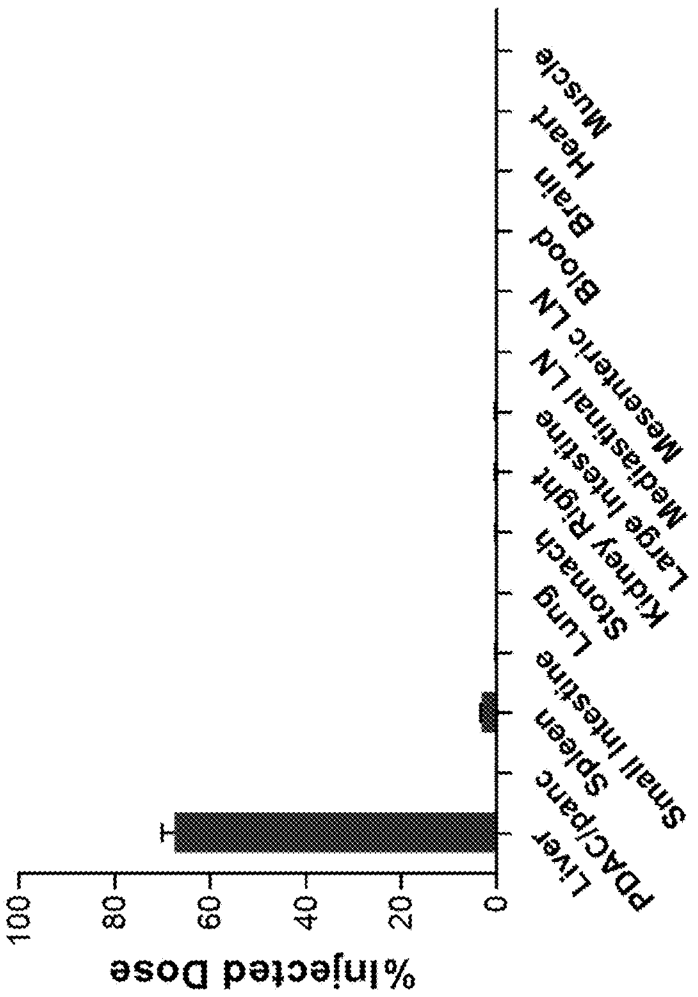
Figure 21A:
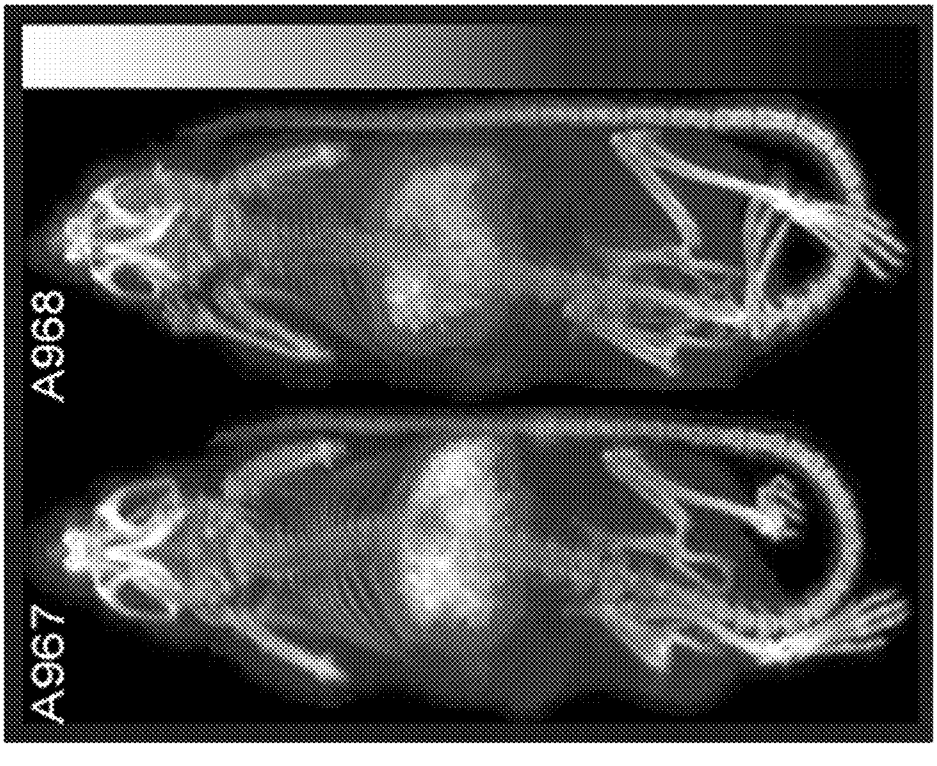

FIGS. 21A and 21B show the biodistribution of EVs, e.g., exosomes, after intravenous administration in an animal model. FIG. 21A provides PET/CT images from two representative animals showing the localization of $^{89}$Zr-DFO labeled exosomes after 24 hours post intravenous administration. FIG. 21B shows the percentage of the injected dose of $^{89}$Zr-DFO labeled exosome present in various tissues at 24 hours post intravenous administration.

Figure 22C:
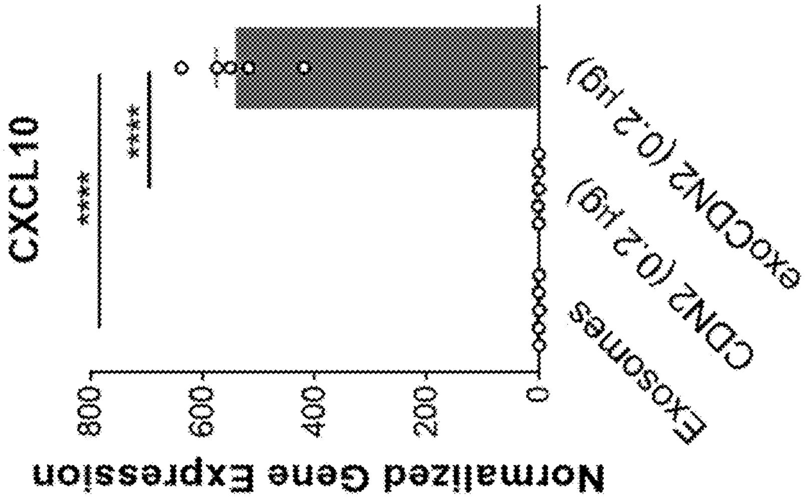
Figure 22B:
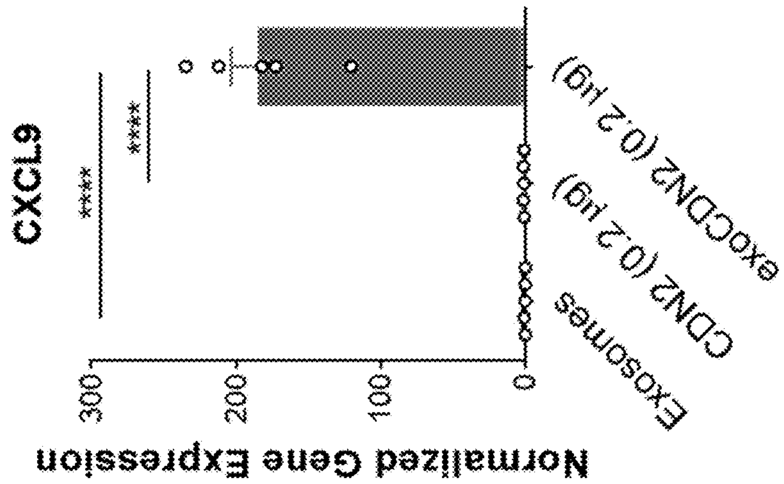
Figure 22A:
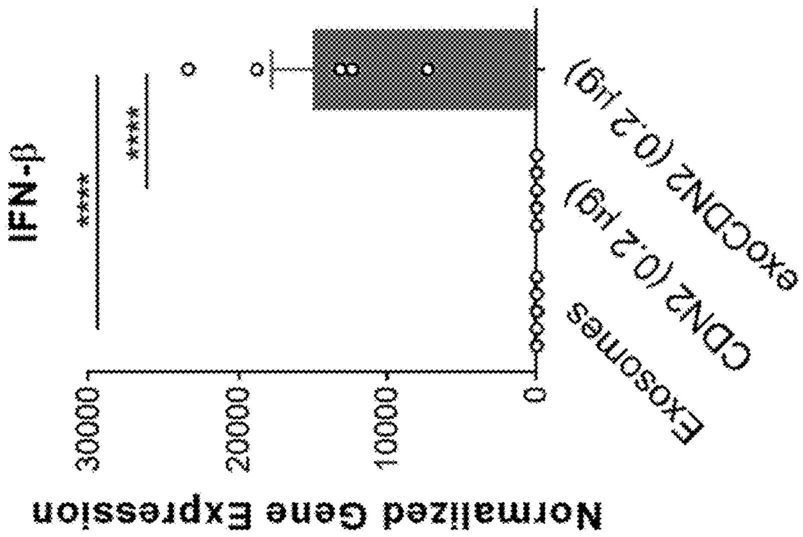

FIGS. 22A, 22B, and 22C provide comparison of IFN-β, CXCL9, and CXCL10 mRNA expression, respectively, in animals that received one of the following: (i) exosome not loaded with CDN; (ii) free CDN2 (0.2 μg) (i.e., not loaded in the lumen of an exosome); and (iii) exosomes loaded with CDN2 (0.2 μg) ("exoCDN2"). Expression of the genes shown were measured four hours after intravenous administration of the different treatments. Data are presented as means±s.e.m. *, P<0.05; ****, P<0.0001 by one-way ANOVA with Tukey's multiple comparison test.

Figure 23C:
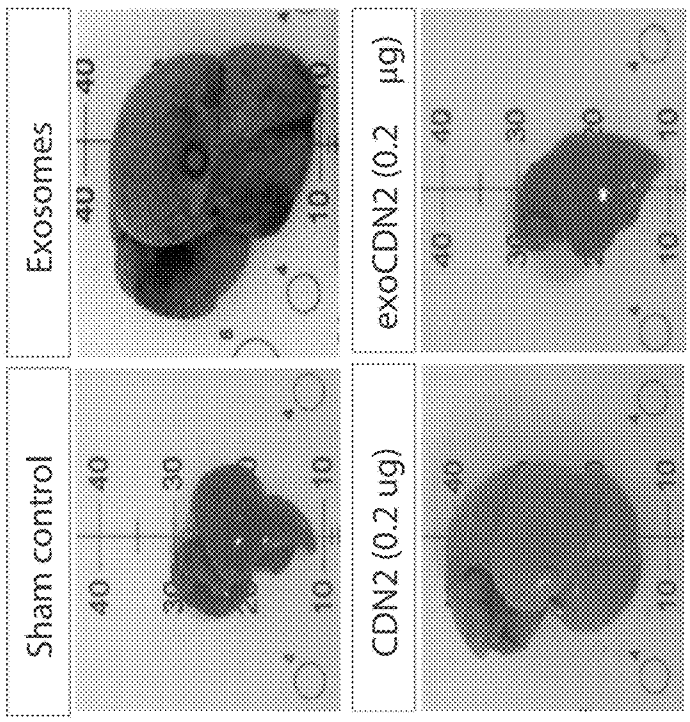
Figure 23B:
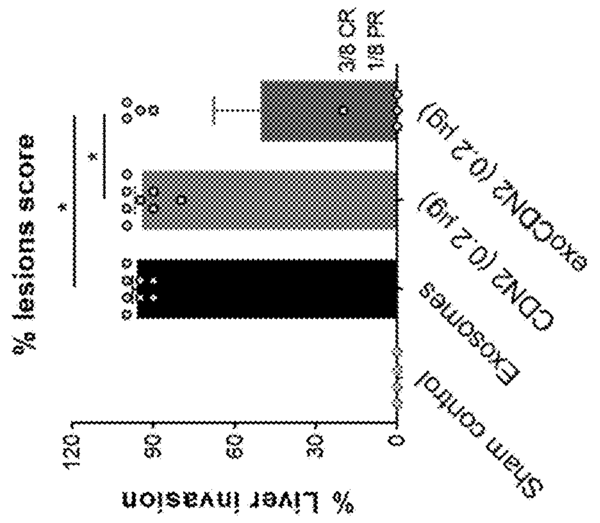
Figure 23A:
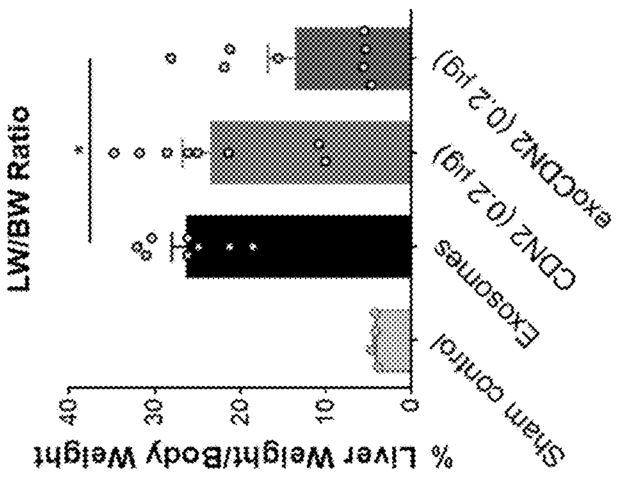

FIGS. 23A, 23B, and 23C shows anti-tumor activity in animals that received an intravenous administration of one of the following: (i) exosome not loaded with CDN; (ii) free CDN2 (0.2 μg) (i.e., not loaded in the lumen of an exosome); and (iii) exosomes loaded with CDN2 (0.2 μg) ("exoCDN2"). Sham control animals were used as controls. FIGS. 23A and 23B provide comparison of the liver/body weight ratio and % lesion score, respectively, for the animals from the different treatment groups. Representative liver images of an animal from the different treatment groups are shown in FIG. 23C.

Figure 24B:
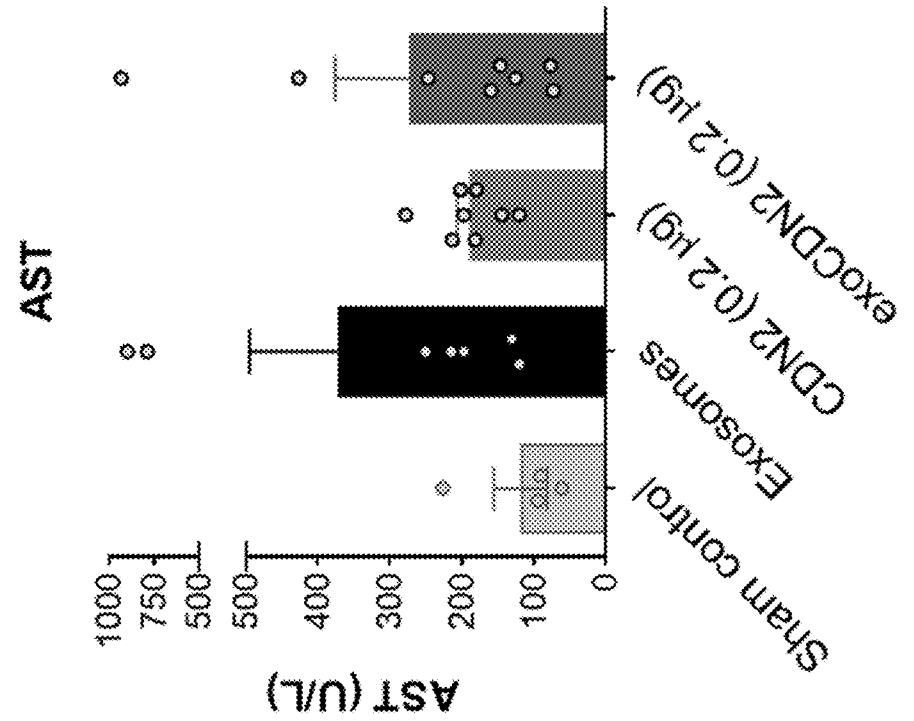
Figure 24A:
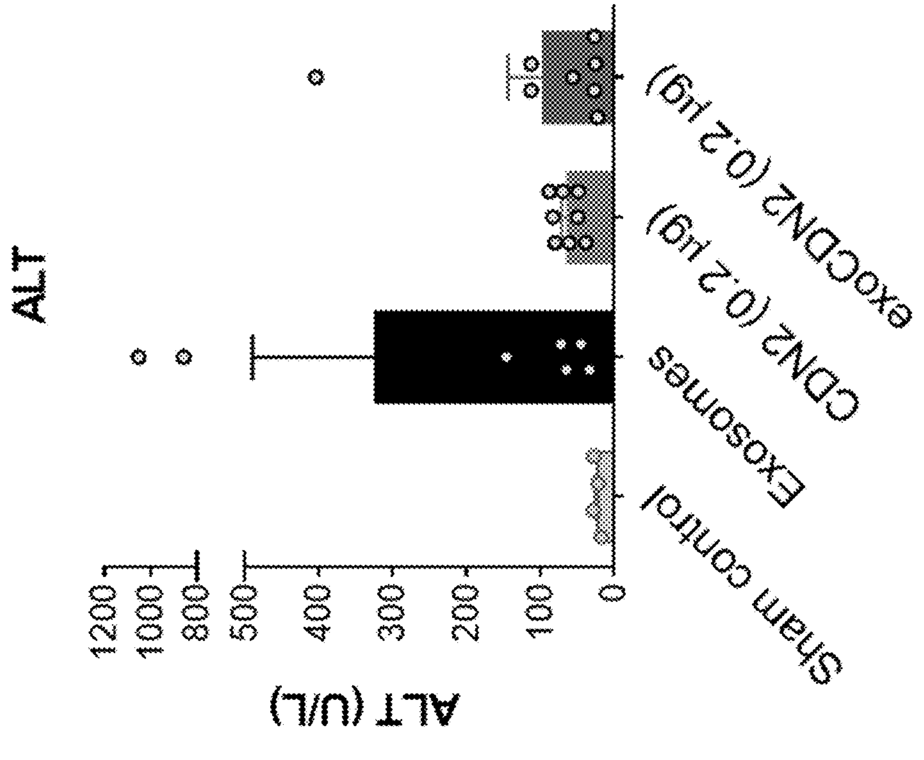

FIGS. 24A-24B provide comparison of ALT and AST liver enzyme levels, respectively, in the sera of animals that received an administration of one of the following: (i) exosome not loaded with CDN; (ii) free CDN2 (0.2 μg) (i.e., not loaded in the lumen of an exosome); and (iii) exosomes loaded with CDN2 (0.2 μg) ("exoCDN2"). Sham control animals were used as controls.

DETAILED DESCRIPTION OF THE DISCLOSURE

The present disclosure is directed to methods of preparing potent extracellular vesicles (EV) comprising cyclic dinucleotides (CDN), e.g., STING agonist. The methods of the disclosure comprise methods of loading CDNs to EVs, methods of separating EVs with loaded CDNs from free CDNs, or any combination thereof.

I. Definitions

It is noted that, as used herein and in the appended claims, the singular forms "a," "an," and "the" include plural referents unless the context clearly dictates otherwise. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" or "approximately" is used herein to mean approximately roughly, around, or in the region of. When the term "about" is used in conjunction with a numerical range, it modifies that range by extending the boundaries above and below the numerical values set forth. The term used herein means within 5% of the referenced amount, e.g., about 50% is understood to encompass a range of values from 47.5% to 52.5%.

As used herein, the term "extracellular vesicle" or "EV" refers to a cell-derived vesicle comprising a membrane that encloses an internal space. EVs comprise all membrane-bound vesicles (e.g., exosomes, nanovesicles) that have a smaller diameter than the cell from which they are derived. Generally EVs range in diameter from 20 nm to 1000 nm, and can comprise various macromolecular payload either within the internal space (i.e., lumen), displayed on the external surface of the EV, and/or spanning the membrane. Said payload can comprise nucleic acids, proteins, carbohydrates, lipids, small molecules, and/or combinations thereof. In some aspects, an EV comprises a scaffold moiety. By way of example and without limitation, EVs include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). EVs can be derived from a living or dead organism, explanted tissues or organs, prokaryotic or eukaryotic cells, and/or cultured cells. In some aspects, EVs are produced by cells that express one or more transgene products.

As used herein the term "exosome" refers to a cell-derived small (between 20-300 nm in diameter, more preferably 40-200 nm in diameter) vesicle comprising a membrane that encloses an internal space (i.e., lumen), and which is generated from said cell by direct plasma membrane budding or by fusion of the late endosome with the plasma membrane. The exosome is a species of EV. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some aspects, an exosome comprises a scaffold moiety. The exosome can be derived from a producer cell, and isolated from the producer cell based on its size, density, biochemical parameters, or a combination thereof. In some aspects, the exosomes of the present disclosure are produced by cells that express one or more transgene products.

As used herein, the term "nanovesicle" refers to a cell-derived small (between 20-250 nm in diameter, more preferably 30-150 nm in diameter) vesicle comprising a membrane that encloses an internal space, and which is generated from said cell by direct or indirect manipulation such that said nanovesicle would not be produced by said producer cell without said manipulation. Appropriate manipulations of said producer cell include but are not limited to serial extrusion, treatment with alkaline solutions, sonication, or combinations thereof. The production of nanovesicles, in some instances, results in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some aspects, a nanovesicle comprises a scaffold moiety. The nanovesicle, once it is derived from a producer cell according to said manipulation, is isolated from the producer cell based on its size, density, biochemical parameters, or a combination thereof.

The term "modified," when used in the context of exosomes described herein, refers to an alteration or engineering of an EV, such that the modified EV is different from a naturally-occurring EV. In some aspects, a modified EV described herein comprises a membrane that differs in composition of a protein, a lipid, a small molecular, a carbohydrate, etc. compared to the membrane of a naturally-occurring EV (e.g., membrane comprises higher density or number of natural EV proteins and/or membrane comprises proteins that are not naturally found in EVs. In certain aspects, such modifications to the membrane changes the exterior surface of the EV. In certain aspects, such modifications to the membrane changes the lumen of the EV.

As used herein, the term "scaffold moiety" refers to a molecule that can be used to anchor STING agonists disclosed herein or any other compound of interest (e.g., payload) to the EV either on the luminal surface or on the exterior surface of the EV. In certain aspects, a scaffold moiety comprises a synthetic molecule. In some aspects, a scaffold moiety comprises a non-polypeptide moiety. In other aspects, a scaffold moiety comprises a lipid, carbohydrate, or protein that naturally exists in the EV. In some aspects, a scaffold moiety comprises a lipid, carbohydrate, or protein that does not naturally exist in the exosome. In certain aspects, a scaffold moiety is Scaffold X. In some aspects, a scaffold moiety is Scaffold Y, as described in International Publ. No. WO/2019/099942; and WO 2020/101740, each of which is incorporated herein by reference in its entirety. Unless indicated otherwise, any disclosure relating to "scaffold moiety" can equally apply to both Scaffold X and Scaffold Y.

As used herein, the term "Scaffold X" refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). In some aspects, a Scaffold X protein can be a whole protein or a fragment thereof (e.g., functional fragment, e.g., the smallest fragment that is capable of anchoring another moiety on the exterior surface or on the luminal surface of the EV, e.g., exosome). In some aspects, a Scaffold X can anchor a moiety (e.g., STING agonist) to the external surface or the luminal surface of the EVs, e.g., exosomes.

As used herein, the term "Scaffold Y" refers to exosome proteins that were newly identified within the lumen of exosomes. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). See WO/2019/099942 and WO 2020/101740, which are incorporated herein by reference in their entireties. In some aspects, a Scaffold Y protein can be a whole protein or a fragment thereof (e.g., functional fragment, e.g., the smallest fragment that is capable of anchoring a moiety to the luminal surface of the exosome). In some aspects, a Scaffold Y can anchor a moiety (e.g., antigen, adjuvant, and/or immune modulator) to the luminal surface of the EV, e.g., exosome.

As used herein, the term "fragment" of a protein (e.g., therapeutic protein, Scaffold X) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some aspects, a functional fragment of a Scaffold X protein retains the ability to anchor a moiety on the luminal surface and/or on the exterior surface of the EV. Whether a fragment is a functional fragment can be assessed by any art known methods to determine the protein content of EVs including Western Blots, FACS analysis and fusions of the fragments with autofluorescent proteins like, e.g., GFP. In certain aspects, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein.

As used herein, the term "variant" of a molecule (e.g., functional molecule, antigen, Scaffold X) refers to a molecule that shares certain structural and functional identities with another molecule upon comparison by a method known in the art. For example, a variant of a protein can include a substitution, insertion, deletion, frameshift or rearrangement in another protein.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences is accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X is modified at any convenient location.

As used herein the term "producer cell" refers to a cell used for generating an EV. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, s9f cells, fHTDF fibroblast cells, AGE.HN® neuronal precursor cells, CAP® amniocyte cells, adipose mesenchymal stem cells, and RPTEC/TERT1 cells. In certain aspects, a producer cell is an antigen-presenting cell. In some aspects, the producer cell is a bacterial cell. In some aspects, a producer cell is a dendritic cell, a B cell, a mast cell, a macrophage, a neutrophil, a Kupffer-Browicz cell, or a cell derived from any of these cells, or any combination thereof. In some aspects, the producer cell is not a bacterial cell. In other aspects, the producer cell is not an antigen-presenting cell.

As used herein the term "associated with" refers to encapsulation of a first moiety, e.g., a STING agonist, into a second moiety, e.g., EV, or to a covalent or non-covalent bond formed between a first moiety and a second moiety, e.g., a STING agonist and an EV, respectively, e.g., a scaffold moiety expressed in or on the EV and a STING agonist, e.g., Scaffold X (e.g., a PTGFRN protein), respectively, on the luminal surface of or on the external surface of the EV. In one aspect, the term "associated with" means a covalent, non-peptide bond or a non-covalent bond. For example, the amino acid cysteine comprises a thiol group that can form a disulfide bond or bridge with a thiol group on a second cysteine residue. Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity. In other aspects, the term "associated with" means that a state of encapsulation by a first moiety, e.g., EV of a second moiety, e.g., a STING agonist. In the encapsulation state, the first moiety and the second moiety can be linked to each other. In other aspects, the encapsulation means that the first moiety and the second moiety are not physically and/or chemically linked to each other.

As used herein the term "linked to" or "conjugated to" are used interchangeably and refer to a covalent or non-covalent bond formed between a first moiety and a second moiety, e.g., a STING agonist and an EV, respectively, e.g., a scaffold moiety expressed in or on the EV and a STING agonist, e.g., Scaffold X (e.g., a PTGFRN protein), respectively, on the luminal surface of or on the external surface of the EV.

The term "encapsulated", or grammatically different forms of the term (e.g., encapsulation, or encapsulating), refers to a status or process of having a first moiety (e.g., STING agonist) inside a second moiety (e.g., an EV, e.g., exosome) without chemically or physically linking the two moieties. In some aspects, the term "encapsulated" can be used interchangeably with "in the lumen of". Non-limiting examples of encapsulating a first moiety (e.g., STING agonist) into a second moiety (e.g., EVs, e.g., exosomes) are disclosed elsewhere herein.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In other aspects, an isolated EV composition has an amount and/or concentration of desired EVs at or above an acceptable amount and/or concentration. In other aspects, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some aspects, isolated EV preparations are substantially free of residual biological products. In some aspects, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "agonist" refers to a molecule that binds to a receptor and activates the receptor to produce a biological response. Receptors can be activated by either an endogenous or an exogenous agonist. Non-limiting examples of endogenous agonist include hormones, neurotransmitters, and cyclic dinucleotides. Non-limiting examples of exogenous agonist include drugs, small molecules, and cyclic dinucleotides. The agonist can be a full, partial, or inverse agonist. In one aspect, the term "STING agonist" refers to any cyclic dinucleotide (CDN) detailed in the present disclosure. Accordingly, unless indicated otherwise, the term "STING agonist" and "CDN" are used interchangeably.

As used herein, the term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, beta-blocker, and calcium channel blockers. The antagonist can be a competitive, non-competitive, or uncompetitive antagonist.

The term "free STING agonist" or "free cyclic dinucleotide (CDN)" as used herein means a CDN or STING agonist not associated with an EV, but otherwise identical to the CDN or STING agonist associated with the EV. Especially when compared to an EV associated with a CDN or STING agonist, the free CDN or STING agonist is the same CDN or STING agonist associated with the EV. In some aspects, when a free CDN or STING agonist is compared to an EV comprising the CDN or STING agonist in its efficacy, toxicity, and/or any other characteristics, the amount of the free CDN or STING agonist compared to the CDN or STING agonist associated with the EV is the same as the amount of the CDN or STING agonist associated with the EV.

The term "exoSTING" as used herein refers to an exosome loaded with a STING agonist. For example, an "exoCDN2" refers to an exosome loaded with CDN2 (cAIM (PS)2 Difluor, a 3'-3' CDN). An "exoCDN1" refers to an exosome loaded with CDN1 (ML RR-S2, a 2'-3' CDN). In some aspects, the exosome comprises STING agonist in the lumen of the exosome. In some aspects, the STING agonist is associated with the luminal surface of the exosome, e.g., with a scaffold protein, e.g., Scaffold X, e.g., PTGFRN. In some aspects, the STING agonist is encapsulated within the lumen of the exosome and is not associated with a scaffold protein. In some aspects, the exosome comprises the STING agonist on the surface of the exosome. In some aspects, the STING agonist is associated with the exterior surface of the exosome. In some aspects, the STING agonist is linked to or conjugated to the exterior surface of the exosome. In some aspects, the STING agonist is linked to or conjugated to a surface exposed scaffold protein, e.g, a Scaffold X protein, e.g., a PTGFRN protein. In some aspects, the STING agonist is linked to or conjugated to the lipid bilayer of the exosome.

The term "flow-through" or "flow-through mode" as used herein refers to the general purification approach wherein contaminants are removed from a mixture during chromatography because they are retained by a chromatographic process, usually bound to a resin in a column. A target is purified because it does not bind to a chromatographic medium, usually a resin in a column, and instead flows through to be collected. After elution of the target, the impurities bound to the column must be "stripped", or removed from the column, so that the column can then be regenerated for another chromatographic run. This approach differs from "bind-and-elute" or "bind-and-elute mode" wherein the target is retained on a column and impurities flow through the column.

As used herein, the term "ligand" refers to a molecule that binds to a receptor and modulates the receptor to produce a biological response. Modulation can be activation, deactivation, blocking, or damping of the biological response mediated by the receptor. Receptors can be modulated by either an endogenous or an exogenous ligand. Non-limiting examples of endogenous ligands include antibodies and peptides. Non-limiting examples of exogenous agonist include drugs, small molecules, and cyclic dinucleotides. The ligand can be a full, partial, or inverse ligand.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)2, Fab, Fab', and $F(ab')_2$, $F(ab1)_2$, Fv, dAb, and Fd fragments, diabodies, and antibody-related polypeptides. Antibody includes bispecific antibodies and multispecific antibodies so long as they exhibit the desired biological activity or function.

As used herein the term "therapeutically effective amount" is the amount of reagent or pharmaceutical compound that is sufficient to a produce a desired therapeutic effect, pharmacologic and/or physiologic effect on a subject in need thereof. A therapeutically effective amount can be a "prophylactically effective amount" as prophylaxis can be considered therapy.

As used herein, the term "pharmaceutical composition" refers to one or more of the compounds described herein, such as, e.g., an EV mixed or intermingled with, or suspended in one or more other chemical components, such as pharmaceutically-acceptable carriers and excipients. One purpose of a pharmaceutical composition is to facilitate administration of preparations of EVs to a subject. The term "excipient" or "carrier" refers to an inert substance added to a pharmaceutical composition to further facilitate administration of a compound. The term "pharmaceutically-acceptable carrier" or "pharmaceutically-acceptable excipient" and grammatical variations thereof, encompasses any of the agents approved by a regulatory agency of the US Federal government or listed in the US Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "payload" refers to a therapeutic agent that acts on a target (e.g., a target cell) that is contacted with the EV. Payloads that can be introduced into an EV and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA), amino acids (e.g., amino acids comprising a detectable moiety or a toxin or that disrupt translation), polypeptides (e.g., enzymes), lipids, carbohydrates, and small molecules (e.g., small molecule drugs and toxins).

The terms "administration," "administering" and variants thereof refer to introducing a composition, such as an EV, or agent into a subject and includes concurrent and sequential introduction of a composition or agent. The introduction of a composition or agent into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

The term "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

The term "prevent" or "preventing," as used herein, refers to decreasing or reducing the occurrence or severity of a particular outcome. In some aspects, preventing an outcome is achieved through prophylactic treatment.

As used herein, the term "modulate," "modulating", "modify," and/or "modulator" generally refers to the ability to alter, by increase or decrease, e.g., directly or indirectly promoting/stimulating/up-regulating or interfering with/inhibiting/down-regulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity.

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some aspects, the subject is a mammal, and in other aspects the subject is a human.

As used herein, the term "substantially free" means that the sample comprising EVs comprise less than 10% of macromolecules by mass/volume (m/v) percentage concentration. In some aspects, some fractions contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, exogenous proteins, lipids, carbohydrates, metabolites, or a combination thereof.

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

II. Methods of Preparing Extracellular Vesicles

The present disclosure provides methods of preparing potent extracellular vesicles (EVs) (e.g., exosomes) comprising cyclic dinucleotides (CDNs), e.g., STING agonist, by adjusting or modifying the incubation condition, cleaning (purification and/or separation) condition, and/or combinations thereof. Those relevant conditions include, but are not limited to, a loading concentration of CDNs and/or EVs, a chromatography, a pH used for loading and/or separation, a final concentration of CDNS and/or EVs, or any combinations thereof.

IIA. EV Chromatography Purification

Also provided are methods of preparing a composition comprising EVs (e.g., exosomes) associated with one or more cyclic dinucleotides (CDNs), wherein the method comprises incubating the EVs with a loading concentration of cyclic dinucleotides (CDNs) in a mixture, wherein, after the incubation, the composition comprises EVs with loaded CDNs and free CDNs, and wherein the free CDNs are removed by a multimodal chromatography.

In some aspects, the multimodal chromatography removes some or all of the free CDNs present in the composition. In certain aspects, after the multimodal chromatography, the percentage of free CDNs present in the composition is less than about 1 percent, less than about 5 percent, less than about 10 percent, less than about 15 percent, less than about 20 percent, less than about 25 percent, less than about 30 percent, less than about 35 percent, less than about 40 percent, less than about 45 percent, less than about 50 percent, less than about 55 percent, less than about 60 percent, less than about 65 percent, less than about 70 percent, less than about 75 percent, less than about 80 percent, less than about 85 percent, less than about 90 percent, or less than about 55 percent.

The present disclosure provides methods of preparing, isolating or purifying an extracellular vesicle (e.g., exosomes) comprising a STING agonist, e.g., a cyclic dinucleotide (CDN), with higher potency and/or stability. In some aspects, the methods of the present disclosure are useful for preparing a composition comprising EVs associated with a STING agonist, e.g., one or more cyclic dinucleotides (CDNs), comprising incubating the EVs with the STING agonist, e.g., one or more cyclic dinucleotides (CDNs) in a mixture at a particular pH. In other aspects, the methods of the present disclosure provides removing or separating free STING agonists, e.g., CDN, from the EVs using a chromatography. In some aspects, the chromatography includes a multimodal chromatography. As described herein, in some aspects, the methods for removing or separating free STING agonists from the EVs can be performed in combination with one or more of the other methods disclosed herein. For instance, in certain aspects, the methods for removing or separating free STING agonists from the EVs can be performed after incubating the EVs with the STING agonist in a mixture, as described herein.

The methods of the present disclosure are also related to purification of EVs after incubation with the CDN, e.g., STING agonist, to remove free, unassociated or unencapsulated CDN, e.g., STING agonist, from the composition. In some aspects, separation is on the basis of physical or biological properties of EVs, e.g., exosomes. The multimodal chromatography can be used, in some aspects, to remove free STING agonist from an EV preparation. In some aspects, physical properties of EVs, e.g., exosomes, are employed to separate them from a medium or other source material, including separation on the basis of electrical charge (e.g., electrophoretic separation), size (e.g., filtration, molecular sieving, etc), density (e.g., regular or gradient centrifugation), Svedberg constant (e.g., sedimentation with or without external force, etc). In some aspects, isolation is based on one or more biological properties, and include methods that employ surface markers (e.g., for precipitation, reversible binding to solid phase, FACS separation, specific ligand binding, non-specific ligand binding, etc.). In some aspects, the EVs, e.g., exosomes, are fused using chemical and/or physical methods, including PEG-induced fusion and/or ultrasonic fusion. In some aspects, the multimodal chromatography uses a column that is selected from a group comprising CaptoCore 700 (CC700), Capto MMC, or Capto MMC ImpRes. In some aspects, the multimodal column is Captocore 700. In some aspects, the multimodal column is Captocore MMC. In some aspects, the multimodal column is Capto MMC ImpRes.

The methods of the present disclosure also use anion exchange or cation exchange chromatography as part of a chromatography to separate EVs. Various CEX ligands can be used in the chromatography. In some aspects, the CEX ligands comprise sulfate, sulfopropyl, sulfobutyl, sulfoisobutyl, sulfoethyl, sulfonate, sulfonic acid, carboxymethyl, carboxylic acid, glutamic acid, aspartic acid, histidine, hydroxyl, and/or phosphate ligands. In some aspects, CEX ligands are used together with other conventional chromatography ligands such as sulfate ligands, tertiary amine ligands, quaternary amine ligands, diethaminoethyl ligands, butyl ligands, hexyl ligands, ether ligands, polypropylene glycol ligands, phenyl ligands, ceramic hydroxy apatite ceramic fluoroapatite ligands, amino acid ligands, or any combination thereof. In some aspects, commercially available chromatography ligands are used, for example, those formulated as SP SEPHAROSE™ FF, SP SEPHAROSE™ HP, SP SEPHAROSE™ BB, SP SEPHAROSE™ XL CM SEPHAROSE™ FF, CM SEPHAROSE™ HP, SOURCE™ 15S, SOURCE™ 30S, CAPTO™ S, MacroCap SP, CAPTO™ SP ImpRes, or CAPTO™ S ImpAct available from GE Healthcare; FRACTOGEL® EMD SO3- (M), FRACTOGEL® EMD SO3- (S), FRACTOGEL® EMD SE Hicap (M), ESHMUNO® S, or ESHMUNO® CPX available from Merck Millipore; TOYOPEARL® CM-650C, TOYOPEARL® CM-650M, TOYOPEARL® CM-650S, TOYOPEARL® SP-650C, TOYOPEARL® SP-650M, TOYOPEARL® SP-650S, TOYOPEARL® SP-550C, TOYOPEARL® MEGACAP® II SP-550 EC, TOYOPEARL® GIGACAP® S-650M, TOYOPEARL® GIGACAP® CM-650M, or TOYOPEARL® GIGACAP® S-650S available from Tosoh Bioscience; MACRO-PREP® High S, MACRO-PREP® 25 S, MACRO-PREP® CM, UNOSPHERE™ S, NUVIA™ S, or NUVIA™ HR-S available from BioRad Laboratories; S HYPERCEL™, CM Ceramic HYPERD® F, S Ceramic HYPERD® 20, S Ceramic HYPERD® F, CMM HYPERCEL™, or HYPERCEL™ STAR CEX, available from Pall Corporation; POROS® 50 HS, POROS® 20 HS, or POROS® XS, available from Thermo Fisher Scientific/Life Technologies; PL-SCX 1000 Å 30 μm or PL-SCX 1000 Å 10 μm, available from Agilent Technologies; CELLUFINE® MAX S-r, CELLUFINE® MAX S-h, or CELLUFINE® C-500 (m), available from INC Corporation; BAKERBOND™ POLYABx or BAKERBOND™ POLYABx, available from Avantor Pharmaceutical Materials; YMC—BioPro S30, YMC—BioPro S75, YMC—BioPro SmartSep S10, YMC—BioPro SmartSep S30, or YMC—BioPro SmartSep S30, available from YMC; or PRAESTO™ SP45, PRAESTO™ SP65, or PRAESTO™ SP65, available from Purolite. In some aspects, the CEX resin used in the purification process can be POROS® XS, available from Thermo Fisher Scientific/Life Technologies. In some aspects, a CEX ligand for the CEX process is POROS® XS.

Various AEX resins can also be used in the current methods. AEX resin refers to a solid phase which is positively charged, e.g. having one or more positively charged ligands. In some aspects, the ligands are selected from diethylaminopropyl, diethylaminoethyl, quaternary aminoethyl, quaternary ammonium, carboxymethyl, carboxylic acid, glutamic acid, aspartic acid, histidine, hydroxyl, phosphate, tertiary amines, quaternary amines, diethaminoethyl, dimethylaminoethyl, trimethylaminoethyl, an amino acid ligand, or combinations thereof. Commercially available anion exchange resins include DEAE cellulose, QAE SEPHADEX and FAST Q SEPHAROSE (Pharmacia). In certain aspects the chromatography ligands can be bound to a base matrix. In some aspects, the base matrix can comprise monoliths, hydrogels, porous devices, nanofibers, composite resins, beaded resins, beaded resin with inert porous shells, and/or any other solid or porous support. In some aspects, the base matrix can comprise cellulose, agarose, polystyrene derivatives, polyvinyl ether, silica, methacrylate derivatives, glass, ceramic hydroxyapatite, acrylamide, and/or other backbones commonly used in chromatography.

Examples of anion exchange resins include, but are not limited to: Q SEPHAROSE™ FF, Q SEPHAROSE™ HP, Q SEPHAROSE™ BB, Q SEPHAROSE™ XL, DEAE SEPHAROSE™ FF, ANX SEPHAROSE™ 4FF low sub, ANX SEPHAROSE™ 4FF high sub, SOURCE™ 15Q, SOURCE™ 30Q, CAPTO™ Q, CAPTO™ DEAE, or CAPTO™ Q ImpRes, available from GE Healthcare; FRACTOGEL® EMD DEAE (M), FRACTOGEL® EMD TMAE (M), FRACTOGEL® EMD TMAE (S), FRACTOGEL® EMD TMAE Hicap (M), FRACTOGEL® EMD TMAE Medcap (M), ESHMUNO® Q or ESHMUNO® Q, available from Merck Millipore; TOYOPEARL® DEAE-650C, TOYOPEARL® DEAE-650M, TOYOPEARL® DEAE-650S, TOYOPEARL® SuperQ-650C, TOYOPEARL® SuperQ-650M, TOYOPEARL® SuperQ-650S, TOYOPEARL® QAE-550C, TOYOPEARL® GIGACAP® Q-650M, TOYOPEARL® Q-600C AR, TOYOPEARL® GIGACAP® DEAE-650M, TOYOPEARL® GIGACAP® Q-650S, TOYOPEARL® NH2-750F, TSKGEL® SuperQ-5PW (20 μm), or TSKGEL® SuperQ-5PW (30 μm), available from Tosoh Bioscience; MACRO-PREP® DEAE, MACRO-PREP® High Q, MACRO-PREP® 25 Q, UNOSPHERE™ Q or NUVIA™ Q, available from BioRad Laboratories; Q HYPERCEL™, DEAE Ceramic HYPERD® F, Q Ceramic HYPERD® 20, Q Ceramic HYPERD® F, or HYPERCEL™ STAR AX, available from Pall Corporation; POROS® 50 HQ, POROS® 50 PI, POROS® 50 D, POROS® 20 HQ, or POROS® XQ, available from Thermo Fisher Scientific/Life Technologies; DEAE PuraBead HF, available from Prometic Bioseparations; PL-SAX 1000 Å 30 μm, or PL-SAX 1000 Å 10 μm, available from Agilent Technologies; CELLUFINE® MAX Q-h, or CELLUFINE® Q-500 (m), available from JNC Corporation; BAKERBOND™ POLYQUAT, BAKERBOND™ POLYPEI, or BAKERBOND™ POLYPEI, available from Avantor Pharmaceutical Materials; YMC—BioPro Q30, YMC—BioPro Q75, YMC—BioPro SmartSep Q10, or YMC—BioPro SmartSep Q30, available from YMC; Sartobind Q, available from 8 mm; or PRAESTO™ Q65 or PRAESTO™ Q90, available from Purolite. In some aspects the AEX resin can be Sartobind Q, available from 8 mm. In some aspects, an AEX resin for the AEX process is SARTOBIND® Q (8 mm).

The methods of the present disclosure also use size exclusion chromatography to separate the EVs. In some aspects, size exclusion chromatography can be utilized to isolate or purify the EVs, e.g., exosomes. Size exclusion chromatography techniques are known in the art. In some aspects, a void volume fraction is isolated and comprises the EVs, e.g., exosomes, of interest. In some aspects, for example, density gradient centrifugation can be utilized to further isolate the EVs, e.g., exosomes. Still further, in some aspects, it can be desirable to further separate the producer cell-derived EVs, e.g., exosomes, from EVs of other origin. For example, the producer cell-derived EVs, e.g., exosomes, can be separated from non-producer cell-derived EVs, e.g., exosomes, by immunosorbent capture using an antigen antibody specific for the producer cell.

The methods of the present disclosure are useful for improving or maintaining the potency of CDNs, e.g., STING agonists after chromatography. In some aspects, the chromatography is a multimodal chromatography. In some aspects, after the multimodal chromatography, the CDNs are at a final concentration of from about 0.5 μM to about 10 μM. In some aspects, after the multimodal chromatography, the CDNs are at a final concentration of between about 1 μM and about 10 μM, between about 2 μM and about 10 μM, between about 2 μM and about 9 μM, between about 3 μM and about 9 μM, between about 3 μM and about 8 μM, between about 4 μM and about 8 μM, between about 4 μM and about 7 μM, or between about 4 μM and about 6 μM. In some aspects, the final cyclic dinucleotide concentration is from about 0.5 μM to about 10 μM. In some aspects, the final cyclic dinucleotide concentration is about 1 μM. In some aspects, the final cyclic dinucleotide concentration is about 2 μM. In some aspects, the final cyclic dinucleotide concentration is about 3 μM. In some aspects, the final cyclic dinucleotide concentration is about 4 μM. In some aspects, the final cyclic dinucleotide concentration is about 5 μM. In some aspects, the final cyclic dinucleotide concentration is about 6 μM. In some aspects, the final cyclic dinucleotide concentration is about 7 μM. In some aspects, the final cyclic dinucleotide concentration is about 8 μM. In some aspects, the final cyclic dinucleotide concentration is about 9 μM. In some aspects, the final cyclic dinucleotide concentration is about 10 μM. In some aspects, the final cyclic dinucleotide concentration is about 11 μM. In some aspects, the final cyclic dinucleotide concentration is about 12 μM. In some aspects, the final cyclic dinucleotide concentration is about 13 μM. In some aspects, the final cyclic dinucleotide concentration is about 14 μM. In some aspects, the final cyclic dinucleotide concentration is about 15 μM. In some aspects, the final cyclic dinucleotide concentration is about 16 μM. In some aspects, the final cyclic dinucleotide concentration is about 17 μM. In some aspects, the final cyclic dinucleotide concentration is about 18 μM. In some aspects, the final cyclic dinucleotide concentration is about 19 μM. In some aspects, the final cyclic dinucleotide concentration is about 20 μM.

In some aspects, the final cyclic dinucleotide concentration is about 10 μM. In some aspects, the final cyclic dinucleotide concentration is about 20 μM. In some aspects, the final cyclic dinucleotide concentration is about 30 μM. In some aspects, the final cyclic dinucleotide concentration is about 40 μM. In some aspects, the final cyclic dinucleotide concentration is about 50 μM. In some aspects, the final cyclic dinucleotide concentration is about 60 μM. In some aspects, the final cyclic dinucleotide concentration is about 70 μM. In some aspects, the final cyclic dinucleotide concentration is about 80 μM. In some aspects, the final cyclic dinucleotide concentration is about 90 μM. In some aspects, the final cyclic dinucleotide concentration is about 100 μM. In some aspects, the final cyclic dinucleotide concentration is about 100 μM. In some aspects, the final cyclic dinucleotide concentration is about 200 μM. In some aspects, the final cyclic dinucleotide concentration is about 300 μM. In some aspects, the final cyclic dinucleotide concentration is about 400 μM. In some aspects, the final cyclic dinucleotide concentration is about 500 μM. In some aspects, the final cyclic dinucleotide concentration is about 600 μM. In some aspects, the final cyclic dinucleotide concentration is about 700 μM. In some aspects, the final cyclic dinucleotide concentration is about 800 μM. In some aspects, the final cyclic dinucleotide concentration is about 900 μM. In some aspects, the final cyclic dinucleotide concentration is about 1 mM.

The methods of the present disclosure are also useful for preparing compositions with much greater potency as compared to a reference extracellular vesicle composition incubated with a CDN, e.g., STING agonist, that is not subjected to a chromatography process. In some aspects, the CDN, e.g., STING agonist, concentration in the reference composition is the same as the CDN, e.g., STING agonist, concentration in a composition of the present disclosure. In some aspects, the composition of the present disclosure has the agonist concentration, after chromatography, as a reference composition but much greater potency. In some aspects, a chromatography is used to remove free CDNs. In some aspects, a multimodal chromatography is used to remove free CDNs.

The methods of the present disclosure are related to control of the pH during the chromatography process to improve the potency of a cyclic dinucleotide. The methods of the present disclosure are related to control of the pH during the chromatography process to improve the retention of free CDNs on the chromatography column as compared to a reference separation. In some aspects, the chromatography is performed at a pH lower than about 7.6, lower than about 7.5, lower than about 7.4, lower than about 7.3, lower than about 7.2, lower than about 7.1, lower than about 7.0, lower than about 6.9, lower than about 6.8, lower than about 6.7, lower than about 6.6, or lower than about 6.5. In some aspects, the chromatography is performed at a pH of about 7.6, about 7.5, about 7.4, about 7.3, about 7.2, about 7.1, about 7.0, about 6.9, about 6.8, about 6.7, about 6.6, or about 6.5. In some aspects, the chromatography is performed at a pH of about 7.6. In some aspects, the chromatography is performed at a pH of about 7.4. In some aspects, the chromatography is performed at a pH of about 7.2. In some aspects, the chromatography is performed at a pH of about 7.1. In some aspects, the chromatography is performed at a pH of about 7.0. In some aspects, the chromatography is performed at a pH of about 6.9. In some aspects, the chromatography is performed at a pH of about 6.8.

IIB. Methods for Loading STING Agonists in EVs

Cyclic dinucleotides (CDNs) and/or STING agonists can be associated or encapsulated in EVs, e.g., exosomes, prior to the chromatography, via any appropriate technique known in the art. Such techniques include passive diffusion, electroporation, chemical or polymeric transfection, viral transduction, mechanical membrane disruption or mechanical shear, or any combination thereof. In some aspects, the STING agonist and an EV, e.g., exosome, are incubated in an appropriate buffer during encapsulation.

In some aspects, after using one or more of the loading techniques described herein, the percentage of EVs loaded with a CDN (e.g., STING agonist) is about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 75%, about 70%, about 65%, about 60%, about 55%, about 50%, about 45%, about 40%, about 35%, about 30%, about 25%, about 20%, or about 10%.

In one aspect, a CDN, e.g., STING agonist, is encapsulated by an EV, e.g., exosome, by passive diffusion. The CDN, e.g., STING agonist, and the EV, e.g., exosome, are mixed together and incubated for a time period sufficient for the CDN, e.g., STING agonist, to diffuse through the vesicle lipid bilayer, thereby becoming encapsulated in the EV, e.g., exosome. The CDN, e.g., STING agonist, and the EV, e.g., exosome, are incubated together for between about 1 to about 30 hours, about 2 to about 26 hours, about 4 to about 24 hours, about 6 to about 24 hours, about 8 to about 24 hours, about 10 to about 24 hours, about 12 to about 24 hours, about 14 to about 24 hours, about 16 to about 24 hours, about 18 to about 24 hours, about 20 to about 24 hours, about 22 to about 24 hours, or about 20 to about 30 hours. In some aspects, the CDN, e.g., STING agonist, and the EV, e.g., exosome, are incubated together for between about 1 to about 30 hours. In some aspects, the CDN, e.g., STING agonist, and the EV, e.g., exosome, are incubated together for between about 2 to about 26 hours. In some aspects, the CDN, e.g., STING agonist, and the EV, e.g., exosome, are incubated together for between about 4 to about 24 hours. In some aspects, the CDN, e.g., STING agonist, and the EV, e.g., exosome, are incubated together for between about 6 to about 24 hours. In some aspects, the CDN, e.g., STING agonist, and the EV, e.g., exosome, are incubated together for between about 8 to about 24 hours. In some aspects, the CDN, e.g., STING agonist, and the EV, e.g., exosome, are incubated together for between about 10 to about 24 hours. In some aspects, the CDN, e.g., STING agonist, and the EV, e.g., exosome, are incubated together for between about 12 to about 24 hours. In some aspects, the CDN, e.g., STING agonist, and the EV, e.g., exosome, are incubated together for between about 14 to about 24 hours. In some aspects, the CDN, e.g., STING agonist, and the EV, e.g., exosome, are incubated together for between about 16 to about 24 hours. In some aspects, the CDN, e.g., STING agonist, and the EV, e.g., exosome, are incubated together for between about 18 to about 24 hours. In some aspects, the CDN, e.g., STING agonist, and the EV, e.g., exosome, are incubated together for between about 20 to about 24 hours. In some aspects, the CDN, e.g., STING agonist, and the EV, e.g., exosome, are incubated together for between about 22 to about 24 hours. In some aspects, the CDN, e.g., STING agonist, and the EV, e.g., exosome, are incubated together for between about 20 to about 30 hours.

In some aspects, the CDN, e.g., STING agonist, and the EV, e.g., exosome, are incubated together for about 2 hours, 4 hours, 6, hours, 8, hours, 10, hours, 12 hours, 14 hours, 16 hours, 18 hours, 20 hours, 22 hours, 24 hours, 26 hours, or 30 hours. In some aspects, the CDN, e.g., STING agonist, and the EV, e.g., exosome, are incubated together for about 2 hours. In some aspects, the STING agonist (CDN) and the EV, e.g., exosome, are incubated together for about 2 hours. In some aspects, the STING agonist (CDN) and the EV, e.g., exosome, are incubated together for about 4 hours. In some aspects, the STING agonist (CDN) and the EV, e.g., exosome, are incubated together for about 6 hours. In some aspects, the STING agonist (CDN) and the EV, e.g., exosome, are incubated together for about 8 hours. In some aspects, the STING agonist (CDN) and the EV, e.g., exosome, are incubated together for about 10 hours. In some aspects, the STING agonist (CDN) and the EV, e.g., exosome, are incubated together for about 12 hours. In some aspects, the STING agonist (CDN) and the EV, e.g., exosome, are incubated together for about 14 hours. In some aspects, the STING agonist (CDN) and the EV, e.g., exosome, are incubated together for about 16 hours. In some aspects, the STING agonist (CDN) and the EV, e.g., exosome, are incubated together for about 18 hours. In some aspects, the STING agonist (CDN) and the EV, e.g., exosome, are incubated together for about 20 hours. In some aspects, the STING agonist (CDN) and the EV, e.g., exosome, are incubated together for about 22 hours. In some aspects, the STING agonist (CDN) and the EV, e.g., exosome, are incubated together for about 24 hours. In some aspects, the STING agonist (CDN) and the EV, e.g., exosome, are incubated together for about 26 hours. In some aspects, the STING agonist (CDN) and the EV, e.g., exosome, are incubated together for about 30 hours.

In some aspects, the buffer conditions of the solution of EVs, e.g., exosomes, are altered to increase or control encapsulation of the CDN, e.g., STING agonist. In one aspect, the buffer is a phosphate buffered saline (PBS) with sucrose. In some aspects, additional buffer modifications are also be used, such as shear protectants, viscosity modifiers, and/or solutes that affect vesicle structural properties. In some aspects, excipients are added to improve the efficiency of the STING agonist encapsulation such as membrane softening materials and molecular crowding agents. In some aspects, other modifications to the buffer include specific pH ranges and/or concentrations of salts, organic solvents, small molecules, detergents, zwitterions, amino acids, polymers, and/or any combination of the above including multiple concentrations.

The methods of the present disclosure also involve the modification of temperature during EV incubation with CDN, e.g., STING agonist. The temperature of the solution of EVs, e.g., exosomes, and CDN, e.g., STING agonist, during incubation encapsulation of the STING agonist. In some aspects, the temperature is room temperature. In some aspects, the temperature is between about 15 °C to about 90 °C, 15 °C to about 30 °C, 30 °C to about 50 °C, or 50 °C to about 90 °C. In some aspects, the temperature is about 15 °C, 20 °C, 25 °C, 30 °C, 35 °C, 37 °C, 40 °C, 45 °C, 50 °C, 55 °C, 60 °C, 65 °C, 70 °C, 75 °C, 80 °C, 8 5 °C, or 90 °C.

In some aspects, the temperature is about 15 °C. In some aspects, the temperature is about 20 °C. In some aspects, the temperature is about 25 °C. In some aspects, the temperature is about 30 °C. In some aspects, the temperature is about 35 °C. In some aspects, the temperature is about 40 °C. In some aspects, the temperature is about 45 °C. In some aspects, the temperature is about 50 °C. In some aspects, the temperature is about 55 °C. In some aspects, the temperature is about 60 °C. In some aspects, the temperature is about 65 °C. In some aspects, the temperature is about 70 °C. In some aspects, the temperature is about 75 °C. In some aspects, the temperature is about 80 °C. In some aspects, the temperature is about 85 °C. In some aspects, the temperature is about 15 °C. In some aspects, the temperature is about 90 °C.

In some aspects, the concentration of CDN, e.g., STING agonist, during the incubation of the agonist with the EVs, e.g., exosomes, ("loading concentration") is altered to improve encapsulation of the CDN, e.g., STING agonist. In some aspects, the loading concentration of the CDN, e.g., STING agonist, is at least 0.01-1 mM, at least 1-10 mM, at least 10-50 mM, or at least 50-100 mM. In some aspects, the loading concentration of the agonist is at least 0.01 mM, at least 0.02 mM, at least at least 0.03 mM, at least 0.04 mM, at least 0.05 mM, at least 0.06 mM, at least 0.07 mM, at least 0.08 mM, at least 0.09 mM, at least 0.1 mM, at least 0.2 mM, at least 0.3 mM, at least 0.4 mM, at least 0.5 mM, at least 0.6 mM, at least 0.7 mM, at least 0.8 mM, at least 0.9 mM, at least 1 mM, at least 2 mM, at least 3 mM, at least 4 mM, at least 5 mM, at least 6 mM, at least 7 mM, at least 8 mM, at least 9 mM, at least 10 mM, at least 15 mM, at least 20 mM, at least 30 mM, at least 35 mM, at least 40 mM, at least 45 mM, at least 50 mM, at least 55 mM, at least 60 mM, at least 65 mM, at least 70 mM, at least 75 mM, at least 80 mM, at least 85 mM, at least 90 mM, at least 95 mM, or at least 100 mM.

In some aspects, the loading concentration of the CDN, e.g., STING agonist, is at least 0.01 mM. In some aspects, the loading concentration of the CDN, e.g., STING agonist, is at least 0.02 mM. In some aspects, the loading concentration of the CDN, e.g., STING agonist, is at least 0.03 mM. In some aspects, the loading concentration of the CDN, e.g., STING agonist, is at least 0.04 mM. In some aspects, the loading concentration of the CDN, e.g., STING agonist, is at least 0.05 mM. In some aspects, the loading concentration of the CDN, e.g., STING agonist, is at least 0.06 mM. In some aspects, the loading concentration of the CDN, e.g., STING agonist, is at least 0.07 mM. In some aspects, the loading concentration of the CDN, e.g., STING agonist, is at least 0.08 mM. In some aspects, the loading concentration of the CDN, e.g., STING agonist, is at least 0.09 mM. In some aspects, the loading concentration of the CDN, e.g., STING agonist, is at least 0.1 mM. In some aspects, the loading concentration of the CDN, e.g., STING agonist, is at least 0.2 mM. In some aspects, the loading concentration of the CDN, e.g., STING agonist, is at least 0.3 mM. In some aspects, the loading concentration of the CDN, e.g., STING agonist, is at least 0.4 mM. In some aspects, the loading concentration of the CDN, e.g., STING agonist, is at least 0.5 mM. In some aspects, the loading concentration of the CDN, e.g., STING agonist, is at least 0.6 mM. In some aspects, the loading concentration of the CDN, e.g., STING agonist, is at least 0.7 mM. In some aspects, the loading concentration of the CDN, e.g., STING agonist, is at least 0.8 mM. In some aspects, the loading concentration of the CDN, e.g., STING agonist, is at least 0.9 mM. In some aspects, the loading concentration of the CDN, e.g., STING agonist, is at least 1 mM. In some aspects, the loading concentration of the CDN, e.g., STING agonist, is at least 2 mM. In some aspects, the loading concentration of the CDN, e.g., STING agonist, is at least 3 mM. In some aspects, the loading concentration of the CDN, e.g., STING agonist, is at least 4 mM. In some aspects, the loading concentration of the CDN, e.g., STING agonist, is at least 5 mM. In some aspects, the loading concentration of the CDN, e.g., STING agonist, is at least 6 mM. In some aspects, the loading concentration of the CDN, e.g., STING agonist, is at least 7 mM. In some aspects, the loading concentration of the CDN, e.g., STING agonist, is at least 8 mM. In some aspects, the loading concentration of the CDN, e.g., STING agonist, is at least 9 mM. In some aspects, the loading concentration of the CDN, e.g., STING agonist, is at least 10 mM. In some aspects, the loading concentration of the CDN, e.g., STING agonist, is at least 15 mM. In some aspects, the loading concentration of the CDN, e.g., STING agonist, is at least 20 mM. In some aspects, the loading concentration of the CDN, e.g., STING agonist, is at least 25 mM. In some aspects, the loading concentration of the CDN, e.g., STING agonist, is at least 30 mM. In some aspects, the loading concentration of the CDN, e.g., STING agonist, is at least 35 mM. In some aspects, the loading concentration of the CDN, e.g., STING agonist, is at least 40 mM. In some aspects, the loading concentration of the CDN, e.g., STING agonist, is at least 45 mM. In some aspects, the loading concentration of the CDN, e.g., STING agonist, is at least 50 mM. In some aspects, the loading concentration of the CDN, e.g., STING agonist, is at least 55 mM. In some aspects, the loading concentration of the CDN, e.g., STING agonist, is at least 60 mM. In some aspects, the loading concentration of the CDN, e.g., STING agonist, is at least 65 mM. In some aspects, the loading concentration of the CDN, e.g., STING agonist, is at least 70 mM. In some aspects, the loading concentration of the CDN, e.g., STING agonist, is at least 75 mM. In some aspects, the loading concentration of the CDN, e.g., STING agonist, is at least 80 mM. In some aspects, the loading concentration of the CDN, e.g., STING agonist, is at least 85 mM. In some aspects, the loading concentration of the CDN, e.g., STING agonist, is at least 90 mM. In some aspects, the loading concentration of the CDN, e.g., STING agonist, is at least 95 mM. In some aspects, the loading concentration of the CDN, e.g., STING agonist, is at least 100 mM.

In some aspects, the CDNs, e.g., STING agonists, are incubated in the mixture at a concentration of at least about 500 μM, at least about 600 μM, at least about 700 μM, at least about 800 μM, at least about 900 μM, at least about 1000 μM, at least about 1100 μM, at least about 1200 μM, at least about 1300 μM, at least about 1400 μM, at least about 1500 μM, at least about 1600 μM, at least about 1700 μM, at least about 1800 μM, at least about 1900 μM, or at least about 2000 μM. In some aspects, the CDNs, e.g., STING agonists, are incubated in the mixture at a concentration of at least about 2100 μM, at least about 2200 μM, at least about 2300 μM, at least about 2400 μM, at least about 2500 μM, at least about 2600 μM, at least about 2700 μM, at least about 2800 μM, at least about 2900 μM, at least about 3000 μM, at least about 3100 μM, at least about 3200 μM, at least about 3300 μM, at least about 3400 μM, at least about 3500 μM, at least about 3600 μM, at least about 3700 μM, at least about 3800 μM, at least about 3900 μM, or at least about 4000 μM.

In some aspects, the CDNs, e.g., STING agonists, are incubated in the mixture at a concentration of at least about 500 μM. In some aspects, the CDNs, e.g., STING agonists, are incubated in the mixture at a concentration of at least about 600 μM. In some aspects, the CDNs, e.g., STING agonists, are incubated in the mixture at a concentration of at least about 700 μM. In some aspects, the CDNs, e.g., STING agonists, are incubated in the mixture at a concentration of at least about 800 μM. In some aspects, the CDNs, e.g., STING agonists, are incubated in the mixture at a concentration of at least about 900 μM. In some aspects, the CDNs, e.g., STING agonists, are incubated in the mixture at a concentration of at least about 1000 μM. In some aspects, the CDNs, e.g., STING agonists, are incubated in the mixture at a concentration of at least about 1100 μM. In some aspects, the CDNs, e.g., STING agonists, are incubated in the mixture at a concentration of at least about 1200 μM. In some aspects, the CDNs, e.g., STING agonists, are incubated in the mixture at a concentration of at least about 1300 μM. In some aspects, the CDNs, e.g., STING agonists, are incubated in the mixture at a concentration of at least about 1400 μM. In some aspects, the CDNs, e.g., STING agonists, are incubated in the mixture at a concentration of at least about 1500 μM. In some aspects, the CDNs, e.g., STING agonists, are incubated in the mixture at a concentration of at least about 1600 μM. In some aspects, the CDNs, e.g., STING agonists, are incubated in the mixture at a concentration of at least about 1700 μM. In some aspects, the CDNs, e.g., STING agonists, are incubated in the mixture at a concentration of at least about 1800 μM. In some aspects, the CDNs, e.g., STING agonists, are incubated in the mixture at a concentration of at least about 1900 μM. In some aspects, the CDNs, e.g., STING agonists, are incubated in the mixture at a concentration of at least about 2000 μM. In some aspects, the CDNs, e.g., STING agonists, are incubated in the mixture at a concentration of at least about 2100 μM. In some aspects, the CDNs, e.g., STING agonists, are incubated in the mixture at a concentration of at least about 2200 μM. In some aspects, the CDNs, e.g., STING agonists, are incubated in the mixture at a concentration of at least about 2300 μM. In some aspects, the CDNs, e.g., STING agonists, are incubated in the mixture at a concentration of at least about 2400 μM. In some aspects, the CDNs, e.g., STING agonists, are incubated in the mixture at a concentration of at least about 2500 μM. In some aspects, the CDNs, e.g., STING agonists, are incubated in the mixture at a concentration of at least about 2600 μM. In some aspects, the CDNs, e.g., STING agonists, are incubated in the mixture at a concentration of at least about 2700 μM. In some aspects, the CDNs, e.g., STING agonists, are incubated in the mixture at a concentration of at least about 2800 μM. In some aspects, the CDNs, e.g., STING agonists, are incubated in the mixture at a concentration of at least about 2900 μM. In some aspects, the CDNs, e.g., STING agonists, are incubated in the mixture at a concentration of at least about 3000 μM. In some aspects, the CDNs, e.g., STING agonists, are incubated in the mixture at a concentration of at least about 3100 μM. In some aspects, the CDNs, e.g., STING agonists, are incubated in the mixture at a concentration of at least about 3200 μM. In some aspects, the CDNs, e.g., STING agonists, are incubated in the mixture at a concentration of at least about 3300 μM. In some aspects, the CDNs, e.g., STING agonists, are incubated in the mixture at a concentration of at least about 3400 μM. In some aspects, the CDNs, e.g., STING agonists, are incubated in the mixture at a concentration of at least about 3500 μM. In some aspects, the CDNs, e.g., STING agonists, are incubated in the mixture at a concentration of at least about 3600 μM. In some aspects, the CDNs, e.g., STING agonists, are incubated in the mixture at a concentration of at least about 3700 μM. In some aspects, the CDNs, e.g., STING agonists, are incubated in the mixture at a concentration of at least about 3800 μM. In some aspects, the CDNs, e.g., STING agonists, are incubated in the mixture at a concentration of at least about 3900 μM. In some aspects, the CDNs, e.g., STING agonists, are incubated in the mixture at a concentration of at least about 4000 μM.

In some aspects, the CDNs, e.g., STING agonists are incubated in the mixture between about 500 μM and about 100 mM, between about 500 μM and about 90 mM, between about 500 μM and about 80 mM, between about 500 μM and about 70 mM, between about 500 μM and about 60 mM, between about 500 μM and about 50 mM, between about 500 μM and about 40 mM, between about 500 μM and about 30 mM, between about 500 μM and about 20 mM, between about 500 μM and about 10 mM, or between about 500 μM and about 1 mM. In some aspects, the CDNs are incubated in the mixture between about 500 μM and about 10 mM, between about 500 μM and about 9 mM, between about 500 μM and about 8 mM, between about 500 μM and about 7 mM, between about 500 μM and about 6 mM, between about 500 μM and about 5 mM, between about 500 μM and about 4 mM, between about 500 μM and about 3 mM, between about 500 μM and about 2 mM, or between about 500 μM and about 1 mM.

In some aspects, the CDNs, e.g., STING agonists are incubated in the mixture between about 500 μM and about 100 mM. In some aspects, the CDNs, e.g., STING agonists are incubated in the mixture between about 500 μM and about 90 mM. In some aspects, the CDNs, e.g., STING agonists are incubated in the mixture between about 500 μM and about 80 mM. In some aspects, the CDNs, e.g., STING agonists are incubated in the mixture between about 500 μM and about 70 mM. In some aspects, the CDNs, e.g., STING agonists are incubated in the mixture between about 500 μM and about 60 mM. In some aspects, the CDNs, e.g., STING agonists are incubated in the mixture between about 500 μM and about 50 mM. In some aspects, the CDNs, e.g., STING agonists are incubated in the mixture between about 500 μM and about 40 mM. In some aspects, the CDNs, e.g., STING agonists are incubated in the mixture between about 500 μM and about 30 mM. In some aspects, the CDNs, e.g., STING agonists are incubated in the mixture between about 500 μM and about 20 mM. In some aspects, the CDNs, e.g., STING agonists are incubated in the mixture between about 500 μM and about 10 mM. In some aspects, the CDNs, e.g., STING agonists are incubated in the mixture between about 500 μM and about 9 mM. In some aspects, the CDNs, e.g., STING agonists are incubated in the mixture between about 500 μM and about 8 mM. In some aspects, the CDNs, e.g., STING agonists are incubated in the mixture between about 500 μM and about 7 mM. In some aspects, the CDNs, e.g., STING agonists are incubated in the mixture between about 500 μM and about 6 mM. In some aspects, the CDNs, e.g., STING agonists are incubated in the mixture between about 500 μM and about 5 mM. In some aspects, the CDNs, e.g., STING agonists are incubated in the mixture between about 500 μM and about 4 mM. In some aspects, the CDNs, e.g., STING agonists are incubated in the mixture between about 500 μM and about 3 mM. In some aspects, the CDNs, e.g., STING agonists are incubated in the mixture between about 500 μM and about 2 mM. In some aspects, the CDNs, e.g., STING agonists are incubated in the mixture between about 500 μM and about 1 mM.

The methods of the present disclosure are useful for improving or maintaining the potency of CDNs, e.g., STING agonists after chromatography. In some aspects, the chromatography is a multimodal chromatography. In some aspects, after the multimodal chromatography, the CDNs are at a final concentration of from about 0.5 μM to about 10 μM. In some aspects, after the multimodal chromatography, the CDNs are at a final concentration of between about 1 μM and about 10 μM, between about 2 μM and about 10 μM, between about 2 μM and about 9 μM, between about 3 μM and about 9 μM, between about 3 μM and about 8 μM, between about 4 μM and about 8 μM, between about 4 μM and about 7 μM, or between about 4 μM and about 6 μM. In some aspects, the final cyclic dinucleotide concentration is from about 0.5 μM to about 10 μM. In some aspects, the final cyclic dinucleotide concentration is about 1 μM. In some aspects, the final cyclic dinucleotide concentration is about 2 μM. In some aspects, the final cyclic dinucleotide concentration is about 3 μM. In some aspects, the final cyclic dinucleotide concentration is about 4 μM. In some aspects, the final cyclic dinucleotide concentration is about 5 μM. In some aspects, the final cyclic dinucleotide concentration is about 6 μM. In some aspects, the final cyclic dinucleotide concentration is about 7 μM. In some aspects, the final cyclic dinucleotide concentration is about 8 μM. In some aspects, the final cyclic dinucleotide concentration is about 9 μM. In some aspects, the final cyclic dinucleotide concentration is about 10 μM. In some aspects, the final cyclic dinucleotide concentration is about 11 μM. In some aspects, the final cyclic dinucleotide concentration is about 12 μM. In some aspects, the final cyclic dinucleotide concentration is about 13 μM. In some aspects, the final cyclic dinucleotide concentration is about 14 μM. In some aspects, the final cyclic dinucleotide concentration is about 15 μM. In some aspects, the final cyclic dinucleotide concentration is about 16 μM. In some aspects, the final cyclic dinucleotide concentration is about 17 μM. In some aspects, the final cyclic dinucleotide concentration is about 18 μM. In some aspects, the final cyclic dinucleotide concentration is about 19 μM. In some aspects, the final cyclic dinucleotide concentration is about 20 μM.

In some aspects, the final cyclic dinucleotide concentration is about 10 μM. In some aspects, the final cyclic dinucleotide concentration is about 20 μM. In some aspects, the final cyclic dinucleotide concentration is about 30 μM. In some aspects, the final cyclic dinucleotide concentration is about 40 μM. In some aspects, the final cyclic dinucleotide concentration is about 50 μM. In some aspects, the final cyclic dinucleotide concentration is about 60 μM. In some aspects, the final cyclic dinucleotide concentration is about 70 μM. In some aspects, the final cyclic dinucleotide concentration is about 80 μM. In some aspects, the final cyclic dinucleotide concentration is about 90 μM. In some aspects, the final cyclic dinucleotide concentration is about 100 μM. In some aspects, the final cyclic dinucleotide concentration is about 100 μM. In some aspects, the final cyclic dinucleotide concentration is about 200 μM. In some aspects, the final cyclic dinucleotide concentration is about 300 μM. In some aspects, the final cyclic dinucleotide concentration is about 400 μM. In some aspects, the final cyclic dinucleotide concentration is about 500 μM. In some aspects, the final cyclic dinucleotide concentration is about 600 μM. In some aspects, the final cyclic dinucleotide concentration is about 700 μM. In some aspects, the final cyclic dinucleotide concentration is about 800 μM. In some aspects, the final cyclic dinucleotide concentration is about 900 μM. In some aspects, the final cyclic dinucleotide concentration is about 1 mM.

The methods of the present disclosure are also useful for preparing compositions with much greater potency as compared to a reference extracellular vesicle composition incubated with a CDN, e.g., STING agonist, that is not subjected to a chromatography process. In some aspects, the CDN, e.g., STING agonist, concentration in the reference composition is the same as the CDN, e.g., STING agonist, concentration in a composition of the present disclosure. In some aspects, the composition of the present disclosure has the same or similar CDN, e.g., STING agonist, concentration, after chromatography, as a reference composition but much greater potency. In some aspects, a chromatography is used to remove free CDNs. In some aspects, a multimodal chromatography is used to remove free CDNs.

In some aspects, after the chromatography to remove free CDNs, the percentage of free CDNs present in the composition is less than about 1 percent, less than about 5 percent, less than about 10 percent, less than about 15 percent, less than about 20 percent, less than about 25 percent, less than about 30 percent, less than about 35 percent, less than about 40 percent, less than about 45 percent, less than about 50 percent, less than about 55 percent, less than about 60 percent, less than about 65 percent, less than about 70 percent, less than about 75 percent, less than about 80 percent, less than about 85 percent, less than about 90 percent, or less than about 55 percent.

The methods of the present disclosure are related to control of the pH during the chromatography process to improve the potency of a cyclic dinucleotide. The methods of the present disclosure are related to control of the pH during the chromatography process to improve the retention of free CDNs on the chromatography column as compared to a reference separation. In some aspects, the chromatography is performed at a pH lower than about 7.6, lower than about 7.5, lower than about 7.4, lower than about 7.3, lower than about 7.2, lower than about 7.1, lower than about 7.0, lower than about 6.9, lower than about 6.8, lower than about 6.7, lower than about 6.6, or lower than about 6.5. In some aspects, the chromatography is performed at a pH of about 7.6, about 7.5, about 7.4, about 7.3, about 7.2, about 7.1, about 7.0, about 6.9, about 6.8, about 6.7, about 6.6, or about 6.5. In some aspects, the chromatography is performed at a pH of about 7.6. In some aspects, the chromatography is performed at a pH of about 7.4. In some aspects, the chromatography is performed at a pH of about 7.2. In some aspects, the chromatography is performed at a pH of about 7.1. In some aspects, the chromatography is performed at a pH of about 7.0. In some aspects, the chromatography is performed at a pH of about 6.9. In some aspects, the chromatography is performed at a pH of about 6.8.

The methods of the present disclosure can be used with various concentrations of EV. In some aspects, the number of extracellular particles incubated with the CDNs, e.g., STING agonist is altered to improve encapsulation of the CDNs, e.g., STING agonist. In some aspects, the number of purified EV, e.g., exosome, particles is between at least about $10^6$ to at least about $10^{20}$ total particles of purified vesicles. In some aspects, the number of purified particles is between about $10^8$ to about $10^{18}$, about $10^{10}$ to about $10^{16}$, about $10^8$ to about $10^{14}$, or about $10^{10}$ to about $10^{12}$ total particles of purified vesicles. In some aspects, the number of purified particles is at least about $10^6$, at least about $10^8$, at least about $10^{10}$, at least about $10^{12}$, at least about $10^{14}$, at least about $10^{16}$, at least about $10^{18}$, or at least about $10^{20}$ total particles of purified vesicles.

In some aspects, the EVs are incubated in the mixture at a loading concentration of from about $1.0\times10^{12}$ particles/mL to about $5.0\times10^{13}$ particles/mL. In some aspects, the EVs are incubated in the mixture at a loading concentration of from about $1.0\times10^{12}$ particles/mL to about $4.0\times10^{13}$ particles/mL. In some aspects, the EVs are incubated in the mixture at a loading concentration of from about $1.0\times10^{12}$ particles/mL to about $3.0\times10^{13}$ particles/mL. In some aspects, the EVs are incubated in the mixture at a loading concentration of from about $1.0\times10^{12}$ particles/mL to about $2.0\times10^{13}$ particles/mL. In some aspects, the EVs are incubated in the mixture at a loading concentration of from about $1.0\times10^{12}$ particles/mL to about $1.0\times10^{13}$ particles/mL.

In some aspects, the EVs are incubated in the mixture at a loading concentration of at least about $1.00\times10^{12}$ particles/mL, at least about $1.50\times10^{12}$ particles/mL, at least about $2.00\times10^{12}$ particles/mL, at least about $2.50\times10^{12}$ particles/mL at least about $3.00\times10^{12}$ particles/mL, at least about $3.50\times10^{12}$ particles/mL, at least about $4.00\times10^{12}$ particles/mL, at least about $4.50\times10^{12}$ particles/mL, at least about $5.0\times10^{12}$ particles/mL, at least about $5.50\times10^{12}$ particles/mL, at least about $6.00\times10^{12}$ particles/mL, at least about $6.50\times10^{12}$ particles/mL, at least about $7.00\times10^{12}$ particles/mL at least about $7.50\times10^{12}$ particles/mL, at least about $8.00\times10^{12}$ particles/mL, at least about $8.50\times10^{12}$ particles/mL, at least about $9.00\times10^{12}$ particles/mL, at least about $9.50\times10^{12}$ particles/mL, at least about $1.00\times10^{13}$ particles/mL, at least about $1.1\times10^{13}$ particles/mL, at least about $1.2\times10^{13}$ particles/mL, at least about $1.3\times10^{13}$ particles/mL, at least about $1.4\times10^{13}$ particles/mL, or at least about $1.5\times10^{13}$ particles/mL.

In some aspects, the EVs are incubated in the mixture at a loading concentration of at least about $1.00\times10^{12}$ particles/mL. In some aspects, the EVs are incubated in the mixture at a loading concentration of at least about $1.00\times10^{12}$ particles/mL. In some aspects, the EVs are incubated in the mixture at a loading concentration of at least about $1.00\times10^{12}$ particles/mL.

In some aspects, the EVs are incubated in the mixture at a loading concentration of at least about $1.00\times10^{12}$ particles/mL. In some aspects, the EVs are incubated in the mixture at a loading concentration of at least about $1.50\times10^{12}$ particles/mL. In some aspects, the EVs are incubated in the mixture at a loading concentration of at least about $2.00\times10^{12}$ particles/mL. In some aspects, the EVs are incubated in the mixture at a loading concentration of at least about $2.50\times10^{12}$ particles/mL. In some aspects, the EVs are incubated in the mixture at a loading concentration of at least about $3.00\times10^{12}$ particles/mL. In some aspects, the EVs are incubated in the mixture at a loading concentration of at least about $3.50\times10^{12}$ particles/mL. In some aspects, the EVs are incubated in the mixture at a loading concentration of at least about $4.00\times10^{12}$ particles/mL. In some aspects, the EVs are incubated in the mixture at a loading concentration of at least about $4.50\times10^{12}$ particles/mL. In some aspects, the EVs are incubated in the mixture at a loading concentration of at least about $5.00\times10^{12}$ particles/mL. In some aspects, the EVs are incubated in the mixture at a loading concentration of at least about $5.50\times10^{12}$ particles/mL. In some aspects, the EVs are incubated in the mixture at a loading concentration of at least about $6.00\times10^{12}$ particles/mL. In some aspects, the EVs are incubated in the mixture at a loading concentration of at least about $6.50\times10^{12}$ particles/mL. In some aspects, the EVs are incubated in the mixture at a loading concentration of at least about $7.00\times10^{12}$ particles/mL. In some aspects, the EVs are incubated in the mixture at a loading concentration of at least about $7.50\times10^{12}$ particles/mL. In some aspects, the EVs are incubated in the mixture at a loading concentration of at least about $8.00\times10^{12}$ particles/mL. In some aspects, the EVs are incubated in the mixture at a loading concentration of at least about $8.50\times10^{12}$ particles/mL. In some aspects, the EVs are incubated in the mixture at a loading concentration of at least about $9.00\times10^{12}$ particles/mL. In some aspects, the EVs are incubated in the mixture at a loading concentration of at least about $9.50\times10^{12}$ particles/mL. In some aspects, the EVs are incubated in the mixture at a loading concentration of at least about $1.00\times10^{13}$ particles/mL. In some aspects, the EVs are incubated in the mixture at a loading concentration of at least about $1.10\times10^{13}$ particles/mL. In some aspects, the EVs are incubated in the mixture at a loading concentration of at least about $1.20\times10^{13}$ particles/mL. In some aspects, the EVs are incubated in the mixture at a loading concentration of at least about $1.30\times10^{13}$ particles/mL. In some aspects, the EVs are incubated in the mixture at a loading concentration of at least about $1.40\times10^{13}$ particles/mL. In some aspects, the EVs are incubated in the mixture at a loading concentration of at least about $1.50\times10^{13}$ particles/mL. In some aspects, the EVs are incubated in the mixture at a loading concentration of at least about $1.60\times10^{13}$ particles/mL. In some aspects, the EVs are incubated in the mixture at a loading concentration of at least about $1.70\times10^{13}$ particles/mL. In some aspects, the EVs are incubated in the mixture at a loading concentration of at least about $1.80\times10^{13}$ particles/mL. In some aspects, the EVs are incubated in the mixture at a loading concentration of at least about $1.90\times10^{13}$ particles/mL. In some aspects, the EVs are incubated in the mixture at a loading concentration of at least about $2.00\times10^{13}$ particles/mL.

In some aspects, the EVs are incubated in the mixture at a loading concentration of at least about $2.50\times10^{13}$ particles/mL. In some aspects, the EVs are incubated in the mixture at a loading concentration of at least about $3.00\times10^{13}$ particles/mL. In some aspects, the EVs are incubated in the mixture at a loading concentration of at least about $3.50\times10^{13}$ particles/mL. In some aspects, the EVs are incubated in the mixture at a loading concentration of at least about $4.00\times10^{13}$ particles/mL. In some aspects, the EVs are incubated in the mixture at a loading concentration of at least about $4.50\times10^{13}$ particles/mL. In some aspects, the EVs are incubated in the mixture at a loading concentration of at least about $5.00\times10^{13}$ particles/mL. In some aspects, the EVs are incubated in the mixture at a loading concentration of at least about $5.50\times10^{13}$ particles/mL. In some aspects, the EVs are incubated in the mixture at a loading concentration of at least about $6.00\times10^{13}$ particles/mL. In some aspects, the EVs are incubated in the mixture at a loading concentration of at least about $6.50\times10^{13}$ particles/mL. In some aspects, the EVs are incubated in the mixture at a loading concentration of at least about $7.00\times10^{13}$ particles/mL. In some aspects, the EVs are incubated in the mixture at a loading concentration of at least about $7.50\times10^{13}$ particles/mL. In some aspects, the EVs are incubated in the mixture at a loading concentration of at least about $8.00\times10^{13}$ particles/mL. In some aspects, the EVs are incubated in the mixture at a loading concentration of at least about $8.50\times10^{13}$ particles/mL. In some aspects, the EVs are incubated in the mixture at a loading concentration of at least about $9.00\times10^{13}$ particles/mL. In some aspects, the EVs are incubated in the mixture at a loading concentration of at least about $9.50\times10^{13}$ particles/mL. In some aspects, the EVs are incubated in the mixture at a loading concentration of at least about $1.00\times10^{14}$ particles/mL.

III. Extracellular Vesicles, e.g., Exosomes

As described supra, EVs, e.g., exosomes, described herein are EVs with a diameter between about 20-300 nm. In certain aspects, an EV, e.g., exosome, of the present disclosure has a diameter between about 20-80 nm, 20-100 nm, 20-200 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm. The size of the EV, e.g., exosome, described herein can be measured according to methods described, infra.

In some aspects, an EV, e.g., exosome, of the present disclosure comprises a bi-lipid membrane ("EV, e.g., exosome, membrane"), comprising an interior surface and an exterior surface. In certain aspects, the interior surface faces the inner core (i.e., lumen) of the EV, e.g., exosome. In certain aspects, the exterior surface can be in contact with the endosome, the multivesicular bodies, or the membrane/cytoplasm of a producer cell or a target cell In some aspects, the EV, e.g., exosome, membrane comprises lipids and fatty acids. In some aspects, the EV, e.g., exosome, membrane comprises phospholipids, glycolipids, fatty acids, sphingolipids, phosphoglycerides, sterols, cholesterols, and phosphatidylserines.

In some aspects, the EV, e.g., exosome, membrane comprises an inner leaflet and an outer leaflet. The composition of the inner and outer leaflet can be determined by transbilayer distribution assays known in the art, see, e.g., Kuypers et al., Biohim Biophys Acta 1985 819:170. In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, EVs of the present disclosure comprise a membrane modified in its composition. For example, their membrane compositions can be modified by changing the protein, lipid, or glycan content of the membrane.

In some aspects, the exosome further comprises an exosome that expresses a ligand, a cytokine, or an antibody. In one aspect, the ligand comprises CD40L, OX40L, or CD27L. In another aspect, the cytokine comprises IL-7, IL-12 or IL-15. In one aspect, the antibody comprises an antagonistic antibody or an agonistic antibody. In some aspects, the cytokine comprises IL-7. In some aspects, the cytokine comprises IL-12. In some aspects, the cytokine comprises IL-15.

In some aspects, the EV further comprises a protein that binds to or enzymatically reacts with the STING agonist. In certain aspects, the EV further comprises a ligand, a cytokine, or an antibody. In some aspects, the ligand comprises CD40L, OX40L, and/or CD27L. In some aspects, the cytokine comprises IL-7, IL-12, and/or IL-15. In certain aspects, the antibody comprises an antagonistic antibody and/or an agonistic antibody. In some aspects, the cytokine comprises IL-7. In some aspects, the cytokine comprises IL-12. In some aspects, the cytokine comprises IL-15.

In some aspects, Scaffold X and IL-12 are attached to the luminal surface and on the exterior surface of the EV, e.g., exosome, at the same time. For example, the PTGFRN polypeptide can be used to link an IL-12 inside the lumen (e.g., on the luminal surface) in addition to the exterior surface of the EV, e.g., exosome. Therefore, in certain aspects, Scaffold X can be used for dual purposes, e.g., an IL-12 on the luminal surface and an IL-12 on the exterior surface of the EV, e.g., exosome. In some aspects, Scaffold X is a scaffold protein that is capable of anchoring the IL-12 on the luminal surface of the EV and/or on the exterior surface of the EV.

IIIB. Linker

The EVs of the present disclosure can comprises one or more linkers that link the STING agonist to EVs or to a scaffold moiety, e.g., Scaffold X on the exterior surface of the EVs. In some aspects, the STING agonist is linked to the EVs directly or in a scaffold moiety on the EVs by a linker. The linker can be any chemical moiety known in the art.

In some aspects, the term "linker" refers to a peptide or polypeptide sequence (e.g., a synthetic peptide or polypeptide sequence) or to a non-polypeptide. In some aspects, two or more linkers can be linked in tandem. Generally, linkers provide flexibility or prevent/ameliorate steric hindrances. Linkers are not typically cleaved; however in certain aspects, such cleavage can be desirable. Accordingly, in some aspects a linker can comprise one or more protease-cleavable sites, which can be located within the sequence of the linker or flanking the linker at either end of the linker sequence.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion).

In some aspects, linkers are susceptible to cleavage ("cleavable linker") thereby facilitating release of the STING Agonist or other payloads. In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof. In some aspects, the linker comprises a non-cleavable linker.

IIIC. STING Agonists

STING agonists used in this disclosure can be cyclic dinucleotides (CDNs) or non-cyclic dinucleotide agonists. Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, are known to stimulate or enhance an immune or inflammation response in a patient. In some aspects, the CDNs have 2'2', 2'3', 2'5', 3'3', or 3'5' bonds linking the cyclic dinucleotides, or any combination thereof.

In some aspects, cyclic purine dinucleotides are modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. In some aspects, the cyclic dinucleotides are modified analogues. In some aspects, suitable modification known in the art are used, including, but not limited to, phosphorothioate, biphosphorothioate, fluorinate, and difluorinate modifications.

In some aspects, non cyclic dinucleotide agonists are used, such as 5,6-Dimethylxanthenone-4-acetic acid (DMXAA), or any other non-cyclic dinucleotide agonist known in the art.

In some aspects, any STING agonist is used. Among the STING agonists are DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, c-di-AMP, 2'3'-c-di-AMP, 2'3'-c-di-AM(PS)2, c-di-GMP, 2'3'-c-di-GMP, c-di-IMP, c-di-UMP or any combination thereof. In a preferred aspect, the STING agonist is 3'3'-cAIMPdFSH, alternatively named 3-3 cAIMPdFSH. In some aspects, Additional STING agonists known in the art are used.

In some aspects, the STING agonist useful for the present disclosure comprises a compound having the following formula:

Formula 1

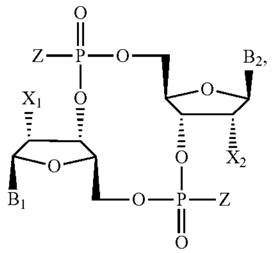

Formula 2

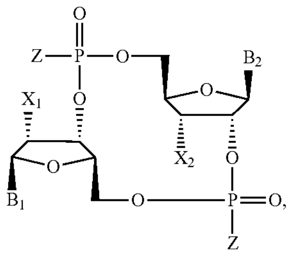

or

Formula 3

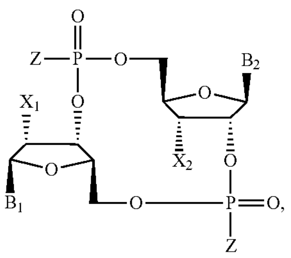

wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

Bi and B2 are bases chosen from:

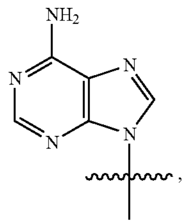

Adenine

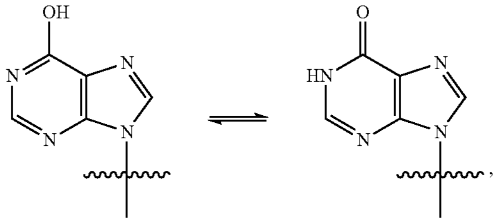

or

Hypoxanthine

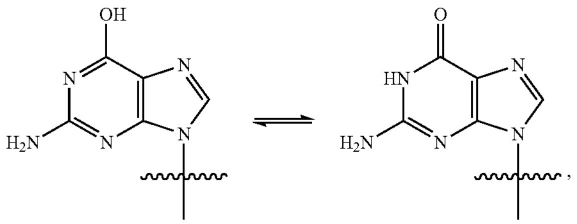

Guanine

With proviso that:

in Formula (I): $X_1$ and $X_2$ are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH. See WO 2016/096174, the content of which is incorporated herein by reference in its entirety.

In some aspects, the STING agonist useful for the present disclosure comprises:
ADU-S100
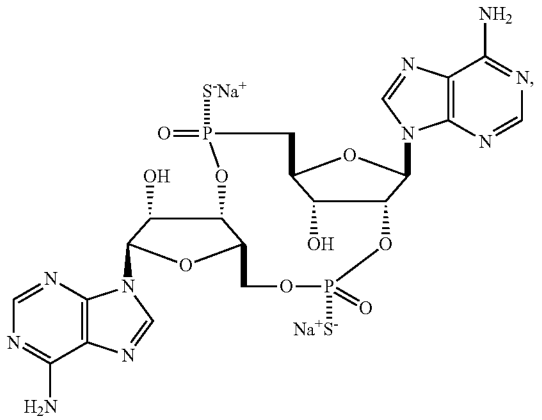
CL-592
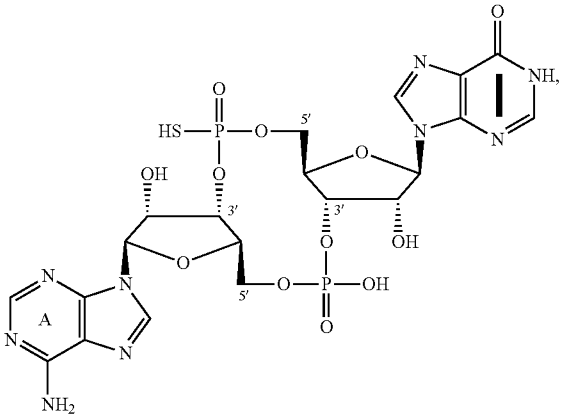
cAIMP
CL-656
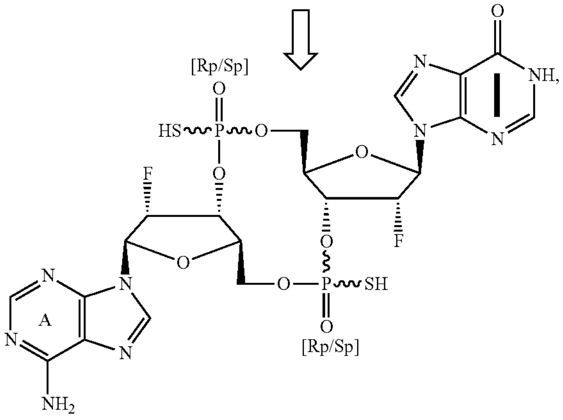
c[2-FdAMP(S)-2FdIMP(S)]
-continued
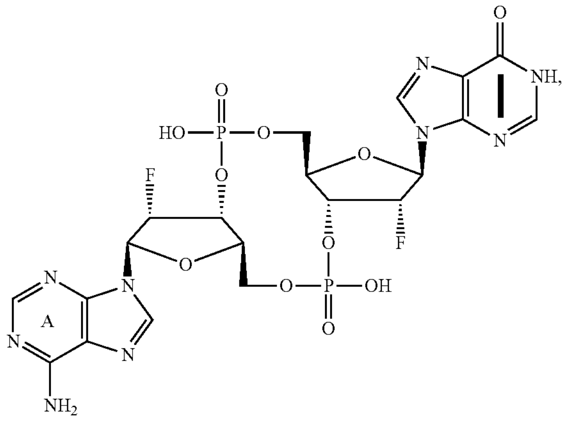
c[2-FdAMP(S)-2FdIMP]
CL-797
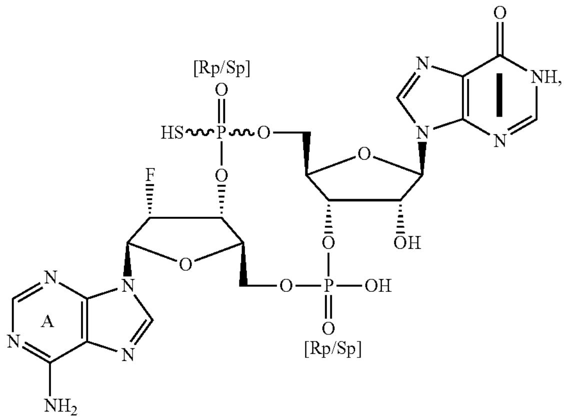
c[2FdAMP(S)-IMP]
CL-655
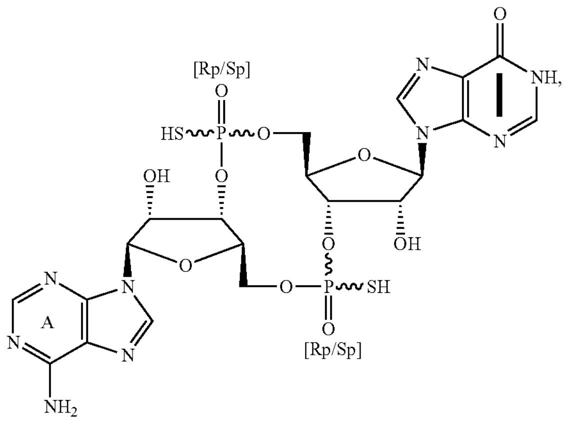
c[AMP(S)-IMP(S)]

-continued
CL-659
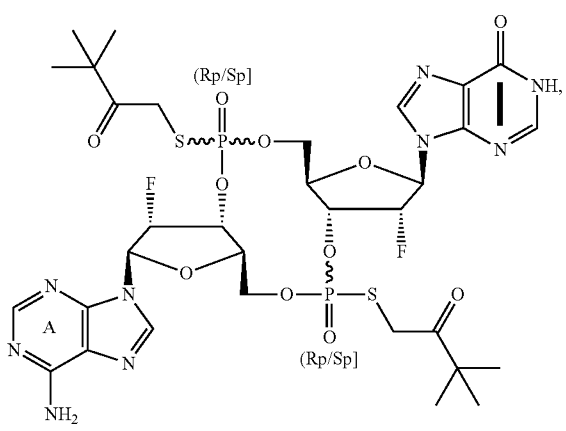
c-[2′FdAMP(S)-2FdIMP(S)](POM)$_2$
a pharmaceutically acceptable salt thereof. See WO 2016/096174A1.
In other aspects, the STING agonist useful for the present disclosure comprises a compound having the following formula:
CL606
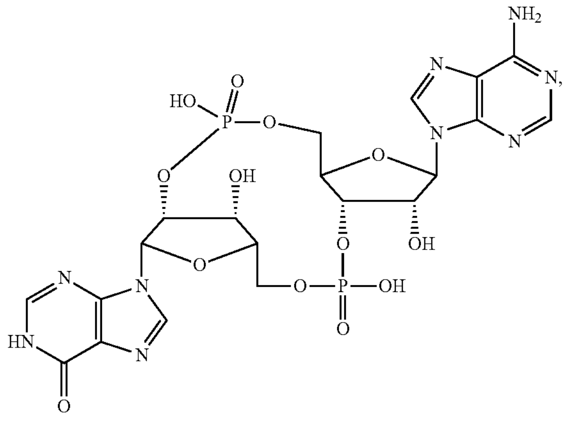
(3′,2′)c-AIMP
CL611
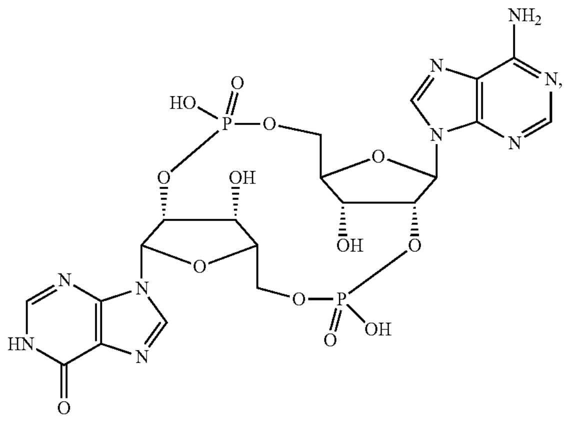
(2′,2′)c-AIMP
-continued
CL602
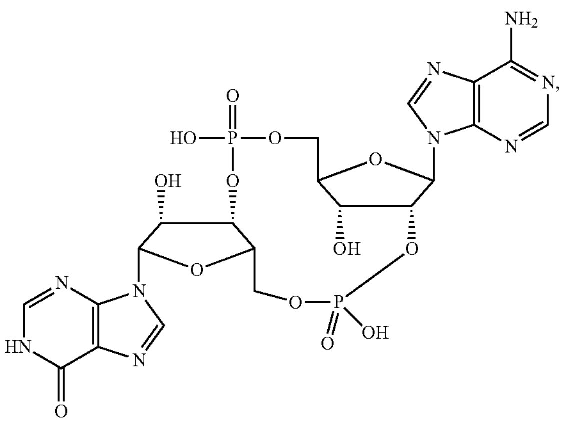
(2′,3′)c-AIMP
CL655
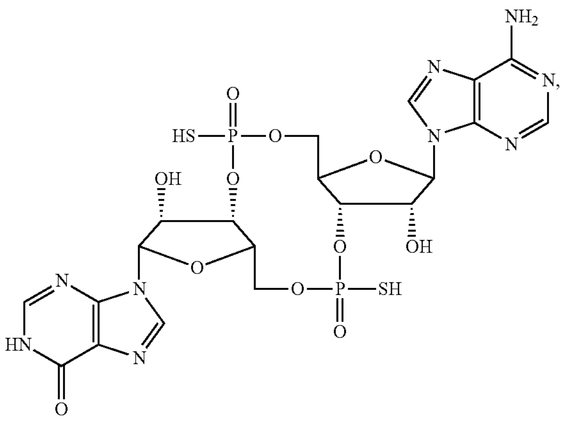
c-AIMP(S)
CL604
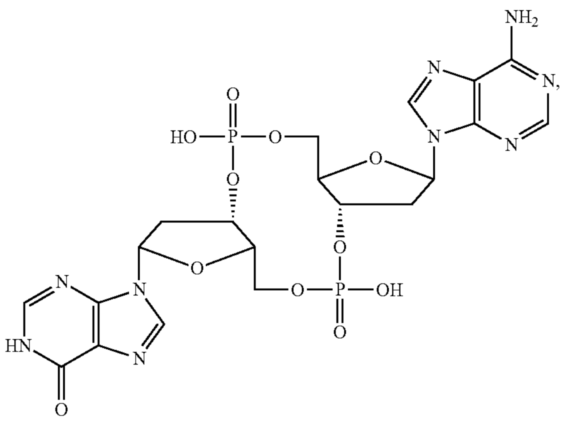
c-(dAMP-dIMP)

-continued
CL609
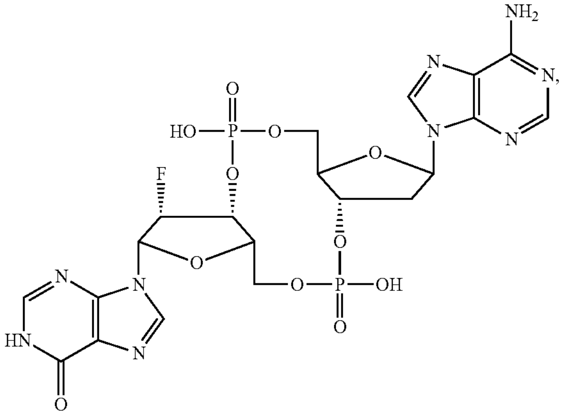
c-(dAMP-2′FdIMP)
CL614
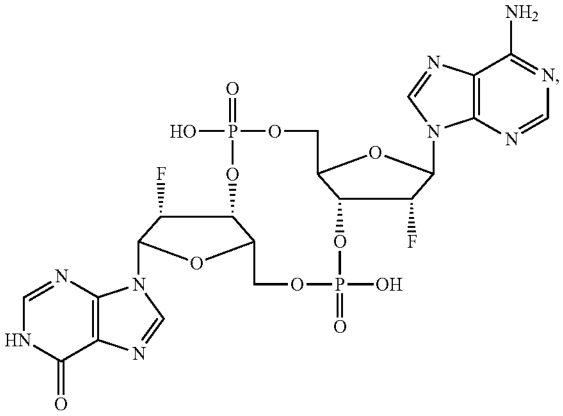
c-(2-FdAMP-2′FdIMP)
CL656
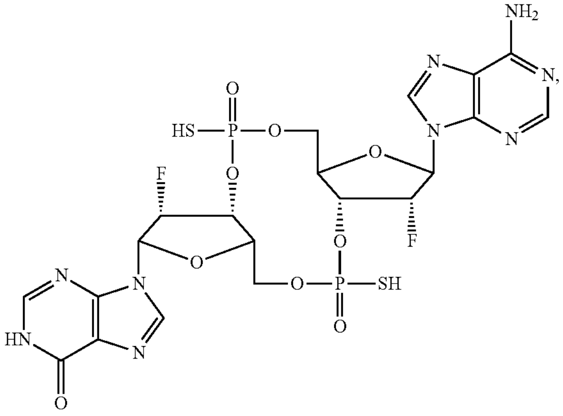
c-[2′-FdAMP(S)-2′FdIMP(S)]
-continued
CL647
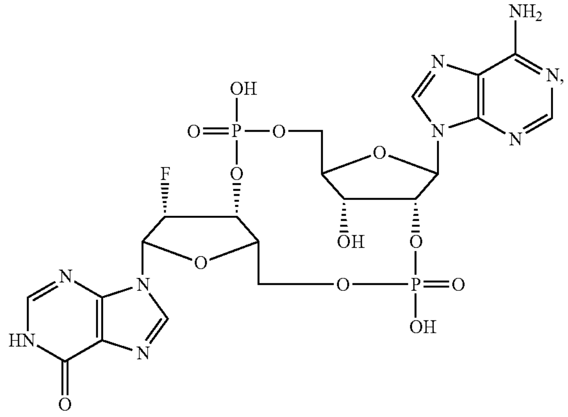
(2′,3′)c-(AMP-2′FdIMP)
CL626
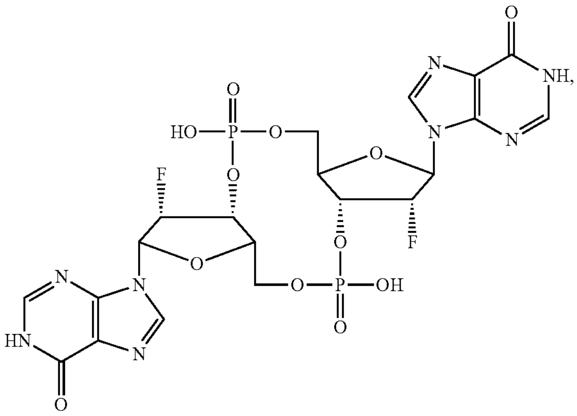
c-di(2′-FdIMP)
CL629
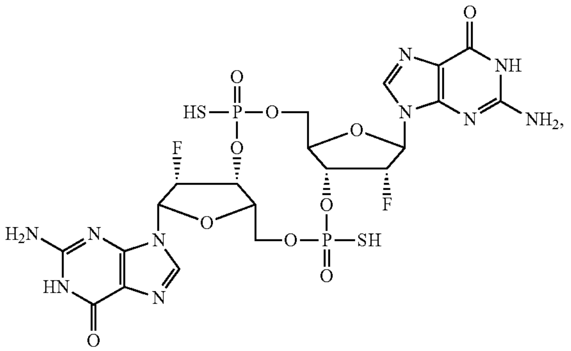
c-di(2′-FdGMP)

-continued

CL603

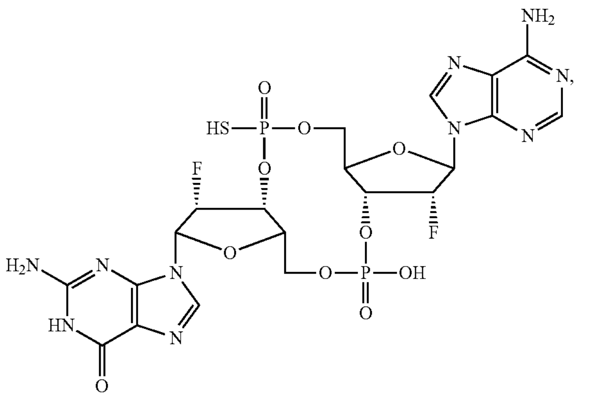

c-(2′-FdGMP-2′FdAMP)

CL632

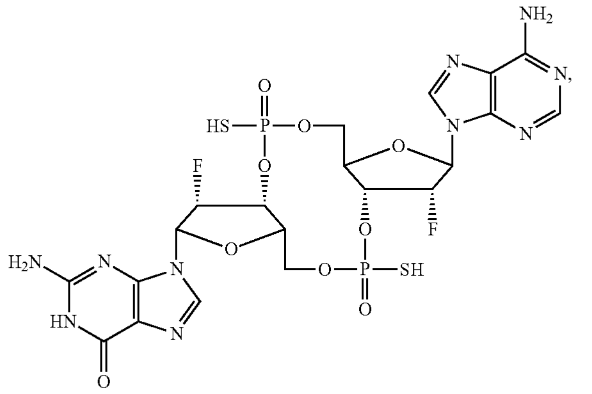

c-[2′FdGMP(S)-2′FdAMP(S)]

CL633

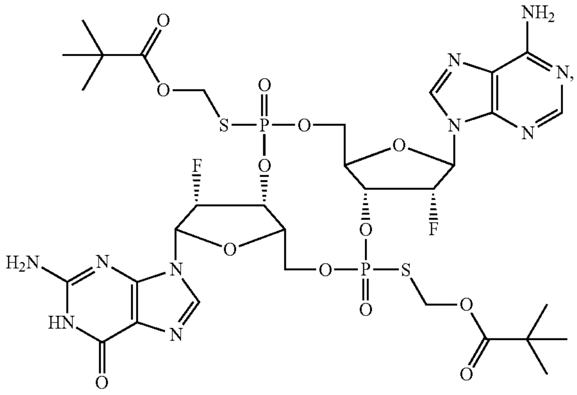

c-[2′FdGMP(S)-2′FdAMP(S)](POM)$_2$

-continued

CL659

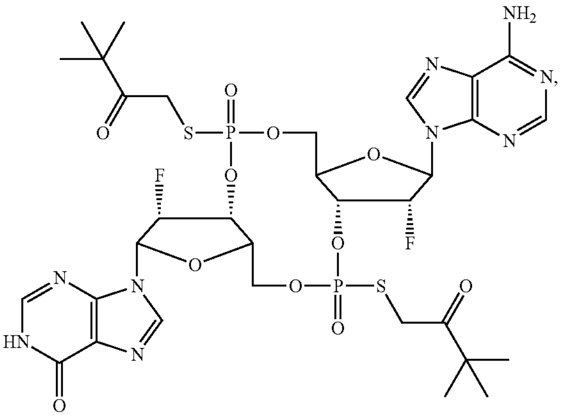

c-[2′FdGMP(S)-2′FdIMP(S)](POM)$_2$ or any pharmaceutically acceptable salts thereof.

In some aspects, the STING agonist useful for the present disclosure comprises a compound having the following formula:

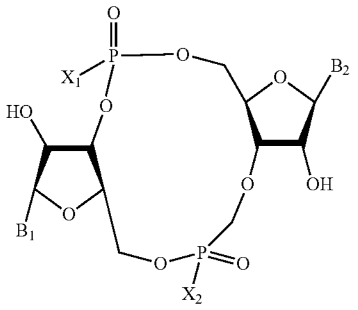

wherein each symbol is defined in WO 2014/093936, the content of which is incorporated herein by reference in its entirety.

In some aspects, the STING agonist useful for the present disclosure comprises a compound having the following formula:

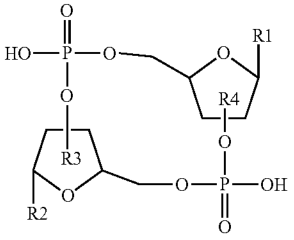

and

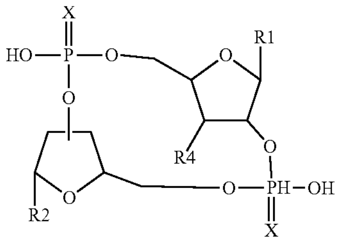

wherein each symbol is defined in WO 2014/189805, the content of which is incorporated herein by reference in its entirety.

In some aspects, the STING agonist useful for the present disclosure comprises a compound having the following formula:

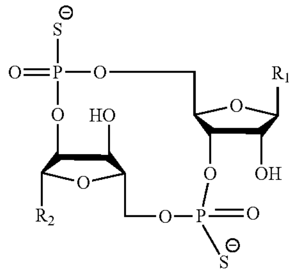

wherein each symbol is defined in WO 2015/077354, the content of which is incorporated herein by reference in its entirety. See also Cell reports 11, 1018-1030 (2015).

In some aspects, the STING agonist useful for the present disclosure comprises c-di-AMP, c-di-GMP, c-di-IMP, c-AMP-GMP, c-AMP-IMP, and c-GMP-IMP, described in WO 2013/185052 and Sci. Transl. Med. 283,283ra52 (2015), which are incorporated herein by reference in their entireties.

In some aspects, the STING agonist useful for the present disclosure comprises a compound having the following formula:

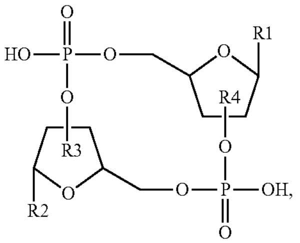

and

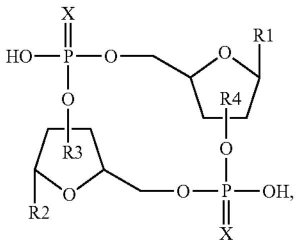

wherein each symbol is defined in WO 2014/189806, the content of which is incorporated herein by reference in its entirety.

In some aspects, the STING agonist useful for the present disclosure comprises a compound having the following formula:

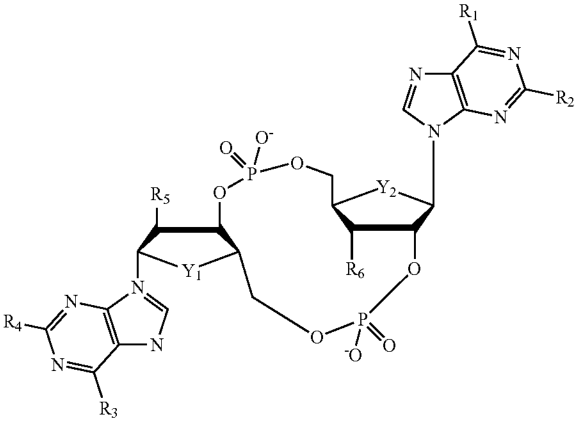

wherein each symbol is defined in WO 2015/185565, the content of which is incorporated herein by reference in its entirety.

In some aspects, the STING agonist useful for the present disclosure comprises a compound having the following formula:

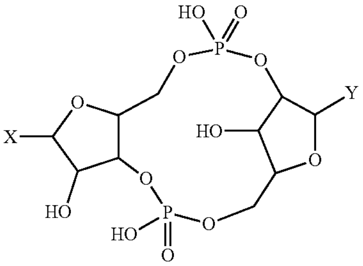

or

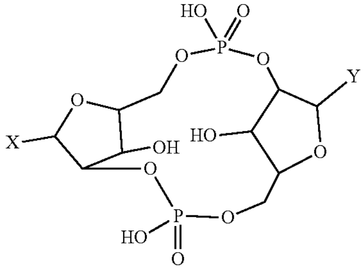

wherein each symbol is defined in WO 2014/179760, the content of which is incorporated herein by reference in its entirety.

In some aspects, the STING agonist useful for the present disclosure comprises a compound having the following formula:

-continued
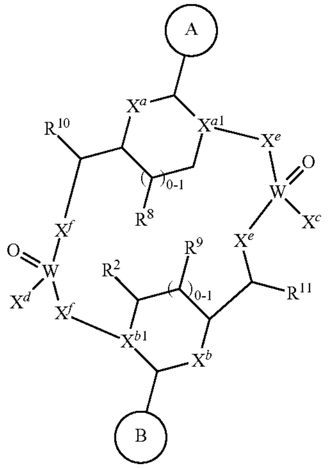
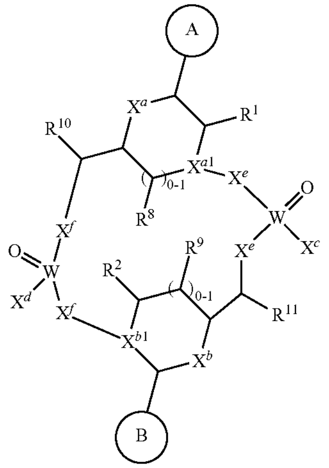
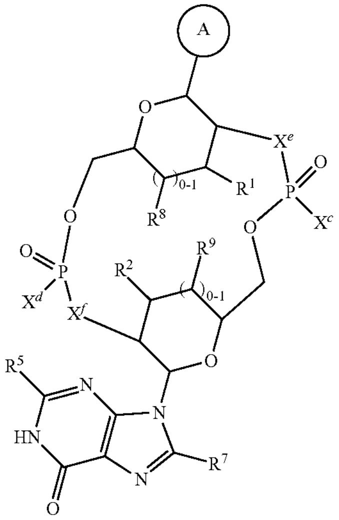
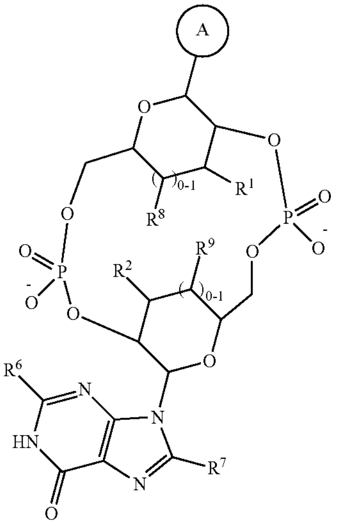
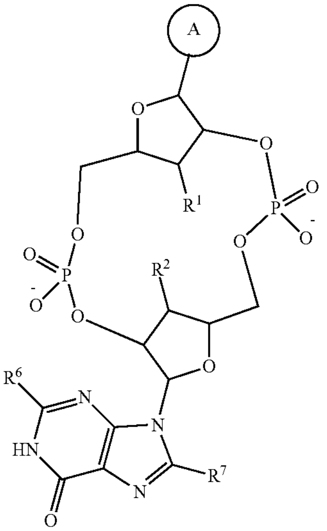
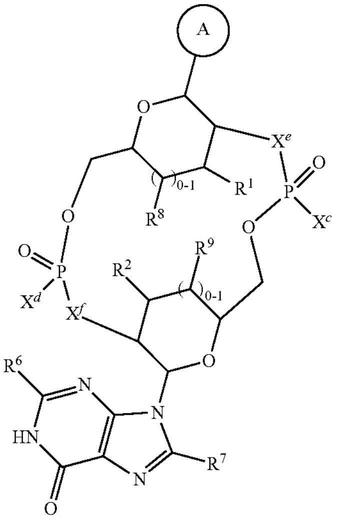

-continued

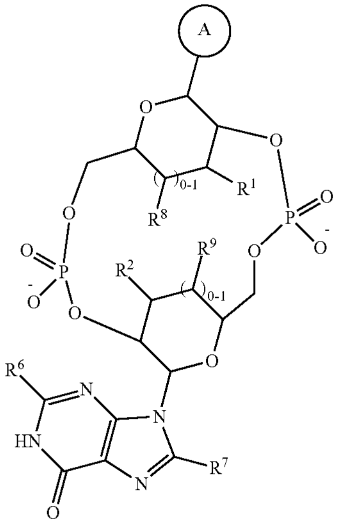

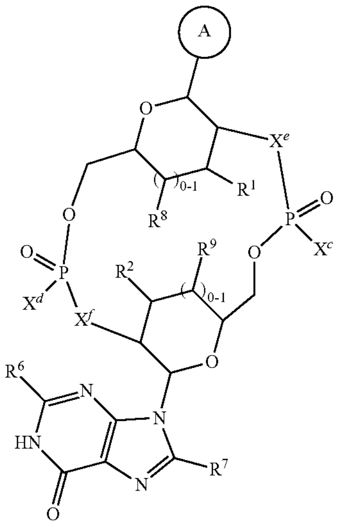

wherein each symbol is defined in WO 2014/179335, the content of which is incorporated herein by reference in its entirety.

In some aspects, the STING agonist useful for the present disclosure comprises a compound having the following formula:

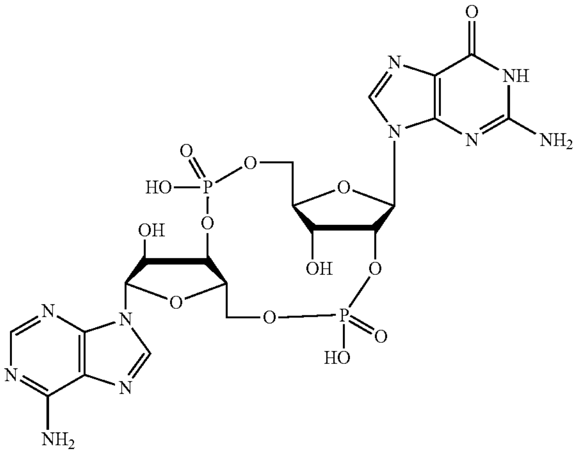

described in WO 2015/017652, the content of which is incorporated herein by reference in its entirety.

In some aspects, the STING agonist useful for the present disclosure comprises a compound having the following formula:

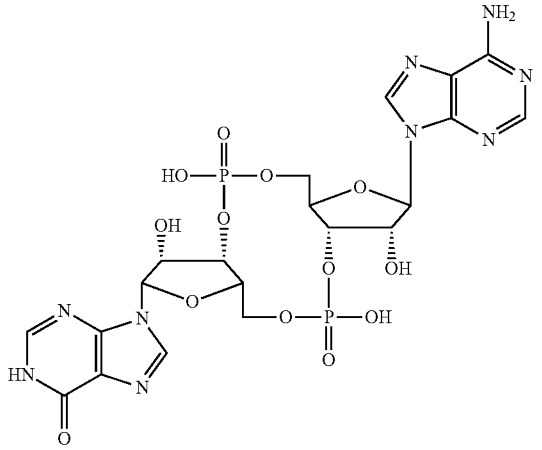 [SMILES: Nc1ncnc2c1ncn2C1OC2COP(=O)(O)O[C@@H]3C(COP(=O)(O)O[C@H]2[C@H]1O)OC(n1cnc2c(=O)[nH]cnc21)[C@@H]3O]

described in WO 2016/096577, the content of which is incorporated herein by reference in its entirety.

In some aspects, the STING agonist useful for the present disclosure comprises a compound having the following formula:

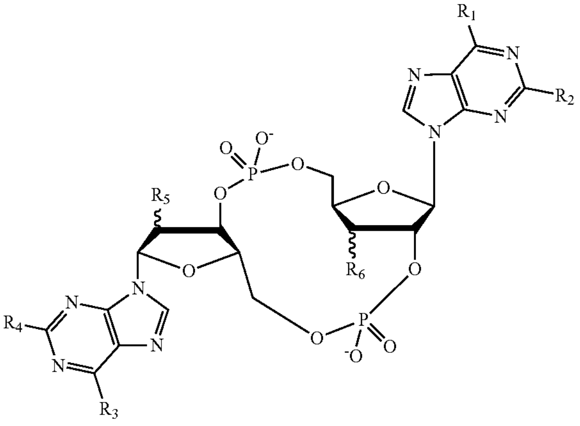

wherein each symbol is defined in WO 2016/120305, the content of which is incorporated herein by reference in its entirety.

In some aspects, the STING agonist useful for the present disclosure comprises a compound having the following formula:

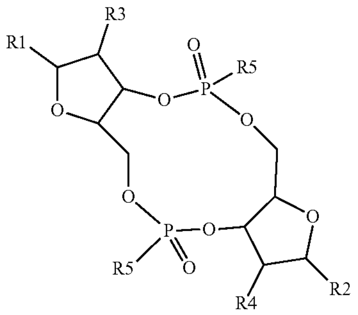

wherein each symbol is defined in WO 2016/145102, the content of which is incorporated herein by reference in its entirety.

In some aspects, the STING agonist useful for the present disclosure comprises a compound having the following formula:

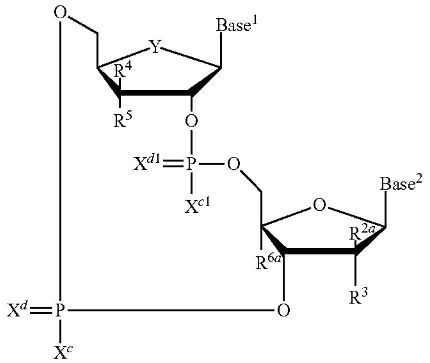

wherein each symbol is defined in WO 2017/027646, the content of which is incorporated herein by reference in its entirety.

In some aspects, the STING agonist useful for the present disclosure comprises a compound having the following formula:

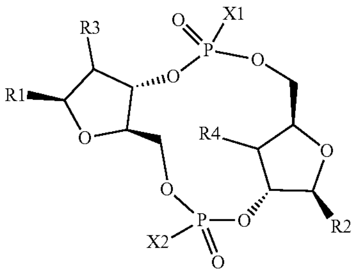

wherein each symbol is defined in WO 2017/075477, the content of which is incorporated herein by reference in its entirety.

In some aspects, the STING agonist useful for the present disclosure comprises a compound having the following formula:

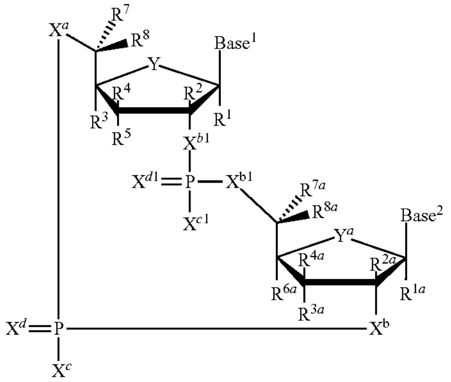

wherein each symbol is defined in WO 2017/027645, the content of which is incorporated herein by reference in its entirety.

In some aspects, the STING agonist useful for the present disclosure comprises a compound having the following formula:

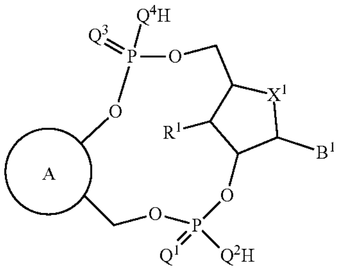

wherein each symbol is defined in WO 2018/100558, the content of which is incorporated herein by reference in its entirety.

In some aspects, the STING agonist useful for the present disclosure comprises a compound having the following formula:

(1-N)

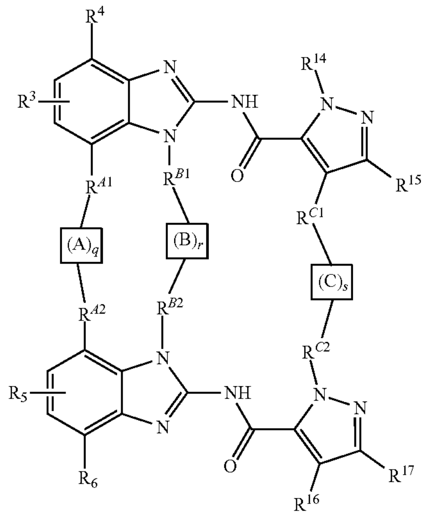

wherein each symbol is defined in WO 2017/175147, the content of which is incorporated herein by reference in its entirety.

In some aspects, the STING agonist useful for the present disclosure comprises a compound having the following formula:

(I)

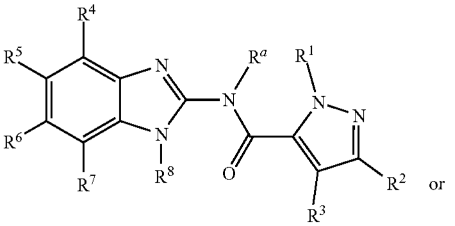

or

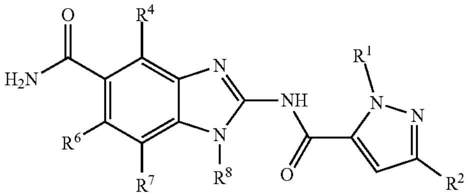

wherein each symbol is defined in WO 2017/175156, the content of which is incorporated herein by reference in its entirety.

In some aspects, the STING agonist useful for the present disclosure is CL606, CL611, CL602, CL655, CL604, CL609, CL614, CL656, CL647, CL626, CL629, CL603, CL632, CL633, CL659, or a pharmaceutically acceptable salt thereof. In some aspects, the STING agonist useful for the present disclosure is CL606 or a pharmaceutically acceptable salt thereof. In some aspects, the STING agonist useful for the present disclosure is CL611 or a pharmaceutically acceptable salt thereof. In some aspects, the STING agonist useful for the present disclosure is CL602 or a pharmaceutically acceptable salt thereof. In some aspects, the STING agonist useful for the present disclosure is CL655 or a pharmaceutically acceptable salt thereof. In some aspects, the STING agonist useful for the present disclosure is CL604 or a pharmaceutically acceptable salt thereof. In some aspects, the STING agonist useful for the present disclosure is CL609 or a pharmaceutically acceptable salt thereof. In some aspects, the STING agonist useful for the present disclosure is CL614 or a pharmaceutically acceptable salt thereof. In some aspects, the STING agonist useful for the present disclosure is CL656 or a pharmaceutically acceptable salt thereof. In some aspects, the STING agonist useful for the present disclosure is CL647 or a pharmaceutically acceptable salt thereof. In some aspects, the STING agonist useful for the present disclosure is CL626 or a pharmaceutically acceptable salt thereof. In some aspects, the STING agonist useful for the present disclosure is CL629 or a pharmaceutically acceptable salt thereof. In some aspects, the STING agonist useful for the present disclosure is CL603 or a pharmaceutically acceptable salt thereof. In some aspects, the STING agonist useful for the present disclosure is CL632 or a pharmaceutically acceptable salt thereof. In some aspects, the STING agonist useful for the present disclosure is CL633 or a pharmaceutically acceptable salt thereof. In some aspects, the STING agonist useful for the present disclosure is CL659 or a pharmaceutically acceptable salt thereof.

In some aspects, the STING agonist useful for the present disclosure is CP-201 or a pharmaceutically acceptable salt thereof. In some aspects, the STING agonist useful for the present disclosure comprises a compound having the following formula:

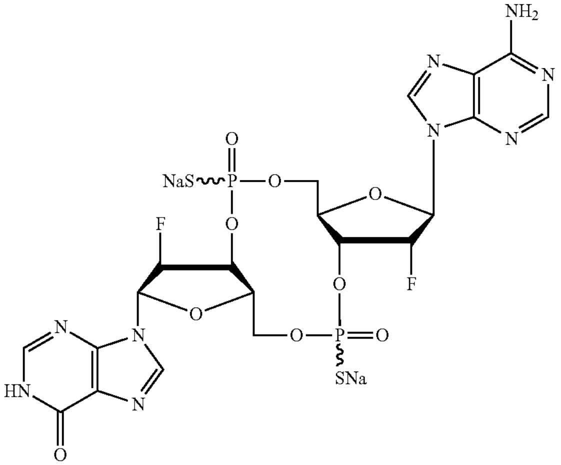

In some aspects, the EV, e.g., exosome, comprises a cyclic dinucleotide STING agonist and/or a non-cyclic dinucleotide STING agonist. In some aspects, when several cyclic dinucleotide STING agonist are present on an EV, e.g., exosome, disclosed herein, such STING agonists can be the same or they can be different. In some aspects, when several non-cyclic dinucleotide STING agonist are present, such STING agonists can be the same or they can be different. In some aspects, an EV, e.g., exosome, composition of the present disclosure can comprise two or more populations of EVs, e.g., exosomes, wherein each population of EVs, e.g., exosomes, comprises a different STING agonist or combination thereof.

In some aspects, the concentration of the STING agonist associated with the EV is about 0.01 μM to about 1000 μM. In some aspects, the concentration of the associated STING agonist is between about 0.01-0.05 μM, about 0.05-0.1 μM, about 0.1-0.5 μM, about 0.5-1 μM, about 1-5 μM, about 5-10 μM, about 10-15 μM, about 15-20 μM, about 20-25 μM, about 25-30 μM, about 30-35 μM, about 35-40 μM, about 45-50 μM, about 55-60 μM, about 65-70 μM, about 70-75 μM, about 75-80 μM, about 80-85 μM, about 85-90 μM, about 90-95 μM, about 95-100 μM, about 100-150 μM, about 150-200 μM, about 200-250 μM, about 250-300 μM, about 300-350 μM, about 250-400 μM, about 400-450 μM, about 450-500 μM, about 500-550 μM, about 550-600 μM, about 600-650 μM, about 650-700 μM, about 700-750 μM, about 750-800 μM, about 800-850 μM, about 850-900 μM, about 900-950 μM, or about 950-1000 μM. In some aspects, the concentration of the associated STING agonist is equal to or greater than about 0.01 μM, about 0.1 μM, about 0.5 μM, about 1 μM, about 5 μM, about 10 μM, about 15 μM, about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 150 μM, about 200 μM, about 250 μM, about 300 μM, about 350 μM, about 400 μM, about 450 μM, about 500 μM, about 550 μM, about 600 μM, about 650 μM, about 700 μM, about 750 μM, about 800 μM, about 850 μM, about 900 μM, about 950 μM, or about 1000 μM.

IV. Producer Cells

EVs, e.g., exosomes, can be produced from a cell grown in vitro or a body fluid of a subject. When EVs, e.g., exosomes, are produced from in vitro cell culture, various producer cells, e.g., HEK293 cells, can be used. Additional cell types that can be used for the production of the lumen-engineered EVs, e.g., exosomes, described herein include, without limitation, mesenchymal stem cells, T-cells, B-cells, dendritic cells, macrophages, and cancer cell lines. Further examples include: Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, and RPTEC/TERT1 cells. In certain aspects, a producer cell is not a dendritic cell, macrophage, B cell, mast cell, neutrophil, Kupffer-Browicz cell, cell derived from any of these cells, or any combination thereof.

In some aspects, the EV, e.g., exosome, is genetically modified to comprise one or more exogenous sequences to produce modified EVs that express exogenous proteins on the vesicle surface. The exogenous sequences can comprise a sequence encoding the EV, e.g., exosome, protein or a modification or a fragment of the EV protein. An extra copy of the sequence encoding the EV, e.g., exosome, protein can be introduced to produce a surface-engineered EV having a higher density of the EV protein. An exogenous sequence encoding a modification or a fragment of the EV, e.g., exosome, protein can be introduced to produce a modified EV containing the modification or the fragment of the EV protein. An exogenous sequence encoding an affinity tag can be introduced to produce a modified EV, e.g., exosome, containing a fusion protein comprising the affinity tag attached to the EV protein.

The STING agonists can also be modified to increase encapsulation of the agonist in an extracellular vesicle or EV (e.g., either unbound in the lumen). In some aspects, the STING agonists are linked to a scaffold moiety, e.g., Scaffold X. In certain aspects, the modification allows better expression of the STING agonist on the exterior surface of the EV, e.g., exosome, (e.g., linked to a scaffold moiety disclosed herein, e.g., Scaffold X). This modification can include the addition of a lipid binding tag by treating the agonist with a chemical or enzyme, or by physically or chemically altering the polarity or charge of the STING agonist. In some aspects, the STING agonist is modified by a single treatment, or by a combination of treatments, e.g., adding a lipid binding tag only, or adding a lipid binding tag and altering the polarity. The previous example is meant to be a non-limiting illustrative instance. In some aspects, the modification increases encapsulation of the agonist in the EV by between 2-fold and 10,000 fold, between 10-fold and 1,000 fold, or between 100-fold and 500-fold compared to encapsulation of an unmodified agonist. In some aspects, the modification increases encapsulation of the agonist in the EV by at least 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, or 10,000-fold compared to encapsulation of an unmodified agonist.

In some aspects, STING agonists can be modified to allow for better expression of the agonists on the exterior surface of the EV, e.g., exosome, (e.g., linked to a scaffold moiety disclosed herein, e.g., Scaffold X). Any of the modifications described above can be used. In some aspects, the modification increases encapsulation of the agonist in the EV, e.g., exosome, by about between 2-fold and 10,000 fold, about between 10-fold and 1,000 fold, or about between 100-fold and 500-fold compared to encapsulation of an unmodified agonist. The modification can increase expression of the agonist on the exterior surface of the EV, e.g., exosome, by at least about 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, or 10,000-fold compared to expression of an unmodified agonist.

In some aspects, the exogenous sequence encodes for Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof). In some aspects the modified EV, e.g., exosome, overexpresses Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof). In other aspects, the EV, e.g., exosome, is produced by a cell that overexpresses Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof).

In some aspects, the exogenous sequence is transiently or stabled expressed in the producer cell or cell line via transfection, transformation, transduction, electroporation, or any other appropriate method of gene delivery or combination thereof known in the art. In some aspects, the exogenous sequence is integrated into the producer cell genome, or remain extra chromosomal. The exogenous sequence can be transformed as a plasmid. The exogenous sequences can be stably integrated into a genomic sequence of the producer cell, at a targeted site or in a random site. The exogenous sequences can be inserted into a genomic sequence of the producer cell, located within, upstream (5'-end) or downstream (3'-end) of an endogenous sequence encoding the EV, e.g., exosome, protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 CRISPR/Cfp1, CRISPR/C2c1, C2c2, or C2c3, CRISPR/CasY or CasX, TAL-effector nuclease or TALEN, or zinc finger nuclease (ZFN) systems) are within the scope of various aspects.

In some aspects, the producer cell is further modified to comprise an additional exogenous sequence. For example, an additional exogenous sequence can be included to modulate endogenous gene expression, modulate the immune response or immune signaling, or produce an EV, e.g., exosome, including a certain polypeptide as a payload or additional surface expressed ligand. In some aspects, the producer cell can be further modified to comprise an additional exogenous sequence conferring additional functionalities to EVs, e.g., exosomes, for example, specific targeting capabilities, delivery functions, enzymatic functions, increased or decreased half-life in vivo, etc. In some aspects, the producer cell is modified to comprise two exogenous sequences, one encoding the exosome protein or a modification or a fragment of the exosome protein, and the other encoding a protein conferring the additional functionalities to exosomes.

More specifically, the EV, e.g., exosome, of the present can be produced from a cell transformed with a sequence encoding one or more additional exogenous proteins including, but not limited to ligands, cytokines, or antibodies, or any combination thereof. In some aspects, these additional exogenous proteins enable activation or modulation of additional immune stimulatory signals in combination with the STING agonist. Exemplary additional exogenous proteins contemplated for use include the proteins, ligands, and other molecules described in detail in U.S. Patent Application 62/611,140, which is incorporated herein by reference in its entirety. In some aspects, the EV, e.g., exosome, is further modified with a ligand comprising CD40L, OX40L, or CD27L. In some aspects, the EV, e.g., exosome, is further modified with a cytokine comprising IL-7, IL-12, or IL-15. Any of the one or more exosome proteins described herein can be expressed from a plasmid, an exogenous sequence inserted into the genome or other exogenous nucleic acid such as a synthetic messenger RNA (mRNA).

In some aspects, the EV, e.g., exosome, is further modified to display an antagonistic antibody or an agonistic antibody or a fragment thereof on the EV, e.g., exosome, surface to direct EV uptake, activate, or block cellular pathways to enhance the combinatorial effect of the STING agonist. In some specific aspects, the antibody or fragment thereof is an antibody against DEC205, CLEC9A, CLEC6, DCIR, DC-SIGN, LOX-1, or Langerin. In some aspects, the producer cell is modified to comprise an additional exogenous sequence encoding for an antagonistic antibody or an agonistic antibody. In some aspects, the antagonistic antibody or agonistic antibody is covalently linked or conjugated to the EV, e.g., exosome, via any appropriate linking chemistry known in the art. Non-limiting examples of appropriate linking chemistry include amine-reactive groups, carboxyl-reactive groups, sulfhydryl-reactive groups, aldehyde-reactive groups, photoreactive groups, ClickIT chemistry, biotin-streptavidin or other avidin conjugation, or any combination thereof.

V. Filtration Between Chromatography

In some aspects, one or more filtration steps are added between the chromatographic purification steps. For example, adsorptive depth filtrations step can be added before, between, or after chromatographic steps. In some aspects, the filter size is bigger than about 0.14 micron, about 0.16 micron, about 0.18 micron, about 0.2 micron, about 0.25 micron, about 0.3 micron, about 0.35 micron, about 0.4 micron, about 0.45 micron, about 0.5 micron, about 0.55 micron, about 0.6 micron, about 0.65 micron, or about 0.7 micron. In some aspects, the filter is smaller than about 0.25 micron, about 0.22 micron, about 0.2 micron, about 0.18 micron, about 0.16 micron, or about 0.14 micron.

In some aspects, the present filtration useful in the process is a sterile filtration. One or more sterile filtrations can be performed within the present methods. In some aspects, at least one, at least two, at least three, at least four, at least five, at least six, at least seven, at least eight, at least nine, at least ten, at least 11, at least 12, at least 13, at least 14, or at least 15 filtrations can be introduced in the present methods. In some aspects, a sterile filtration can be introduced before one or more chromatographies. In some aspects, a sterile filtration can be introduced between two or more chromatographies. In some aspects, a filtration can be used right after the separation. In other aspects, a filtration can be used right before formulation.

VI. Pharmaceutical Compositions

Provided herein are pharmaceutical compositions comprising EVs, e.g., exosomes, that are suitable for administration to a subject. The pharmaceutical compositions generally comprise a plurality of EVs, e.g., exosomes, comprising a STING agonist (e.g., encapsulated or expressed on the luminal or exterior surface) and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of EVs, e.g., exosomes. (See, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration.

The pharmaceutical compositions of the present disclosure are useful to formulate cyclic dinucleotides (CDNs) or STING agonists. In some aspects, the pharmaceutical composition comprises at least about 1 μM, at least about 2 μM, at least about 3 μM, at least about 4 μM, at least about 5 μM, at least about 6 μM, at least about 7 μM, at least about 8 μM, at least about 9 μM, or at least about 10 μM of CDNs. In some aspects, the pharmaceutical composition comprises at least about 10 μM, at least about 20 μM, at least about 30 μM, at least about 40 μM, at least about 50 μM, at least about 60 μM, at least about 70 μM, at least about 80 μM, at least about 90 μM, or at least about 100 μM of CDNs. In some aspects, the pharmaceutical composition comprises at least about 100 μM, at least about 200 μM, at least about 300 μM, at least about 400 μM, at least about 500 μM, at least about 600 μM, at least about 700 μM, at least about 800 μM, at least about 900 μM, or at least about 1 mM of CDNs.

The methods of the present disclosure are related to pharmaceutical compositions wherein the pharmaceutical composition is more potent than a reference composition comprising EVs and the same concentration of CDNs, wherein the reference composition is not subjected to a clean-up process to remove free CDNs. In some aspects, the composition of the present disclosure has reduced aggregation as compared to a reference composition comprising EVs and the same amount of CDNs, wherein the pharmaceutical composition is not subjected to a clean-up process. The methods of the present disclosure are also useful to produce EV compositions with reduced aggregation with respect to unformulated EVs. In some aspects, the composition of the present disclosure has reduced aggregation as compared to a reference composition comprising EVs and the same amount of CDNs, wherein the pharmaceutical composition is not subjected to a clean-up process.

The methods of the present disclosure are useful to prepare stable pharmaceutical compositions further comprising a saccharide, sodium chloride, potassium phosphate, and/or sodium phosphate. In some aspects, the saccharide has a molecular weight of from about 90.00 g/mol to about 380.00 g/mol. In some aspects, the saccharide has a molecular weight of from about 180.00 g/mol to about 380.00 g/mol. In some aspects, the saccharide comprises lactose. In some aspects, the saccharide comprises glucose. In some aspects, the saccharide comprises sucrose. In some aspects, the saccharide comprises trehalose. In some aspects, the saccharide comprises dextrose. In some aspects, the saccharide comprises any combination of saccharides described herein. In some aspects, the saccharide is a sugar alcohol. In some aspects, the saccharide is a sugar alcohol having a molecular weight of from about 90.00 g/mol to about 190.00 g/mol. In some aspects, the sugar alcohol comprises glycerol. In some aspects, the sugar alcohol comprises sorbitol. In some aspects, the sugar alcohol comprises mannitol. In some aspects, the sugar alcohol comprises xylitol. In some aspects, the sugar alcohol comprises any combination of sugar alcohols described herein. In some aspects, the saccharide is a sucrose or a trehalose. In some aspects, the saccharide is trehalose. In some aspects, the saccharide is sucrose.

In some aspects, the saccharide comprises a monosaccharide, a disaccharide, a trisaccharide, an oligosaccharide, a polysaccharide, a sugar alcohol, or any combination thereof. In some aspects, the saccharide has a molecular weight of from about 340.00 g/mol to about 380.00 g/mol. In some aspects, the saccharide comprises lactose, glucose, sucrose, trehalose, dextrose, and/or combinations thereof. In some aspects, the saccharide is a sugar alcohol having a molecular weight of from about 90.00 g/mol to about 190.00 g/mol. In some aspects, the sugar alcohol comprises glycerol, sorbitol, mannitol, xylitol, and/or combinations thereof. In some aspects, the saccharide is a sucrose or a trehalose. In some aspects, the saccharide is a sucrose. In some aspects, the saccharide is a trehalose. In some aspects, the saccharide is present in the composition at a concentration of about 1% w/v, about 2% w/v, about 3% w/v, about 4% w/v, about 5% w/v, about 6% w/v, about 7% w/v, about 8% w/v, about 9% w/v, or about 10% w/v. In some aspects, the saccharide is present in the composition at a concentration of about 11% w/v, about 12% w/v, about 13% w/v, about 14% w/v, about 15% w/v, about 16% w/v, about 17% w/v, about 18% w/v, about 19% w/v, or about 20% w/v. In some aspects, the saccharide is present in the composition at a concentration of about 5% w/v. In some aspects, the saccharide is trehalose and is present in the composition at a concentration of about 5% w/v. In some aspects, the saccharide is sucrose and is present in the composition at a concentration of about 5% w/v.

The methods of the present disclosure are also useful for producing compositions with antioxidants. In some aspects, the compositions of the present disclosure further comprise an anti-oxidant. In some aspects, the anti-oxidant comprises methionine, L-methionine, ascorbic acid, erythorbic acid, Na ascorbate, thioglycerol, cysteine, acetylcysteine, cystine, dithioerythreitol, dithiothreitol, glutathione, tocopherols, butylated hydroxyanisole (BHA), butylated hydroxytoluene (BHT), or sodium thiosulfate. In some aspects, the anti-oxidant is methionine. In other aspects, the anti-oxidant is L-methionine.

In some aspects, the composition further comprises sodium chloride. And is present in the composition at a concentration of between about 10 mM and about 134 mM. In some aspects, the concentration of sodium chloride is between about 10 mM to about 130 mM. In some aspects, the concentration of sodium chloride is between about 20 mM to about 120 mM. In some aspects, the concentration of sodium chloride is between about 30 mM to about 110 mM. In some aspects, the concentration of sodium chloride is between about 40 mM to about 100 mM. In some aspects, the concentration of sodium chloride is between about 50 mM to about 90 mM. In some aspects, the concentration of sodium chloride is between about 60 mM to about 80 mM. In some aspects, the concentration of sodium chloride is between about 70 mM to about 80 mM. In some aspects, the concentration of sodium chloride is between about 45 mM to about 95 mM. In some aspects, the concentration of sodium chloride is between about 45 mM to about 80 mM. In some aspects, the concentration of sodium chloride is between about 45 mM to about 70 mM. In some aspects, the concentration of sodium chloride is between about 45 mM to about 65 mM. In some aspects, the concentration of sodium chloride is between about 50 mM to about 65 mM. In some aspects, the concentration of sodium chloride is between about 50 mM to about 60 mM. In some aspects, the concentration of sodium chloride is between about 50 mM to about 55 mM. In some aspects, the concentration of sodium chloride is between about 50 mM to about 55 mM.

In some aspects, the concentration of sodium chloride is about 10 mM. In some aspects, the concentration of sodium chloride is about 20 mM. In some aspects, the concentration of sodium chloride is about 30 mM. In some aspects, the concentration of sodium chloride is about 40 mM. In some aspects, the concentration of sodium chloride is about 50 mM. In some aspects, the concentration of sodium chloride is about 60 mM. In some aspects, the concentration of sodium chloride is about 70 mM. In some aspects, the concentration of sodium chloride is about 80 mM. In some aspects, the concentration of sodium chloride is about 90 mM. In some aspects, the concentration of sodium chloride is about 100 mM. In some aspects, the concentration of sodium chloride is about 110 mM. In some aspects, the concentration of sodium chloride is about 120 mM. In some aspects, the concentration of sodium chloride is about 130 mM. In some aspects, the concentration of sodium chloride is about 140 mM.

In some aspects, the pharmaceutical composition is further diluted into a buffer and remains potent as compared to a reference composition comprising EVs and the same amount of CDNs, wherein the pharmaceutical composition was not subjected to a clean-up process.

In some aspects, the pharmaceutical composition comprises one or more STING agonist and the EVs, e.g., exosomes, described herein. Pharmaceutically-acceptable excipients include excipients that are generally safe (GRAS), non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the EVs, e.g., exosomes, described herein, use thereof in the compositions is contemplated. In some aspects, supplementary therapeutic agents are incorporated into the compositions. Typically, a pharmaceutical composition is formulated to be compatible with its intended route of administration. The EVs, e.g., exosomes, can be administered by intratumoral, parenteral, topical, intravenous, oral, subcutaneous, intraarterial, intradermal, transdermal, rectal, intracranial, intraperitoneal, intranasal; intramuscular route or as inhalants. In one aspect, the pharmaceutical composition comprising EVs, e.g., exosomes, is administered intravenously, e.g. by injection. The EVs, e.g., exosomes, can optionally be administered in combination with other therapeutic agents that are at least partly effective in treating the disease, disorder or condition for which the EVs, e.g., exosomes, are intended.

Solutions or suspensions can include the following components: a sterile diluent such as water, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, sodium chloride can be added to the composition. Prolonged absorption of the injectable compositions can be brought about by including in the composition a compound which delays absorption, e.g., aluminum monostearate and gelatin. In some aspects, the buffer is a TRIS buffer. In some aspects, the buffer is a PBS buffer.

In some aspects, the composition is capable of being frozen and thawed. Certain formulations, such as those containing TRIS buffer, do not prevent the pH from fluctuating at various temperatures (i.e., when the formulation is frozen or thawed). Even small variations in pH can induce aggregation of the EVs, thereby reducing or preventing their functionality. In some aspects, the frozen composition has a pH of about 7.1. In some aspects, the frozen composition has a pH of about 7.2. In some aspects, the frozen composition has a pH of about 7.3. In some aspects, the frozen composition has a pH of about 7.4.

The methods of the present disclosure are useful for preparing sterile injectable solutions that can be delivered to subjects in need thereof. In some aspects, sterile injectable solutions are prepared by incorporating the EVs, e.g., exosomes, in an effective amount and in an appropriate solvent with one or a combination of ingredients enumerated herein, as desired. Generally, dispersions are prepared by incorporating the EVs, e.g., exosomes, into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. In some aspects, the EVs, e.g., exosomes, are administered in the form of a depot injection or implant preparation which are formulated to permit a sustained or pulsatile release of the EVs, e.g., exosomes. In some aspects, the composition is not lyophilized.

Systemic administration of compositions comprising EVs, e.g., exosomes, can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified EVs, e.g., exosomes, are formulated into ointments, salves, gels, or creams as generally known in the art.

The pharmaceutical compositions provided herein are useful to maintain long term potency, even after removal of free CDNs or STING agonists via chromatography. In one aspect, a CDN or STING agonist is associated or encapsulated by an EV, e.g., exosome, formulated after removal of free CDNs or STING agonists, and passively diffuses out of or away from the exosome. In some aspects, the CDN or STING agonist and the EV, e.g., exosome, is formulated together in a final formulation sufficient for the CDN or STING agonist to diffuse through the vesicle lipid bilayer, thereby becoming unencapsulated or disassociated from the EV, e.g., exosome. However, the methods of the present disclosure are effective to maintain potency of the formulation even after this passive diffusion. In some aspects, the diffusion reaches an equilibrium where about 1%, where about 2%, where about 3%, where about 4%, where about 5%, where about 6%, where about 7%, where about 8%, where about 9%, or where about 10% of the CDN or STING agonist associated or encapsulated in the EV is disassociated or unencapsulated from the EV.

In some aspects, the composition comprising EVs prior to the loading CDNs and chromatography comprises:

(a) EVs;

(b) Sucrose at a concentration between about 4% w/v and about 6% w/v, e.g., 5% w/v;

(c) Sodium chloride at a concentration between 40 mM and about 60 mM;

(d) Potassium phosphate monobasic at a concentration between 4 mM and 6 mM;

(e) sodium phosphate dibasic heptahydrate at a concentration between about 10 mM and about 20 mM, wherein the pH of the composition is about 7.2. In some aspects, the conductivity of the composition is about 7.2 mS/cm. In some aspects, the composition is in solution, e.g., a liquid formulation.

In some aspects, the composition comprising EVs prior to the loading CDNs and chromatography comprises:

(a) EVs;

(b) Sucrose at a concentration of about 5% w/v;

(c) Sodium chloride at a concentration of about 50 mM;

(d) Potassium phosphate monobasic at a concentration of about 5 mM;

(e) sodium phosphate dibasic heptahydrate at a concentration of about 15 mM, wherein the pH of the composition is about 7.2. In some aspects, the conductivity of the composition is about 7.2 mS/cm. In some aspects, the composition is in solution, e.g., a liquid formulation.

In some aspects, the composition comprising EVs with loaded CDNs of the present disclosure comprises:

(a) EVs;

(b) Sucrose at a concentration between about 4% w/v and about 6% w/v, e.g., 5% w/v;

(c) Sodium chloride at a concentration between 30 mM and about 50 mM;

(d) Potassium phosphate monobasic at a concentration between 10 mM and 20 mM;

(e) sodium phosphate dibasic heptahydrate at a concentration between about 20 mM and about 40 mM, wherein the pH of the composition is about 7.2. In some aspects, the conductivity of the composition is about 8.8 mS/cm. In some aspects, the composition is in solution, e.g., a liquid formulation.

In some aspects, the composition comprising EVs with loaded CDNs of the present disclosure comprises:

(a) EVs;

(b) Sucrose at a concentration of about 5% w/v;

(c) sodium chloride at a concentration of about 40 mM;

(d) Potassium phosphate monobasic at a concentration of about 15 mM;

(e) sodium phosphate dibasic heptahydrate at a concentration of about 27 mM, wherein the pH of the composition is about 7.2. In some aspects, the conductivity of the composition is about 8.8 mS/cm. In some aspects, the composition is in solution, e.g., a liquid formulation.

VI. Methods of Treatment

Administration of the presently disclosed pharmaceutical compositions for treating a plurality of diseases or conditions where administration of EVs are of beneficial effect to a subject, is further contemplated. In some aspects, the methods of treating a disease or a condition in a subject disclosed herein comprise administering to the subject the pharmaceutical composition.

In some aspects, the present disclosure provides a composition which can be administered by a parenteral, topical, intravenous, oral, subcutaneous, intra-arterial, intradermal, transdermal, rectal, intracranial, intraperitoneal, intranasal, intratumoral, intramuscular route, or as an inhalant. In some aspects, the pharmaceutical composition comprising EVs is administered intravenously, e.g. by injection. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified exosomes are formulated into ointments, salves, gels, or creams as generally known in the art.

In some aspects, the EVs are administered intravenously to the circulatory system of the subject. In some aspects, the EVs are infused in suitable liquid and administered into a vein of the subject. In some aspects, the EVs are administered intra-arterially to the circulatory system of the subject. In some aspects, the EVs are infused in suitable liquid and administered into an artery of the subject. In some aspects, the EVs are administered to the subject by intrathecal administration. In some aspects, the EVs are administered via an injection into the spinal canal, or into the subarachnoid space so that it reaches the cerebrospinal fluid (CSF). In some aspects, the EVs are administered intratumorally into one or more tumors of the subject. In some aspects, the EVs are administered to the subject by intranasal administration. In some aspects, the EVs can be insufflated through the nose in a form of either topical administration or systemic administration. In certain aspects, the EVs are administered as nasal spray.

In some aspects, the EVs are administered to the subject by intraperitoneal administration. In some aspects, the EVs are infused in suitable liquid and injected into the peritoneum of the subject. In some aspects, the intraperitoneal administration results in distribution of the EVs to the lymphatics. In some aspects, the intraperitoneal administration results in distribution of the EVs to the thymus, spleen, and/or bone marrow. In some aspects, the intraperitoneal administration results in distribution of the EVs to one or more lymph nodes. In some aspects, the intraperitoneal administration results in distribution of the EVs to one or more of the cervical lymph node, the inguinal lymph node, the mediastinal lymph node, or the sternal lymph node. In some aspects, the intraperitoneal administration results in distribution of the EVs to the pancreas.

In some aspects, the EVs, e.g., exosomes, are administered to the subject by periocular administration. In some aspects, the s are injected into the periocular tissues. Periocular drug administration includes the routes of subconjunctival, anterior sub-Tenon's, posterior sub-Tenon's, and retrobulbar administration.

In some aspects, the treatment is prophylactic. In some aspects, the EVs for the present disclosure are used to induce an immune response. In some aspects, the EVs for the present disclosure are used to vaccinate a subject.

In some aspects, the disease or condition is a cancer. In some aspects, the cancer is bladder cancer, cervical cancer, renal cell cancer, testicular cancer, colorectal cancer, lung cancer, head and neck cancer, ovarian, lymphoma, liver cancer, glioblastoma, melanoma, myeloma, leukemia, pancreatic cancer, or combinations thereof. In some aspects, the cancer is a solid tumor. In some aspects, the cancer is head and neck squamous cell carcinoma (HNSCC), triple negative breast cancer (TNBC), cutaneous squamous cell carcinoma (CSCC, also called squamous cell carcinoma of the skin), anaplastic thyroid cancer (ATC), or any combination thereof. In some aspects, the cancer is head and neck squamous cell carcinoma (HNSCC). In some aspects, the cancer is triple negative breast cancer (TNBC). In some aspects, the cancer is cutaneous squamous cell carcinoma (CSCC, also called squamous cell carcinoma of the skin). In some aspects, the cancer is anaplastic thyroid cancer (ATC). In some aspects, the cancer is leptomeningeal cancer.

When administered to a subject with a cancer, in certain aspects, EVs of the present disclosure can up-regulate an immune response and enhance the tumor targeting of the subject's immune system. In some aspects, the cancer being treated is characterized by infiltration of leukocytes (T-cells, B-cells, macrophages, dendritic cells, monocytes) into the tumor microenvironment, or so-called "hot tumors" or "inflammatory tumors". In some aspects, the cancer being treated is characterized by low levels or undetectable levels of leukocyte infiltration into the tumor microenvironment, or so-called "cold tumors" or "non-inflammatory tumors". In some aspects, an EV is administered in an amount and for a time sufficient to convert a "cold tumor" into a "hot tumor", i.e., said administering results in the infiltration of leukocytes (such as T-cells) into the tumor microenvironment. In certain aspects, cancer comprises bladder cancer, cervical cancer, renal cell cancer, testicular cancer, colorectal cancer, lung cancer, head and neck cancer, and ovarian, lymphoma, liver cancer, glioblastoma, melanoma, myeloma, leukemia, pancreatic cancers, or combinations thereof. In some aspects, the cancer is a solid tumor. In some aspects, the cancer is head and neck squamous cell carcinoma (HNSCC), triple negative breast cancer (TNBC), cutaneous squamous cell carcinoma (CSCC, also called squamous cell carcinoma of the skin), anaplastic thyroid cancer (ATC), or any combination thereof. In other term, "distal tumor" or "distant tumor" refers to a tumor that has spread from the original (or primary) tumor to distant organs or distant tissues, e.g., lymph nodes. In some aspects, the EVs of the disclosure treats a tumor after the metastatic spread.

In some aspects, the disclosure further comprises a combination therapy with another therapeutic agent. In some aspects, the additional therapeutic agent comprises an IL-12 moiety. In other aspects, the IL-12 moiety comprises an EV comprising an IL-12 protein.

All of the references cited above, as well as all references cited herein, are incorporated herein by reference in their entireties.

The following examples are offered by way of illustration and not by way of limitation.

EXAMPLES

Example 1: Exosome-Encapsulated STING Agonists

Encapsulation of STING Agonist 1 mM STING agonist including ML RR-S2 CDA ammonium salt (MedChem Express, Cat. No. HY-12885B) and (3-3 cAIMPdFSH; InvivoGen, Cat. No. tlrl-nacairs) was incubated with purified exosomes (1E12 total particles) in 300 ul of PBS at 37 °C overnight. The mixture was then washed twice in PBS and purified by ultra-centrifugation at 100,000×g.

Modeling Final Concentration after Incubation

Exosomes expressing Scaffold X (CB-101) were prepared and incubated with CP-201. A model to predict the final CP-201 concentration after chromatography was designed based on the initial CB-101 and CP-201 concentration parameters, and are shown in Table 3. Sample engineering batches were tested and Table 4 and Table 5 show the results of CP-201 loading followed by chromatography cleanup.

TABLE 3

| | | p/mL CB-101 during loading | | | | | | | | | | | |
|---|---|---|---|---|---|---|---|---|---|---|---|---|---|
| | | 1.20E+13 | 1.10E+13 | 1.00E+13 | 9.00E+12 | 8.00E+12 | 7.00E+12 | 6.00E+12 | 5.00E+12 | 4.00E+12 | 3.00E+12 | 2.00E+12 | 1.00E+12 |
| g/L | 2.22 | 7.07 | 6.48 | 5.88 | 5.29 | 4.70 | 4.10 | 3.51 | 2.92 | 2.32 | 1.73 | 1.14 | 0.54 |
| CP-201 | 1.85 | 6.05 | 5.55 | 5.04 | 4.53 | 4.02 | 3.51 | 3.01 | 2.50 | 1.99 | 1.48 | 0.97 | 0.47 |
| during | 1.48 | 5.04 | 4.61 | 4.19 | 3.77 | 3.35 | 2.92 | 2.50 | 2.08 | 1.65 | 1.23 | 0.81 | 0.39 |
| loading | 1.11 | 4.02 | 3.68 | 3.34 | 3.01 | 2.67 | 2.33 | 1.99 | 1.66 | 1.32 | 0.98 | 0.65 | 0.31 |
| | 0.74 | 3.00 | 2.75 | 2.50 | 2.24 | 1.99 | 1.74 | 1.49 | 1.24 | 0.99 | 0.73 | 0.48 | 0.23 |

TABLE 4

| | Min | Max | Target |
|---|---|---|---|
| Loading CB-101 (p/mL) | 5.5E12 | 8.5512 | 7.0E12 |
| Loading CP-201 (g/L) | 1.85 | 2.22 | 2.04 |
| CP-201 in DP (ug/mL) | 2.75 | 5.00 | 3.81 |

TABLE 5

| | Min | Max | Target |
|---|---|---|---|
| Loading CB-101 (p/mL) | 3.5E12 | 6.5E12 | 5.0E12 |
| Loading CP-201 (g/L) | 1.85 | 2.22 | 2.04 |
| CP-201 in DP (ug/mL) | 1.74 | 3.81 | 2.71 |

Figure 1:
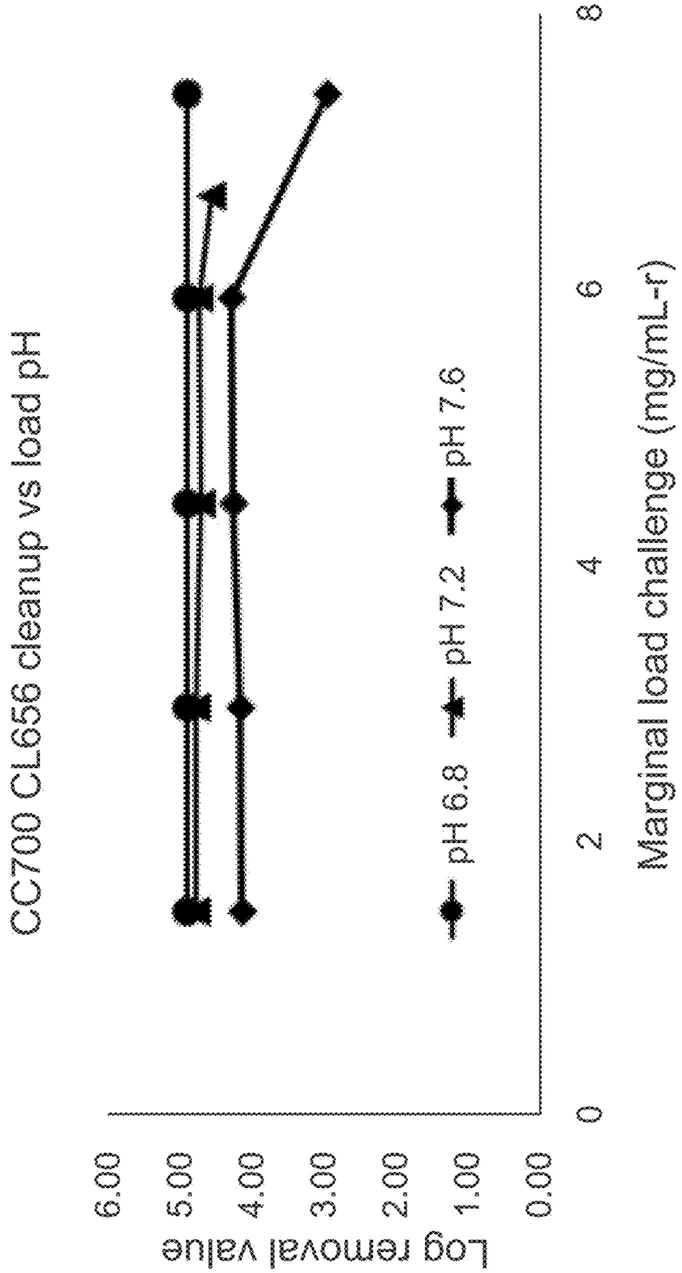
FIG. 1 shows the results of a CaptoCore 700 cleanup process to remove free CDNs with respect to total free CDN removal as compared to load chromatography column pH conditions. The greatest removal in free CDNs was seen in pH 6.8 as compared to pH 7.2 and pH 7.6, and the removal capacity did not decrease as the marginal load challenge increased to about 8 mg/ml-r.
Figure 2:
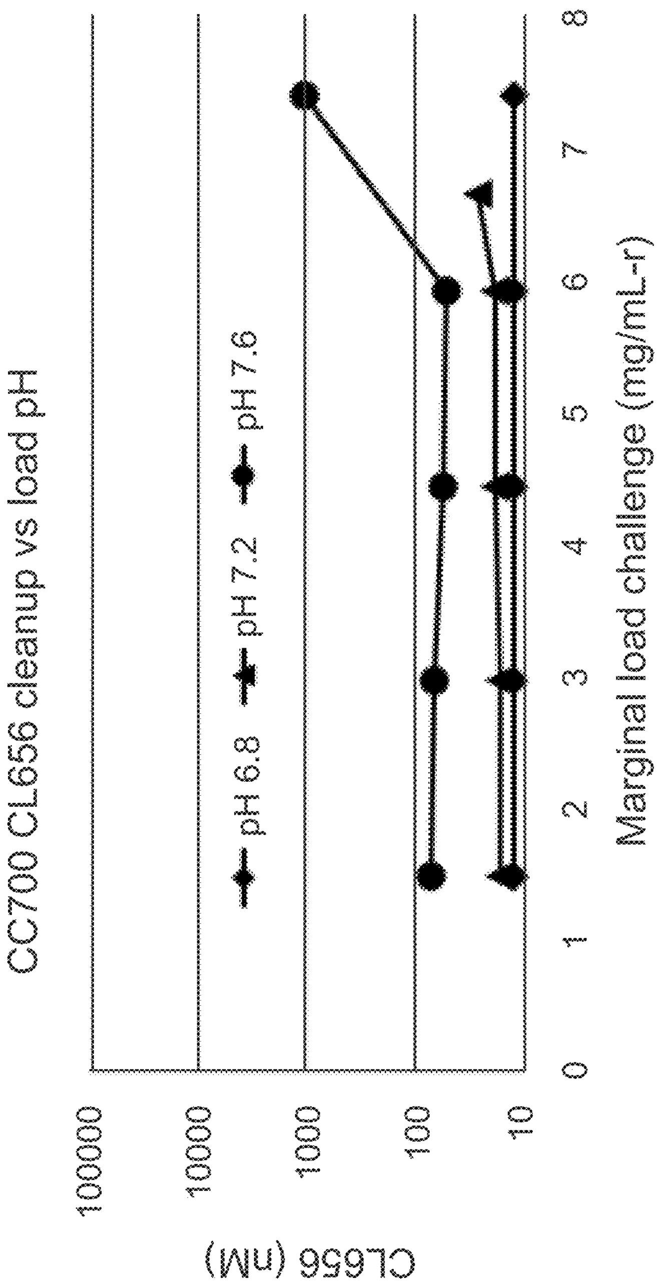
FIG. 2 shows the results of a CaptoCore 700 cleanup process to remove free CDNs with respect to CL656 concentration (nM) as compared to load chromatography column pH conditions. The lowest CL656 concentration was seen in pH 6.8 as compared to pH 7.2 and pH 7.6.
Figure 3:
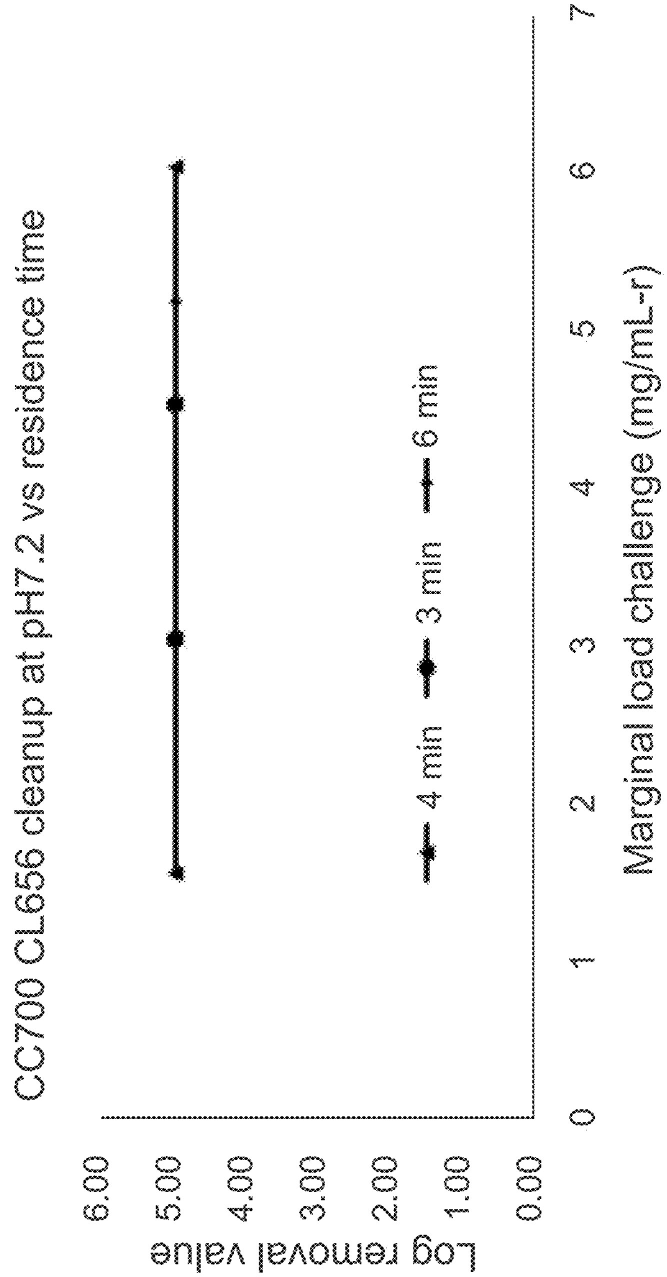
FIG. 3 shows the results of various marginal load challenges (mg/ml-r) and removal of free CDN using various residence times, showing that the residence time on the column does not affect CDN removal.
Figure 4:
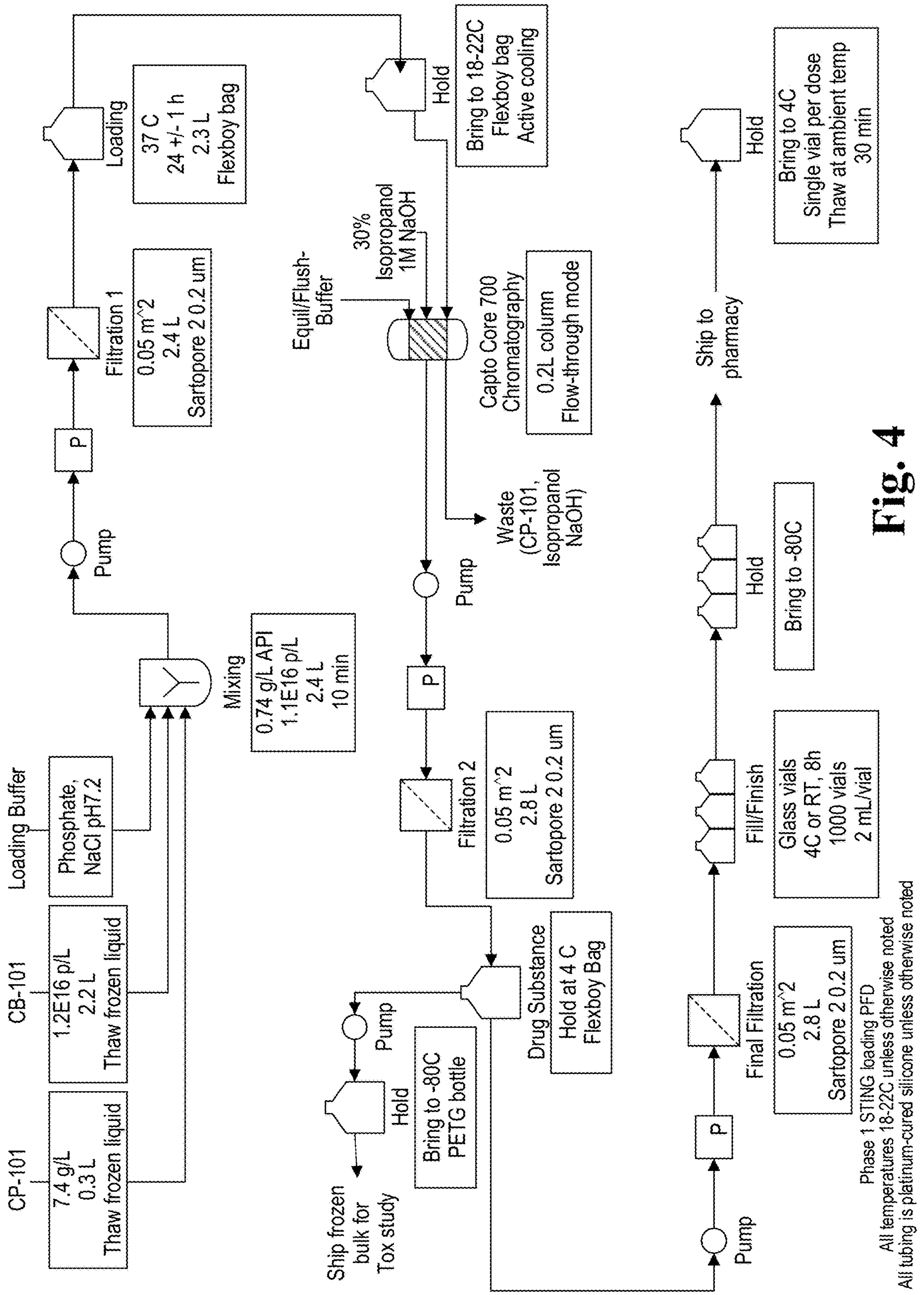
FIG. 4 shows a manufacturing and formulation process for Exosome preparations associated with STING agonists or other cyclic dinucleotides.
Figure 5:
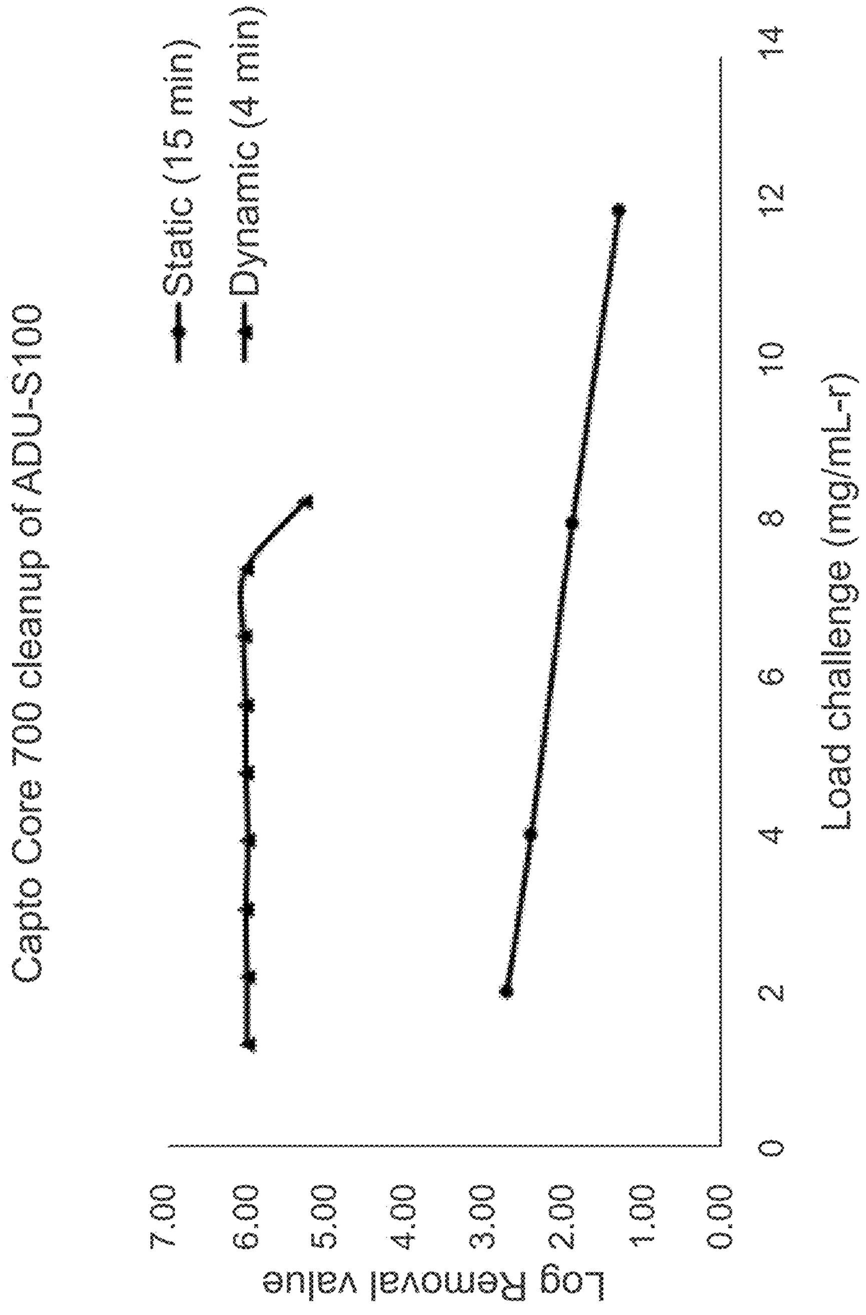
FIG. 5 shows the results of various marginal load challenges (mg/ml-r) and removal of free CDN using various residence times of a known STING agonist ADU-S100 (static binding capacity vs. dynamic binding capacity). Static binding capacity represents the total load that can be bound by the column independent of separation conditions such as flow rate, and the sample was incubated with the chromatography resin over a period of 15 minutes. Dynamic binding capacity represents the amount of product bound to the column under standard flow conditions. The residence time of the sample in the chromatography column was 4 min. The static capacity was quantified by absorbance measurements, and the dynamic capacity was quantified by LC-MS.
Figure 7:
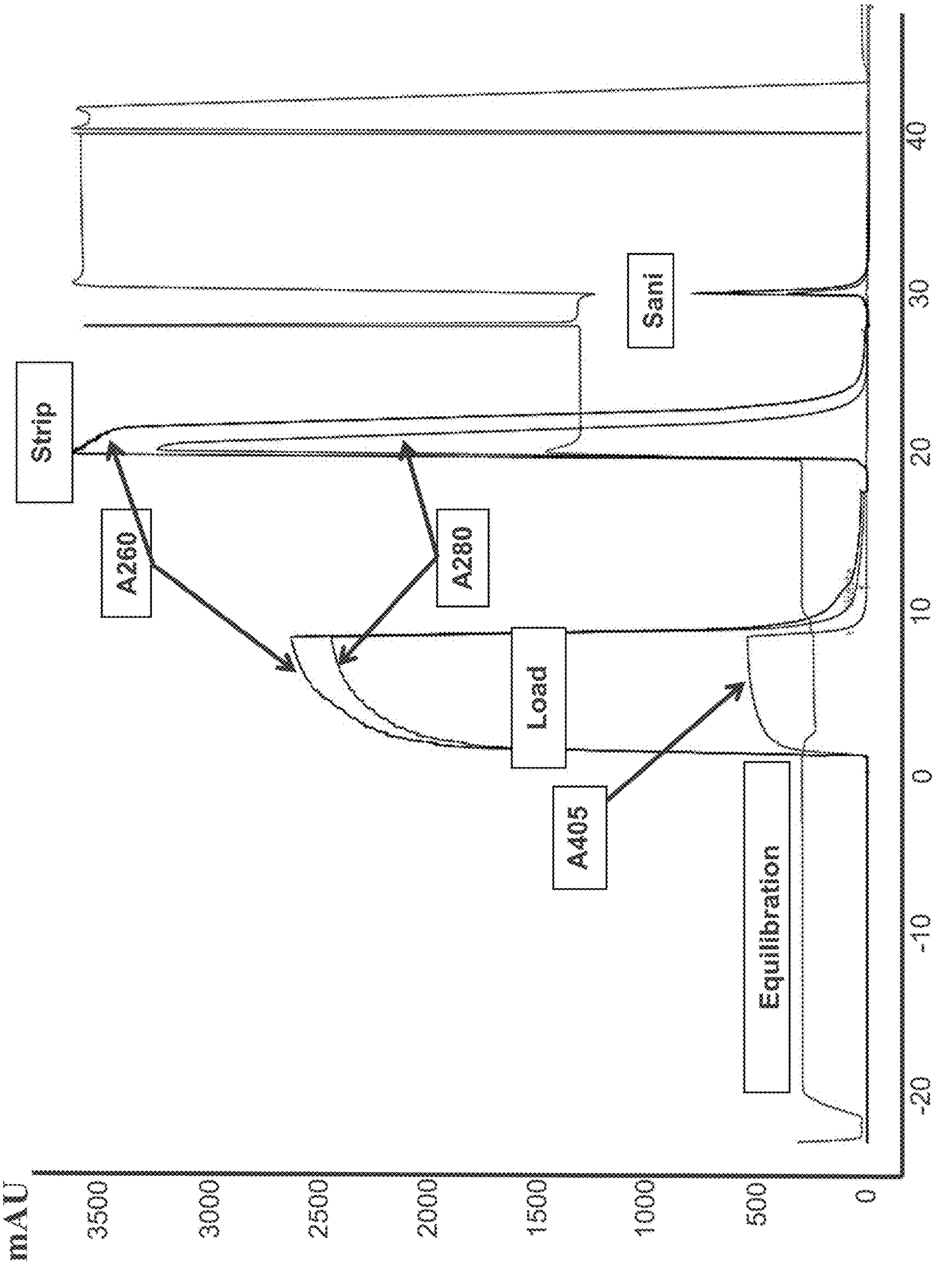
FIG. 7 shows a chromatogram of a CC700 cleanup process for the removal of free CDN and other contaminants. Scaffold X-expressing exosomes were loaded with CL656, and CC700 in flow-through mode was used for the chromatography cleanup step. The load step, which occurs after equilibration, shows absorbances in the 260 nm and 280 nm range, along with the 405 nm range. The A405 absorbance shows exosomes passing through the column. The load phase represents free CDN binding to the column, while exosomes continue to flow through. The free CDN that bound to the column is then eluted in the Strip phase after the exosomes have been removed from the mixture and collected, and a following "Sani" phase is performed to equilibrate and regenerate the column to be used again.
Figure 8:
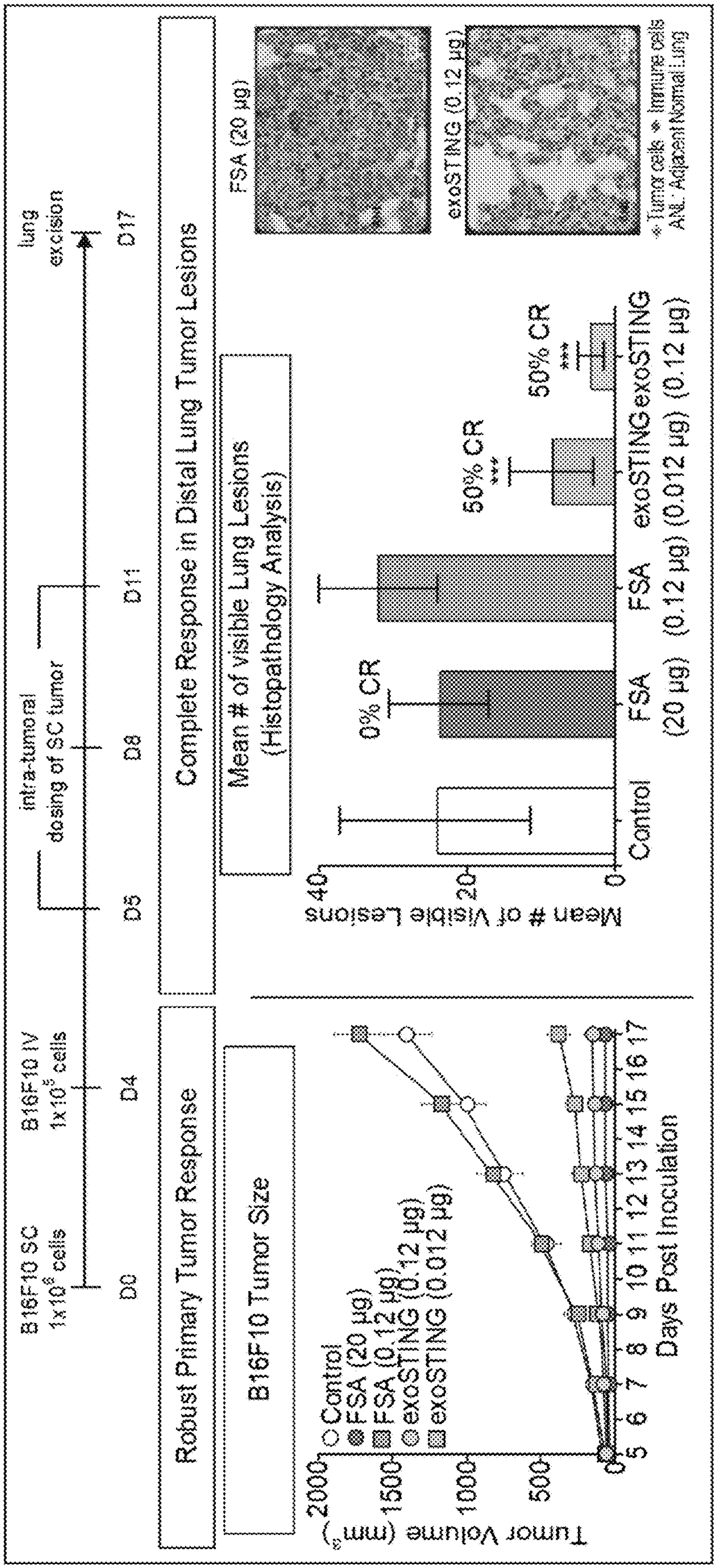
FIG. 8 shows the tumor response in a primary BF16F10 tumor cells and a distal tumor lung lesion as compared to a known anti-tumor agent, FSA, at various concentrations.
Figure 9:
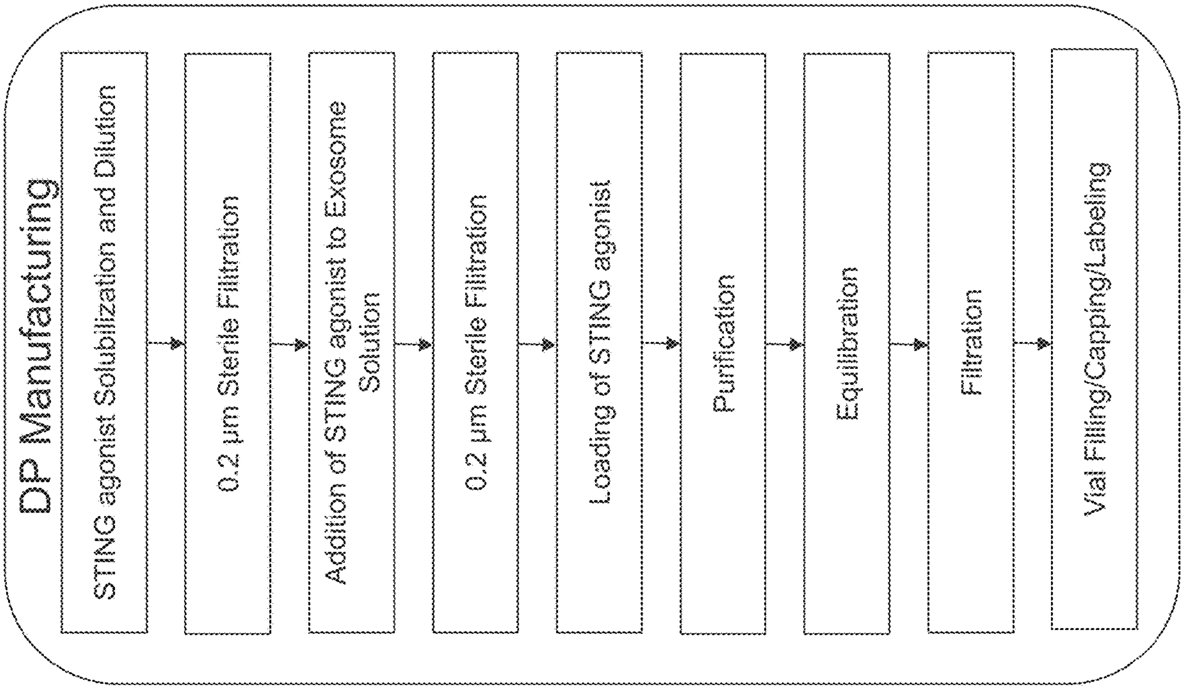
FIG. 9 shows a diagram of an ExoSTING drug product manufacturing process.

Example 2: Multimodal Chromatography Cleanup and pH Dependent Removal of Free CDN During Cleanup Process The EXOSTING cleanup process using a multimodal chromatography CaptoCore 700 column at various column pH conditions was tested based on a comparative load challenge ranging from about 2 mg/ml-r to about 8 mg/ml-r. The greatest removal of free CDN was seen at pH 6.8, with a log removal value of approximately 5.00, shown in FIG. 1. The marginal load challenge as compared to CL656 concentration is shown in FIG. 2. Additionally, the cleanup process at pH 7.2 is shown based on various load challenge times, showing that the residence time on the column does not affect CDN removal, as shown in FIG. 3. A representative chromatogram of the cleanup process is shown in FIG. 7.

Example 3: Activity Assays

Figure 6:
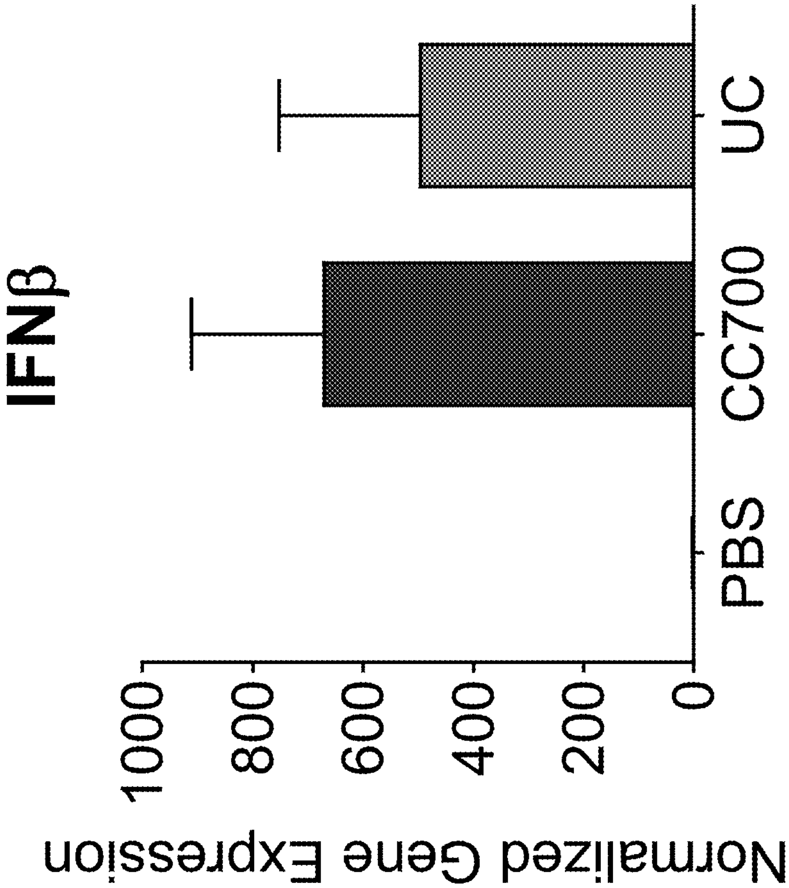
FIG. 6 shows a comparison between the CaptoCore700 (CC700) Cleanup process compared to ultracentrifugation (UC) cleanup showing normalized IFN-β gene expression in B16F10 tumor cells four hours post injection. The CC700 process showed greater in-vivo potency as compared to ultracentrifugation.

Interferon-β expression using ExoSTING after CaptoCore 700 cleanup to remove free CDNs as compared to EXOSTING without cleanup is shown in FIG. 6. ExoSTING preparations subjected to CaptoCore 700 cleanup showed significantly higher gene expression reduction as compared to ExoSTING preparations at the same external CDN concentration without cleanup. A representative ExoSTING cleanup chromatogram using CaptoCore 700 is shown in FIG. 7.

Example 4: Comparative Efficacy of STING Agonist-Loaded Exosomes and Free STING Agonist in B16F10 Tumor Cell Line Tumor cells derived from the B16F10 cell line were subcutaneously implanted into mice, and various samples including PBS, control exosomes, and test samples were subsequently injected intratumorally. exoSTING potency was compared to free STING agonist at various concentrations. The test groups were a control group comprising exosomes without any associated agents, 20 μg FSA, 0.12 μg FSA, 0.12 μg exoSTING, and 0.012 μg exoSTING. exoSTING at both concentrations showed robust effects on tumor volume size post-inoculation, and a reduction in visible lung lesions as well.

Example 5: CP-201 Expression Response for IFN-β and CXCL9 in a Mouse Model

IFN-β and CXCL9 expression and upregulation were evaluated in response to various combinations of exosome and STING agonist incubations. Various concentrations of exosome incubated with STING agonist (CP-201) will be evaluated according to Table 7.

TABLE 7

| Loading Matrix | | EV Concentration (P/mL) 8E12 | 4E12 | 2E12 | 1E12 |
|---|---|---|---|---|---|
| [CP-201] (mM) | 3 | EDD | D | D | EDD |
| | 2 | D | D | D | D |
| | 1 | EE*DD | D | D | EDD |
| | 1 + 40 μM spike in DS | D | D | D | D |

E refers to exosome drug substance intermediate from a 2000 L engineering batch.
D refers to exosome drug substance intermediate from one 50 L development batch.
DD refers to exosomes from two 50 L development batches.

Figure 10A:
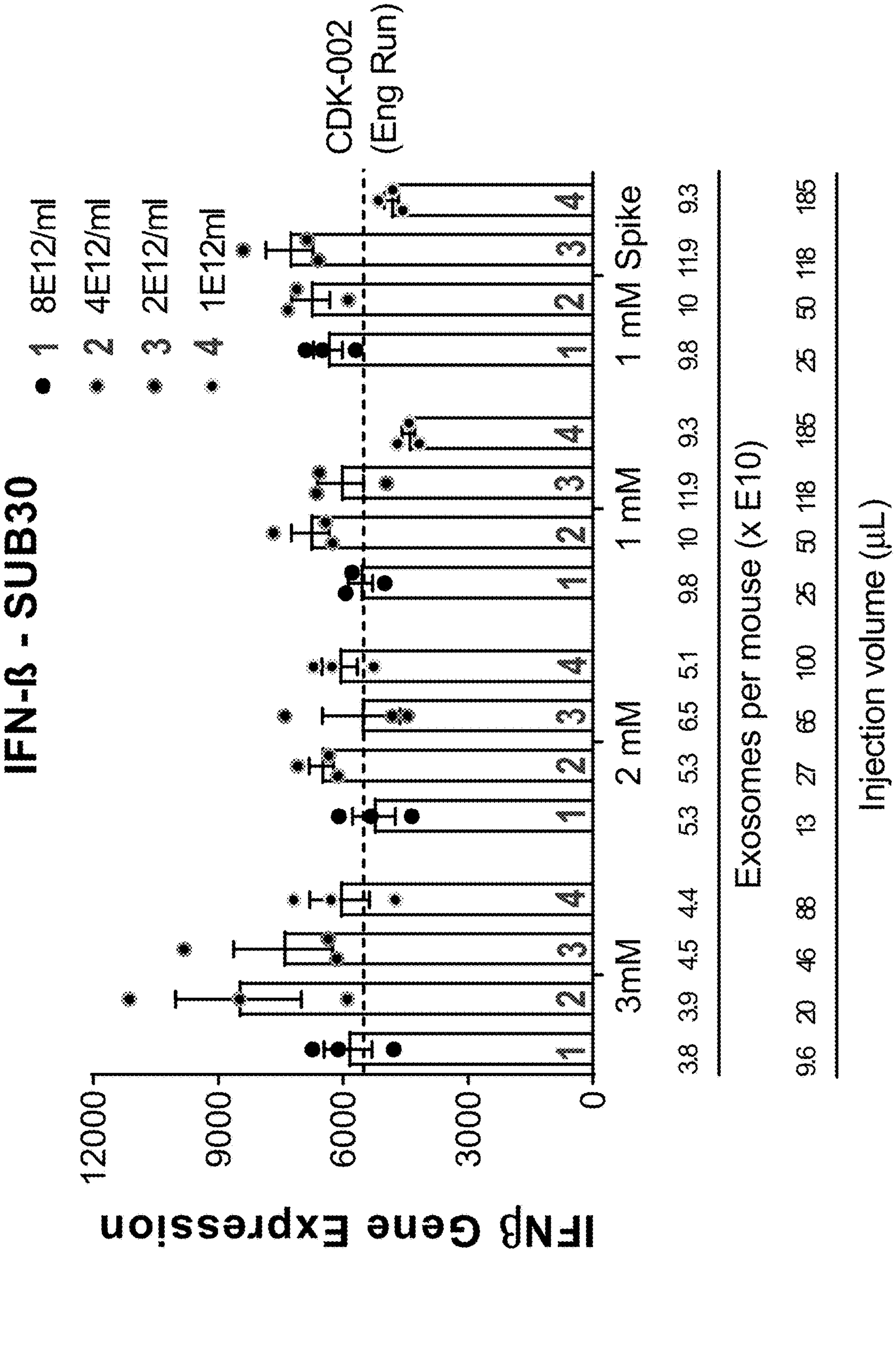
FIGS. 10A-10D.
Figure 10B:
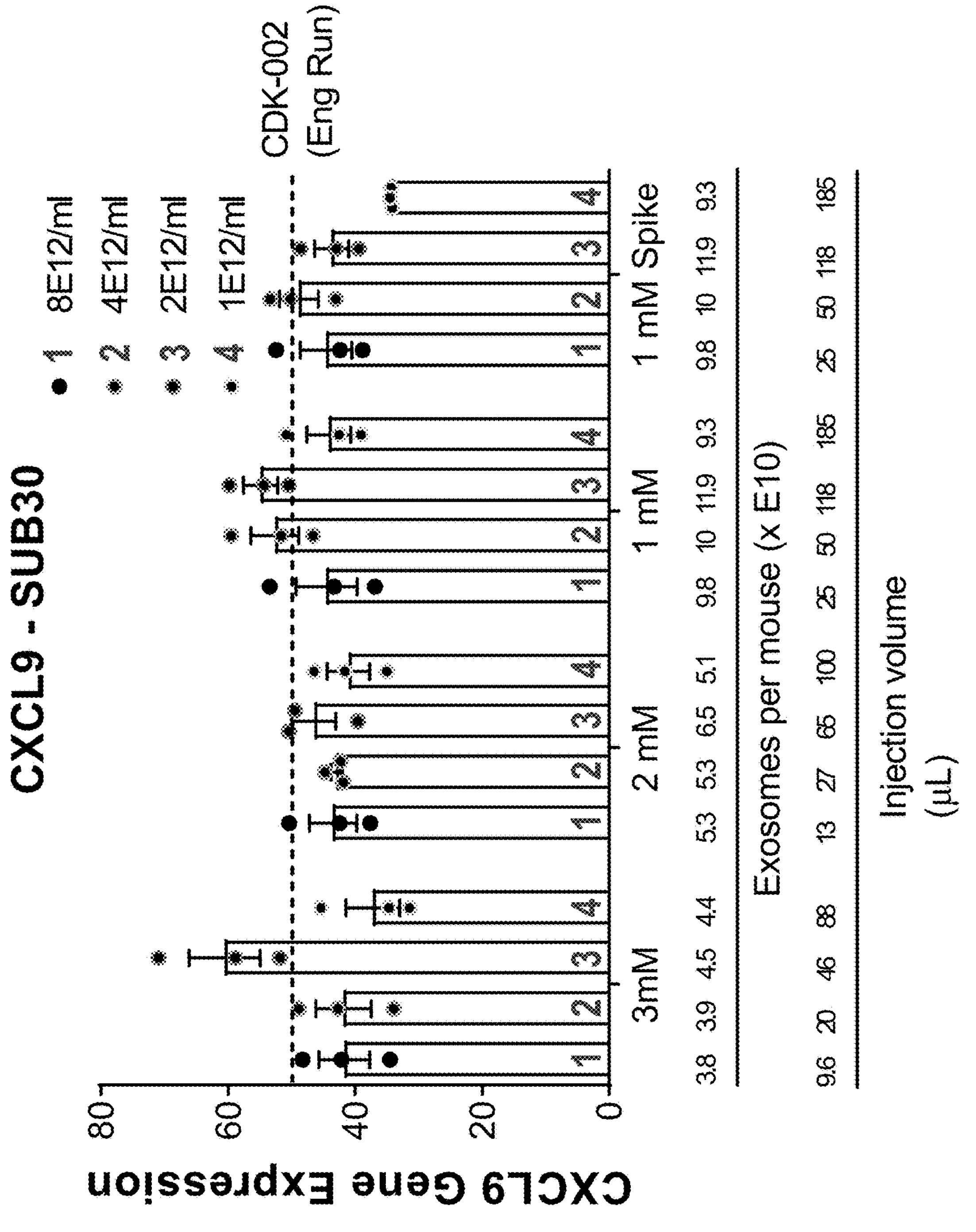
Figure 10C:
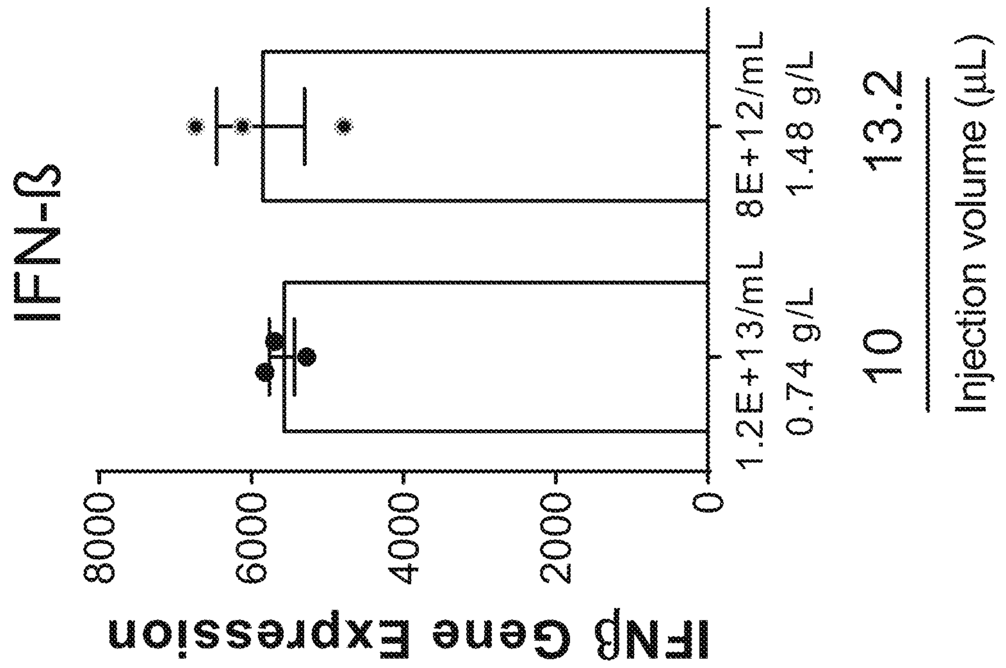
Figure 10D:
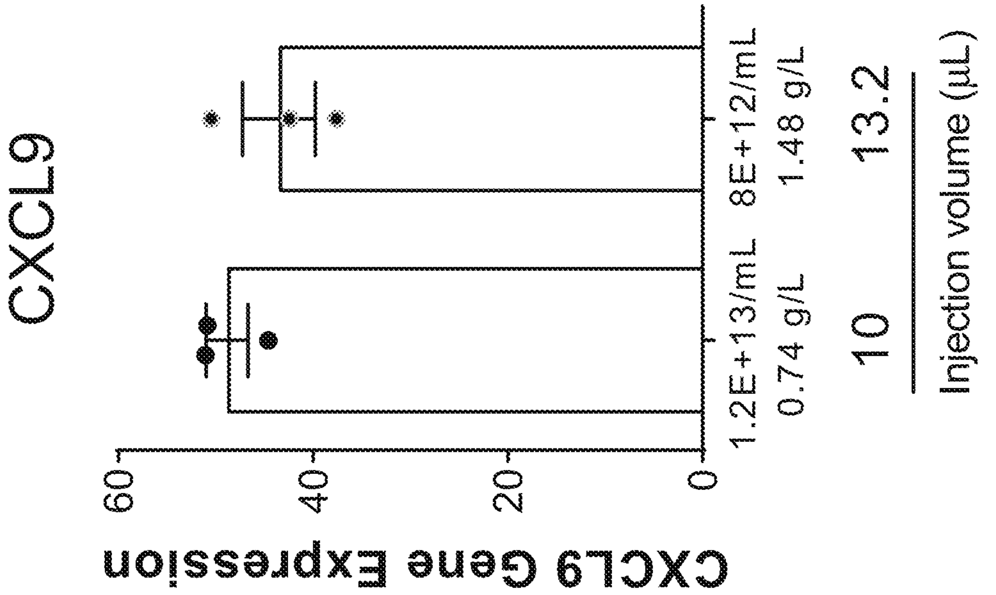
Figure 11A:
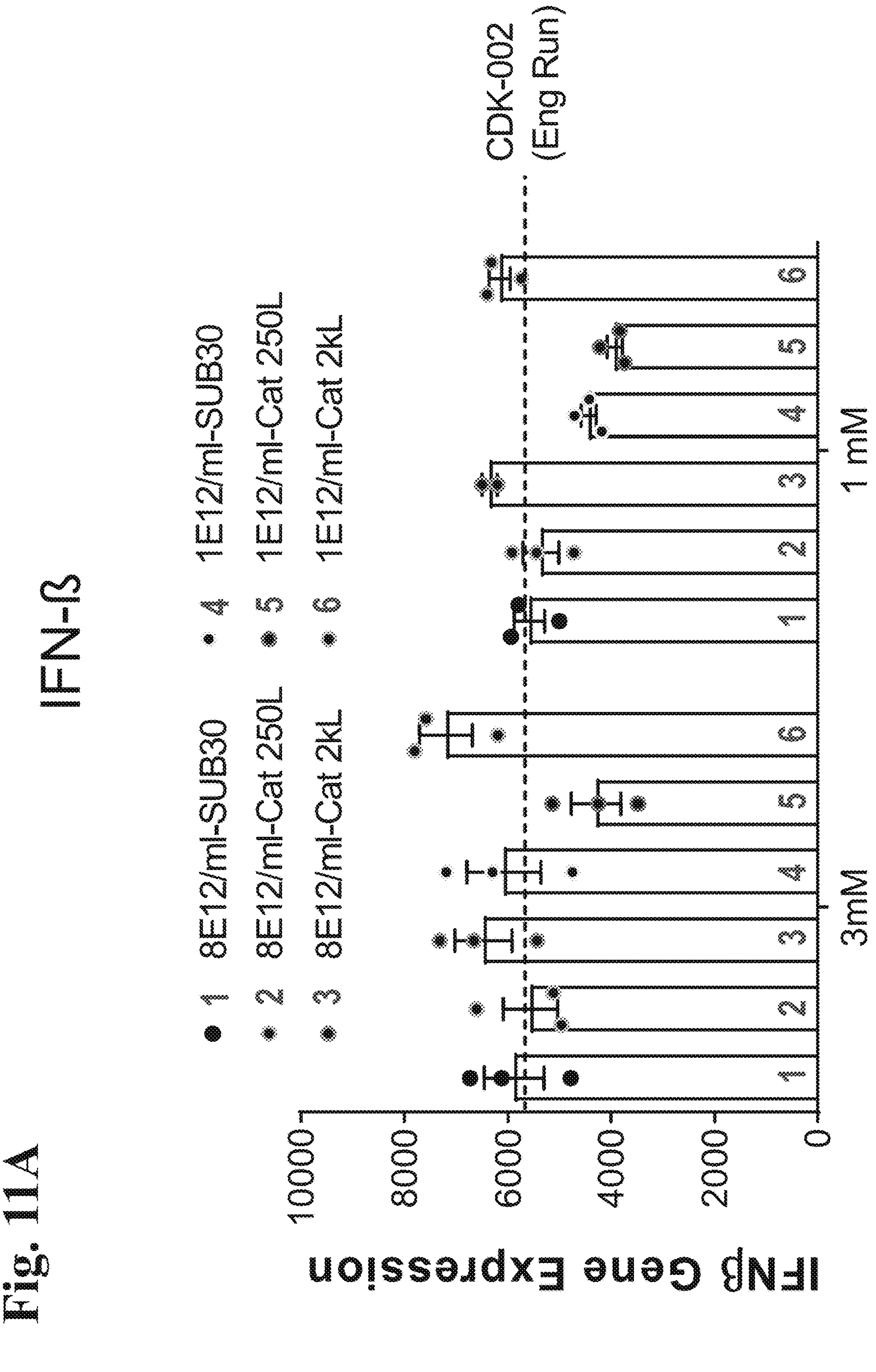
FIGS. 11A and 11B show IFN-β and CXCL9 expression responses across exosome batches. Three production reactor sizes across two exosome concentrations were evaluated, a single use 30 L bioreactor (SUB30) batch, a 250 L batch and a 2,000 L batch at exosome concentrations of both 8E12/mL and 1E12/mL and STING agonist (CP-201) at incubation concentrations of 3 mM and 1 mM. All mice received 20 ng of CP-201 per mouse.
Figure 11B:
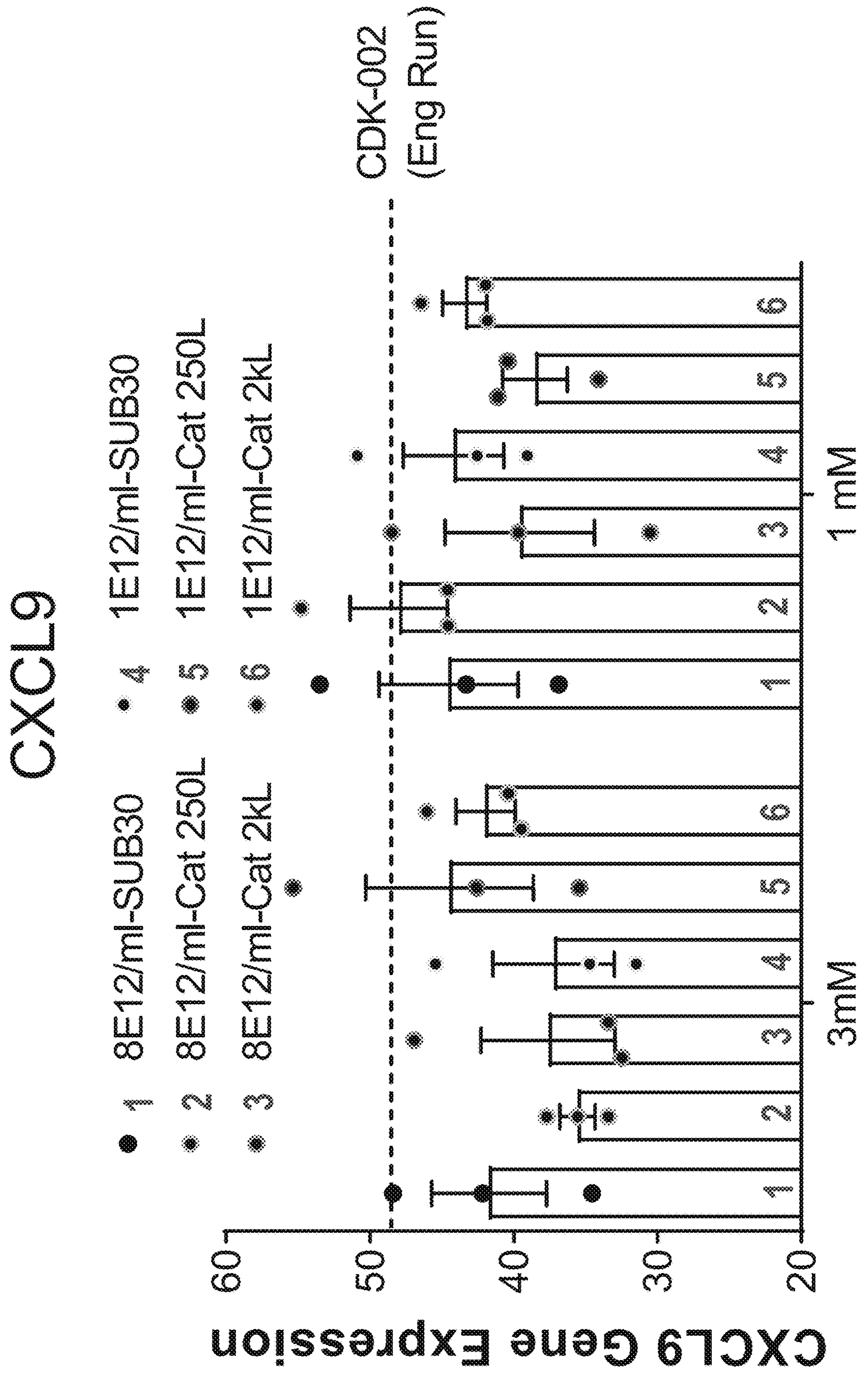

Various concentrations of exosome incubated with STING agonist (CP-201) were dosed in mice intravenously using a single dose at time point 0, followed by measurement of IFN-β and CXCL9 at 4 hours and these data can be seen in FIGS. 10A-10D. FIGS. 10A and 10B. The data points (8E12/ml, 4E12 ml, 2E12/ml and 1E12/ml) represent the concentration of exosome particles incubated with the various concentrations of CP-201. Final concentrations after chromatography cleanup varied, and therefore in order to normalize a dose of 200 ng of CP-201 per mouse, various volumes from each sample were used and are detailed in the Exosomes per mouse (×1010) and injection volume of the sample (μL). In order to normalize delivery volume, the final injection volume was adjusted to 200 μL before injection. Expression of IFN-β and CXCL9 were measured as shown in FIGS. 10C and 10D. Sample 1 had an EV count of 1.2E12/mL, a STING agonist (CP-201) concentration of 0.74 g/L, and an injection volume of 10 μL. Sample 2 had an EV count of 8E12/mL, a STING agonist (CP-201) concentration of 1.48 g/L, and an injection volume of 13.2 μL. 20 ng of CP-201 was delivered per mouse, and the final injection volume was adjusted to 200 μL before injection. Variation in potencies and responses across batches were also evaluated. Three production reactor sizes across two exosome concentrations were evaluated, a 30 L batch, a 250 L batch and a 2,000 L batch at exosome concentrations of both 8E12/mL and 1E12/mL and STING agonist (CP-201) at incubation concentrations of 3 mM and 1 mM. All mice received 20 ng of CP-201 per mouse.

Figures 12A, 12B, 12C, 12D:
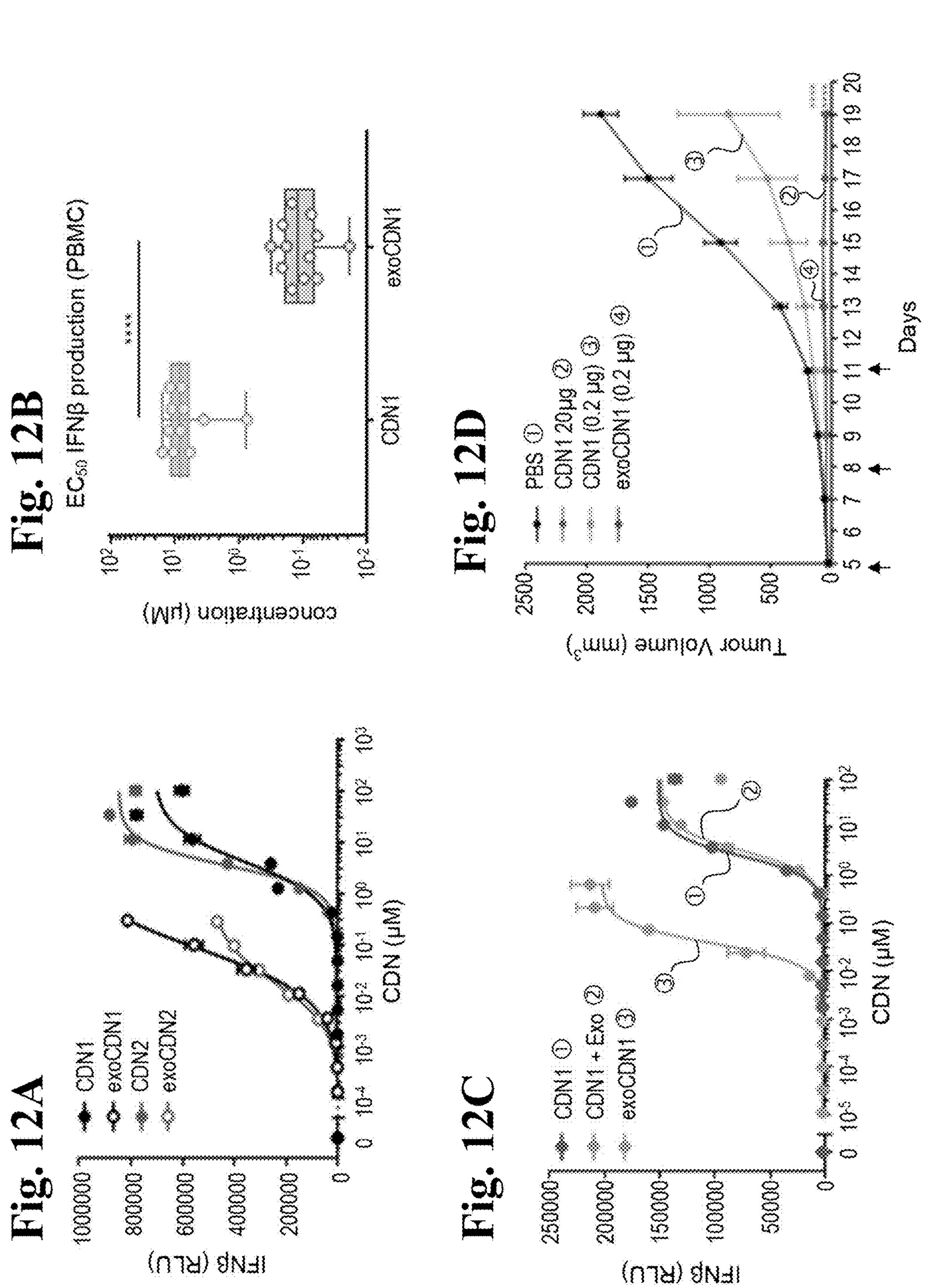
FIGS. 12A-12F show that exoSTING enhances potency of a CDN in vitro and in vivo.

Example 6: Exosome Mediated CDN Delivery Enhances Potency and Anti-Tumor Activity of CDN STING Agonists To test whether exosome mediated delivery of CDN agonist may significantly increase potency and activation of APCs in the TME, we characterized the surface glycoprotein, PTGFRN$^{+/+}$ exosomes loaded with CDN, referred as exoSTING. To determine whether the potency enhancement is observed with different CDNs, we characterized the potency of PTGFRN$^{+/+}$ exosomes loaded with two different CDNs, CDN1 (ML RR-S2, a 2'-3' CDN) or CDN2 (cAIM (PS)2 Difluor, a 3'-3' CDN). Free CDN1 or CDN2 resulted in IFN-β production with an $EC_{50}$~9.7 μM compared to an $EC_{50}$~0.1 μM for CDN1 or CDN2-loaded exosomes (FIG. 12A). Similar $C_{max}$ values were observed with free CDN and exosome-loaded CDN; however, exoSTING was more potent than free CDN. Similar improvements in potency (~100-fold lower $EC_{50}$) were observed with exosomes loaded with CDN1 across multiple donors (n=12; FIG. 12B).

Next, we determined if loading of CDNs into exosomes is required for enhancement of potency. We compared the activity of co-administered exosomes and free CDN with exoSTING in in vitro PBMC assays. The results showed that $EC_{50}$ values for IFN-β production was similar between free CDN (2.5 μM) and co-administered exosomes with free CDN (3.1 μM), whereas exoSTING showed ~100-fold improvement in potency ($EC_{50}$~0.03 μM) (FIG. 12C). These data demonstrate that loading of CDN into exosomes is required for the observed enhancement of potency.

To assess the distinct immune cell subsets activated by free CDN or exoSTING, we evaluated immune cell activation markers by flow cytometry in the in vitro PBMC assay. CD86 expression was assessed as a cell activation marker for DCs and monocytes, whereas CD69 was used as an activation marker for T cells, NK cells, and B cells. Both cDCs and monocytes are predominant class of APCs in PBMCs. ExoSTING treatment demonstrated improved potency in activation of APCs. DCs (cDCs) showed maximal activation at much lower doses of exoSTING compared to the free CDN ($EC_{50}$~0.0001 μM vs. $EC_{50}$~1.2 μM). An enhancement in potency of exoSTING versus free CDN was also observed in monocytes. ExoSTING promoted not only an improved potency as measured by $EC_{50}$ but also by $C_{max}$ in DCs. These results were consistent across PBMCs obtained from multiple donors. Among the lymphocytes, both exoSTING and free CDN led to modest induction of CD69 on T cells and NK cells. No marked induction of CD69 was observed in B cells (data not shown). The induction of CD69 in T cell and NK cells by exoSTING is likely indirect due to stimulation by type I IFN (see Shoiw et al., Nature 440, 540-544 (2006), which is incorporated by reference herein in its entirety).

Figure 12F:
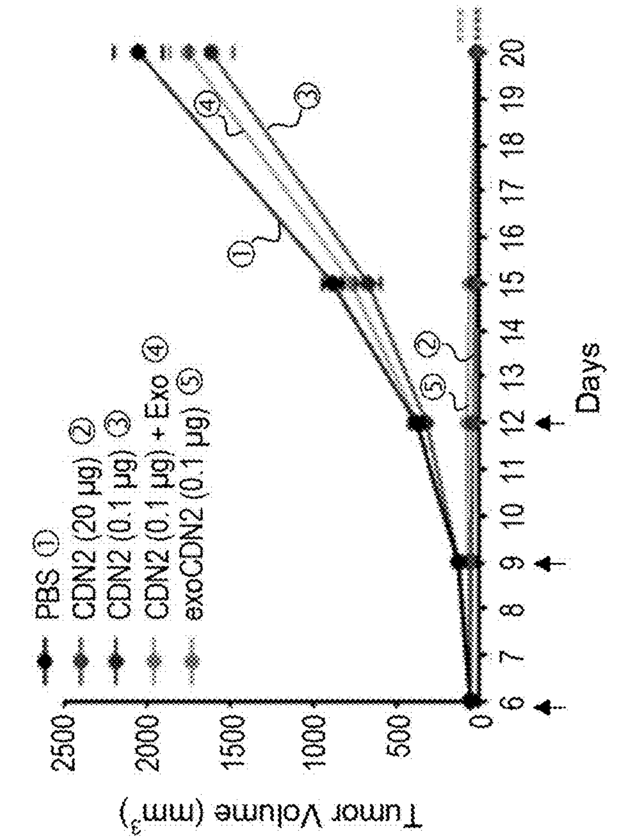
Figure 12E:
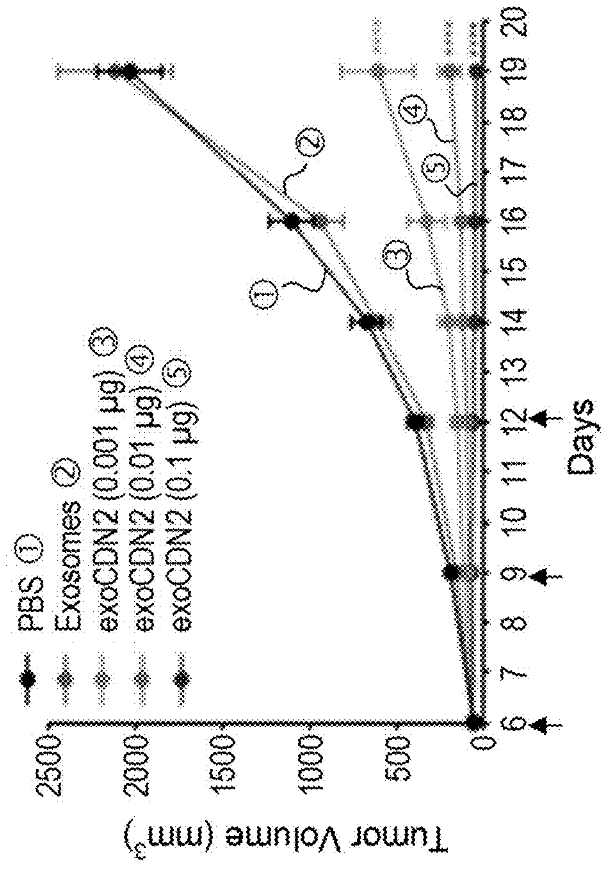

For evaluation of anti-tumor efficacy, we selected B16F10 as a “cold” tumor model that is devoid of T cell infiltration and has been shown to be refractory to checkpoint inhibitor therapy (Ordikhani et al., *JCI Insight* 3, 122700 (2018), Kleffel et al., *Cell* 162, 1242-1256 (2015)). We compared the efficacy of intratumoral (IT) injections of exoSTING and free CDN to determine whether the observed potency enhancements of exoSTING observed in vitro would translate into in vivo tumor models. Our results demonstrated dose-dependent tumor growth inhibition with exoSTING at doses which were 200 to 300-fold lower than that required for comparable results with free CDN1 or free CDN2 (FIGS. 12D and 12E). Similar enhanced potency of exoSTING compared to free CDN was observed in multiple tumor models including EG7.OVA and CT26.wt tumor. No tumor growth inhibition was observed with empty PTGFRN$^{+/+}$ exosomes demonstrating that the CDN STING agonist is required for in vivo anti-tumor activity (FIG. 12E). This data is consistent with the increased potency on IFN-β induction observed in vitro.

To evaluate if loading of CDNs into exosomes is required for improved anti-tumor activity of exoSTING, we compared the anti-tumor activity of free CDN2 with a mixture of CDN2 and exosomes co-administered in the B16F10 model. Neither free CDN2 (0.1 μg) or co-administered PTGFRN$^{+/+}$ exosomes mixed with free CDN2 (0.1 μg) resulted in measurable tumor growth inhibition (FIG. 12F). In contrast, CDN2 loaded into exosomes (exoSTING, 0.1 μg) resulted in tumor growth stasis. These data demonstrate that loading of STING agonists into exosomes is required for the enhanced potency. These data also demonstrate that empty exosomes do not confer any anti-tumor immunity when administered along with CDN2.

Example 7: exoSTING Treatment Results in Systemic Tumor Growth Control

Figure 13A:
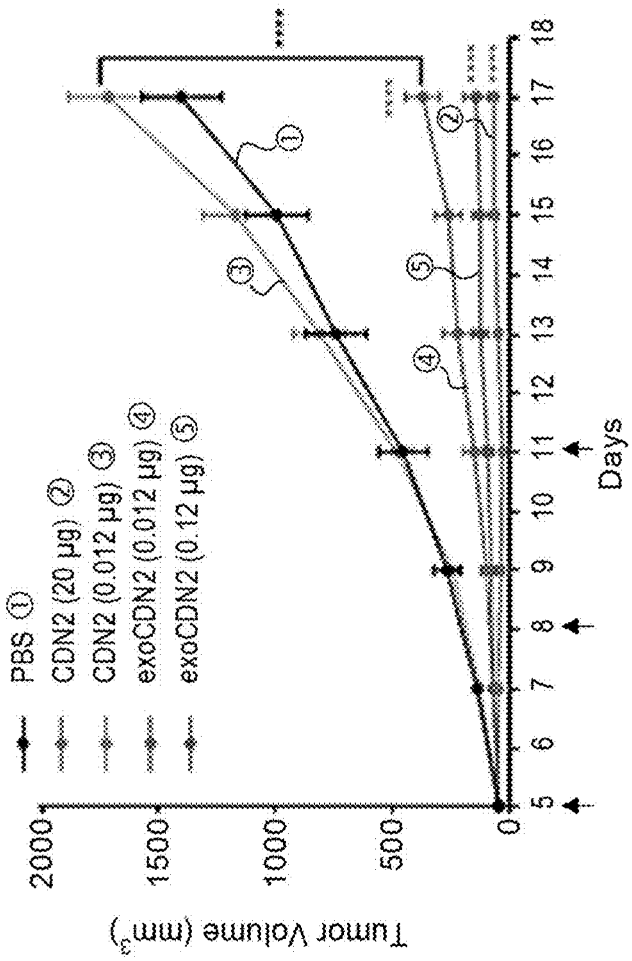
FIGS. 13A-13G show that exoSTING elicits strong anti-tumor responses with systemic tumor-specific immune activation in a B16F10 tumor model.
Figure 13B:
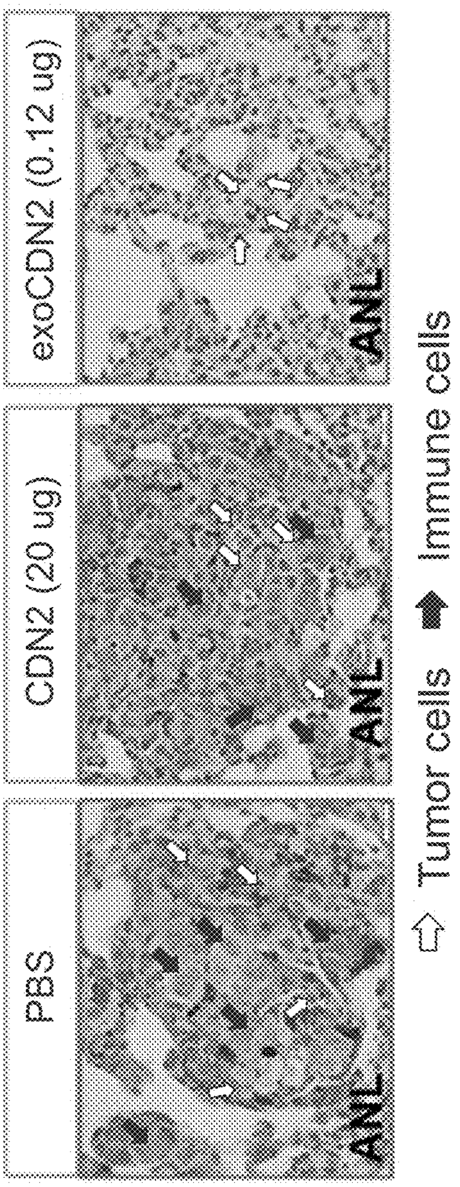
Figures 13C, 13D:
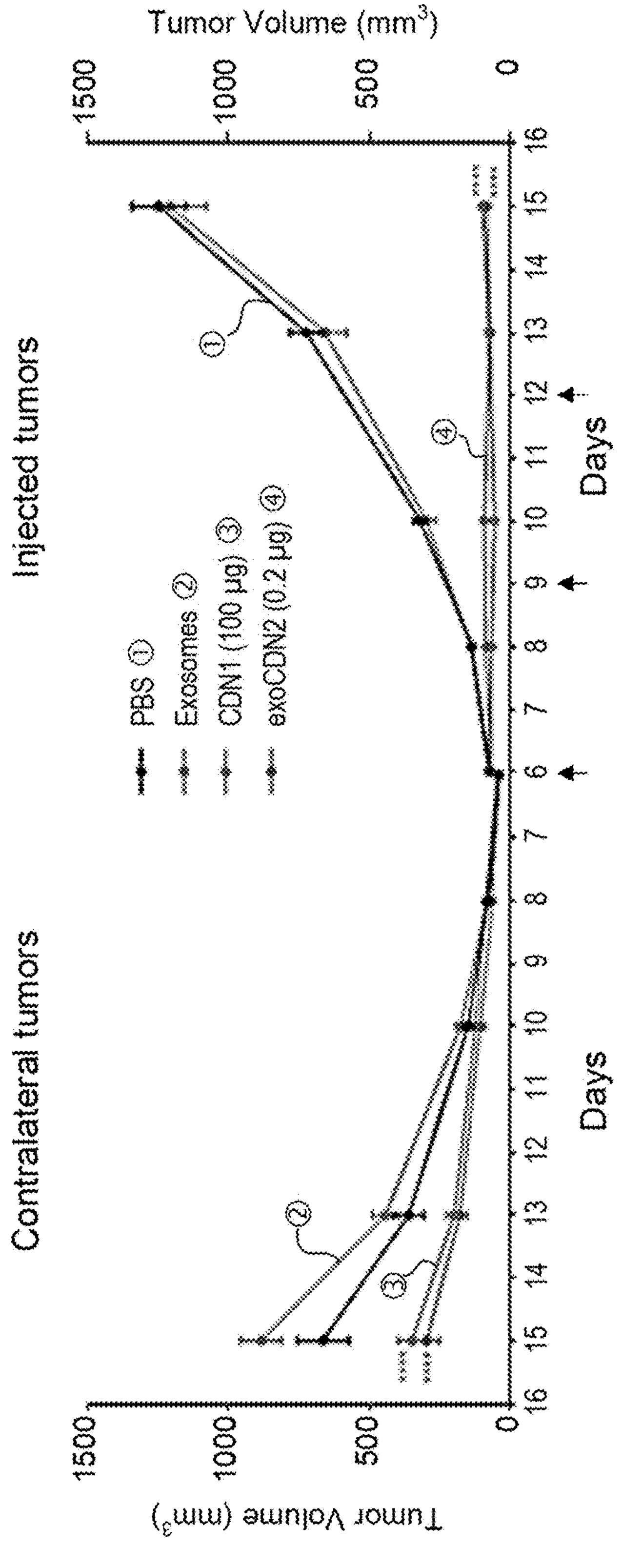

We evaluated animals bearing multiple tumors and compared the ability of exoSTING or free CDN2 to control growth of both the IT injected tumors and non-injected distal tumors. We assessed this abscopal tumor effect in two distinct settings using the B16F10 tumor model. In the first model, a primary B16F10 tumor was inoculated subcutaneously in the flank followed by an intravenous injection of B16F10 on day 4 which lead to the development of distal lung lesions. Tumor growth was assessed at both the injected subcutaneous tumor and the distal lung lesions. High doses of free CDN (20 μg) were required to inhibit the primary tumor in the flank, while primary tumor growth inhibition was observed at low doses of exoSTING, consistent with previous experiments above (>100-fold lower dose, 0.012-0.12 μg, FIG. 13A). The growth of distal lung lesions was quantified by histology at the end of the study. Histological analysis demonstrated that the tumors in the PBS control group showed poor immune cell infiltration (FIG. 13B, left). Mice treated with exoSTING had complete remission (CR) at the injected flank tumors and few tumor lesions in the lung. These animals also had markedly enhanced immune cell infiltrate in the distal lung tumors compared to untreated controls (FIG. 13B, right). Mice treated with high doses of free CDN (20 μg) showed many viable tumors cells with little T cell infiltration in the lung (FIG. 13B, middle). It should be noted that this dose of free CDN (20 μg) completely abrogated primary tumor growth. Importantly, 4 out of 8 mice in the exoSTING group demonstrated a histological CR with no evidence of lung tumors (FIG. 13C). In contrast, only one of eight mice in the high dose free CDN group showed CR. These results confirm that there is both a greater potency with exoSTING at the injected tumor sites than free CDN, and an enhanced capacity to induce a systemic immune response against distant tumors.

Figure 13E:
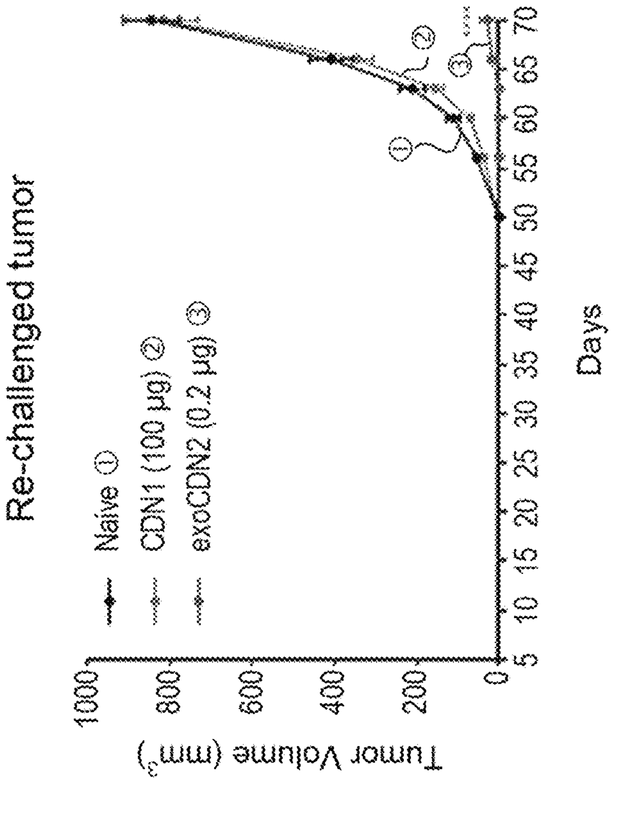

We evaluated exoSTING or free CDN in a second abscopal model by monitoring tumor growth after implanting B16F10 tumors on both flanks and injecting only one tumor. ExoSTING (0.2 μg) injection showed robust inhibition of growth at both the injected and the contralateral non-injected tumors (FIG. 13D). It should be noted that the high dose of free CDN (20 μg) was ineffective in controlling the secondary tumor growth in this model, in agreement with the observed lack of efficacy in the lung model above. Next, we compared the efficacy of a very high dose of free CDN (100 μg) which was required for effective control of both the injected and non-injected tumors (FIG. 13D). This control of secondary tumors could be either due to the establishment of systemic T cell immunity or due to the systemic leakage of and exposure to the free CDN in the distal non-injected tumor. In order to distinguish between these two different mechanisms, we evaluated immunological memory response using a B16F10 re-challenge model. B16F10 tumor bearing mice were treated with doses of either exoSTING (0.2 μg) or free CDN (100 μg) as described above. Both treatments resulted in tumor growth control of the primary injected tumor. Persistent tumor growth control was monitored over a period of 50 days. Complete remission was observed in one-third of the mice treated with exoSTING. In contrast, the free CDN (100 μg) resulted in complete remission in 80% of the mice. Mice that showed complete remission were subsequently re-challenged on the opposite flank with a second inoculation of B16F10 tumor cells on day 50. No tumor growth was observed upon tumor challenge with B16F10 cells in the exoSTING treated group up to day 70 (FIG. 13E); however, tumor growth was observed in all of the mice which were previously treated with free CDN demonstrating a lack of immunological memory (FIG. 13E). These data suggest that local and systemic anti-tumor activity of free CDN and exoSTING may be mediated by distinctly different mechanisms.

Figure 13F:
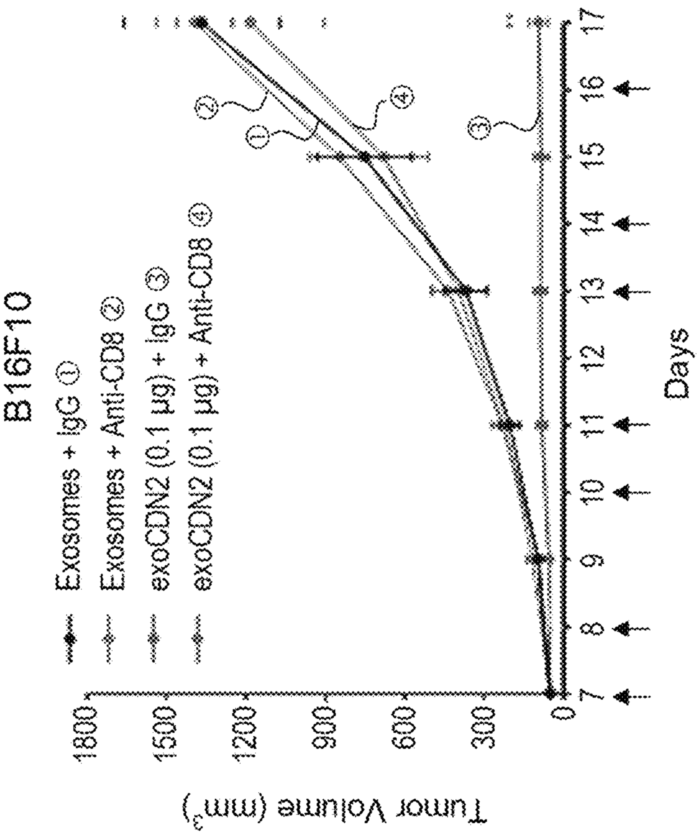

Example 8: Generation of Tumor Antigen Specific CD8 T Cell Dependent Systemic Anti-Tumor Immunity by exoSTING In Vivo To determine the requirement of different innate and adaptive immune cell types in exoSTING-mediated anti-tumor activity, we depleted CD8+ T cells, NK cells, and tumor-associated macrophages. CD8+ T cells play a central role in mediating anti-tumor immunity by exoSTING and free CDN as demonstrated by the abrogation of anti-tumor activity following selective antibody-mediated depletion of these cells (FIG. 13F). Tumor growth inhibition with exoSTING was not affected by NK cell depletion with anti-NK1.1 antibody treatment (data not shown). Therefore, NK cells did not appear to be required for anti-tumor activity. Depletion of tumor-associated macrophages by anti-CSFIR antibody treatment resulted in 50% tumor growth inhibition, demonstrating that tumor resident macrophages also play a role in mediating anti-tumor responses to STING activation by exoSTING (data not shown). These results demonstrate the essential role of CD8+ T cells and macrophages in the anti-tumor activity of exoSTING.

Figure 13G:
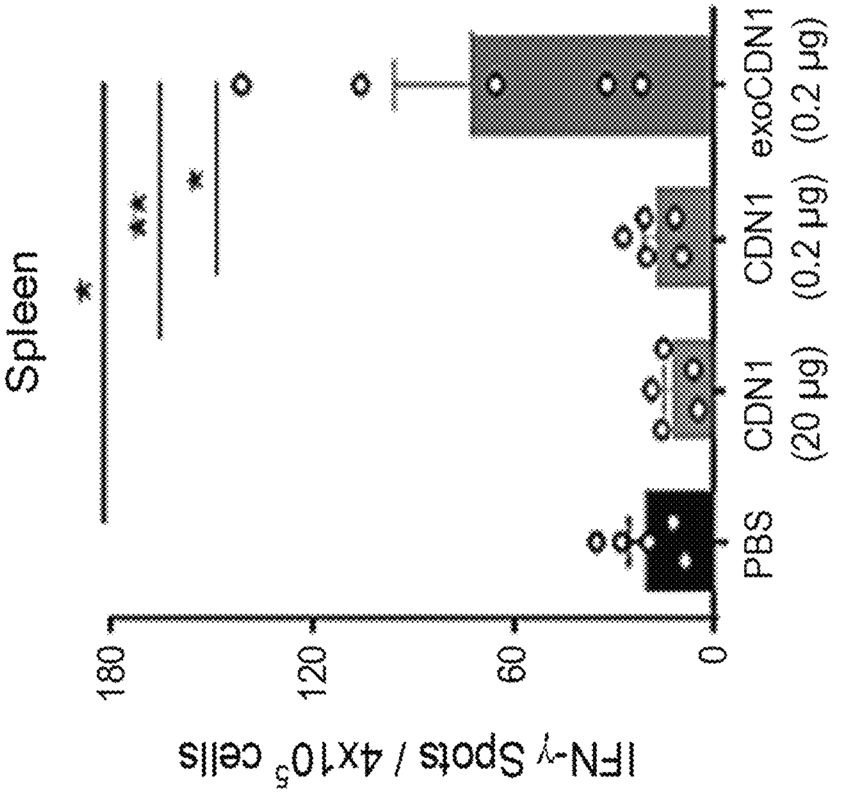

We next evaluated the capacity of exoSTING to induce systemic, antigen specific T cell responses in the B16F10 tumor model. Several tumor-associated CD8-dependent antigens have been identified as dominant antigens from B16F10 tumor cells (Kreiter et al., Nature 520, 692-696 (2015), which is incorporated by reference herein in its entirety). We used an equimolar mixture of the epitope peptides (Trp2, GP100 & Tyr) to stimulate tumor antigen-specific T cell responses by assessing IFN-γ production in splenocytes following two IT doses of exoSTING or free CDN1. At day 4, 24 hours after the second dose, exoSTING demonstrated a 3- to 4-fold increase in the number of IFN-γ positive spots as compared to the PBS control (FIG. 13G). The equivalent dose of free CDN1 (0.2 μg) or the efficacious dose (20 μg) failed to induce IFN-γ positive spots as compared to the PBS control. These data demonstrate that exoSTING treatment results in robust expansion of tumor antigen-specific T cells in contrast to free CDN, which at the doses used, did not lead to significant expansion of tumor antigen-specific T cells.

Example 9: exoSTING is Retained in Tumors and Significantly Enhances Local IFN-γ Induction and Limits Systemic Inflammation A major limitation of IT administration of free CDN is its rapid dissemination into the systemic circulation (see Sivick et al., *Cell Rep.* 25, 3074-3085.e5 (2018)). This results in systemic STING activation and inflammatory cytokine production, but also limits STING activation in the TME. This reduces the effectiveness of the CDN to elicit a productive immune response in the tumor resulting in higher doses of free CDN required for efficacy. In B16F10 tumors after injection of exoSTING or free CDN, we measured the amount of CDN in tumors and blood over time. The pharmacokinetic parameters from the study are summarized in Table 8.

TABLE 8

Pharmacokinetic Parameters in Injected Tumor Samples.

| Parameter | exoCDN2 (0.3 μg) | CDN2 (0.3 μg) | CDN2 (30 μg) |
|---|---|---|---|
| $C_{max}$ (ng/mL) | 1,790 | 1,240 | 13,800 |
| AUC (ng · hr/mL) | 7,510 | 799 | 97,300 |
| $T_{1/2}$ (hours) | 2.9 | 0.620 | 2.05 |
| CL (mL/hr) | 0.0399 | 0.375 | 0.308 |

Figure 14A:
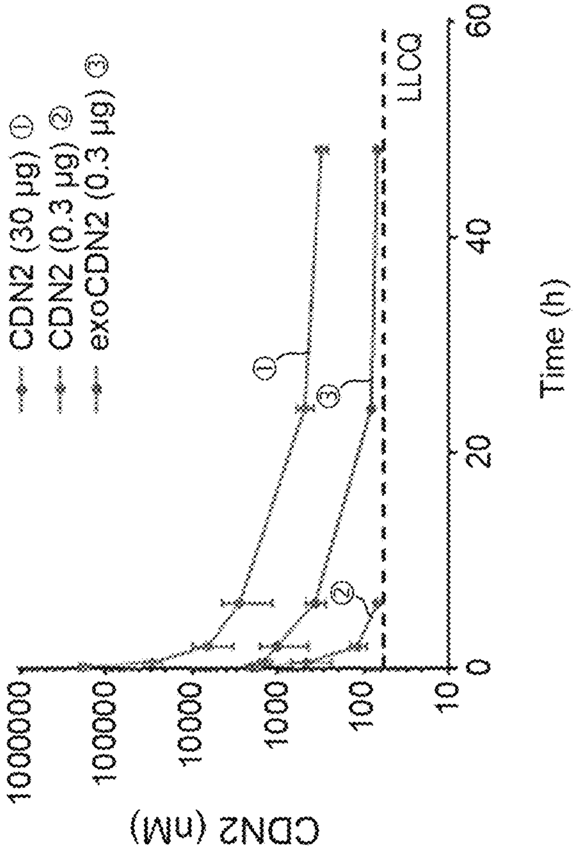
FIGS. 14A-14H show that intra-tumoral administration of exoSTING enhances pharmacokinetics of a CDN and immunostimulatory activity in the tumor microenvironment. C57BL/6 mice were implanted subcutaneously with $1\times10^6$ B16F10 cells.
Figure 14B:
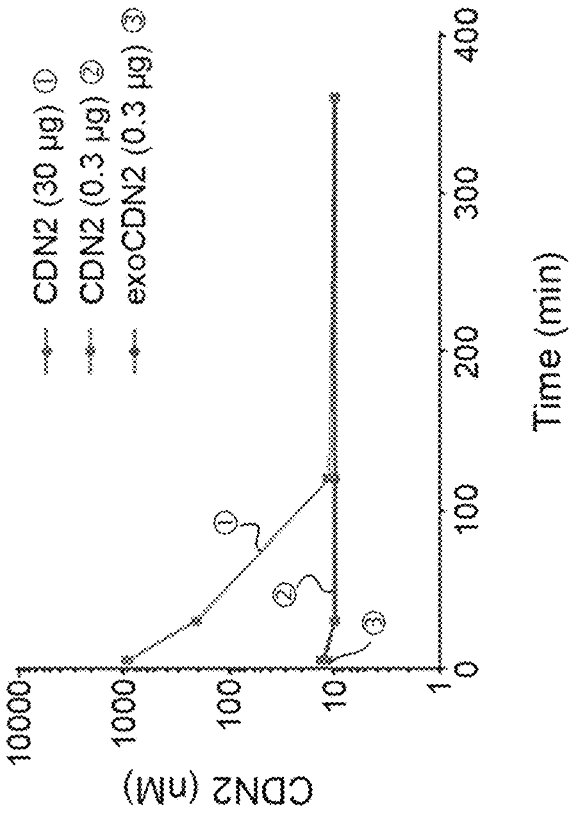

Although both exoCDN2 and dose matched free CDN2 had a similar maximum concentration ($C_{max}$), the area under the concentration-time curve (AUC) of exoSTING is approximately 10-fold higher, the half-life ($T_{1/2}$) is longer (4.7-fold), and clearance is slower (~10 fold), demonstrating better tumor retention of exoSTING as compared with an equivalent dose of free CDN2 (FIG. 14A). At the 30 μg dose, free CDN2 also showed rapid clearance from the injected tumor and was detectable in the plasma at the 30-minute timepoint. Further, free CDN2 is cleared rapidly in the systemic circulation (106 mL/hr). In contrast, exoSTING at the therapeutically active and maximum feasible dose (0.3 μg) was just above the lower limit of quantitation (LLOQ) of the assay at 5 minutes (9.4 ng/mL) in the systemic circulation and not detectable at 30 minutes (FIG. 14B). These data confirm prolonged tumor exposure and limited systemic exposure observed at the maximal feasible dose with exoSTING.

Figure 14D:
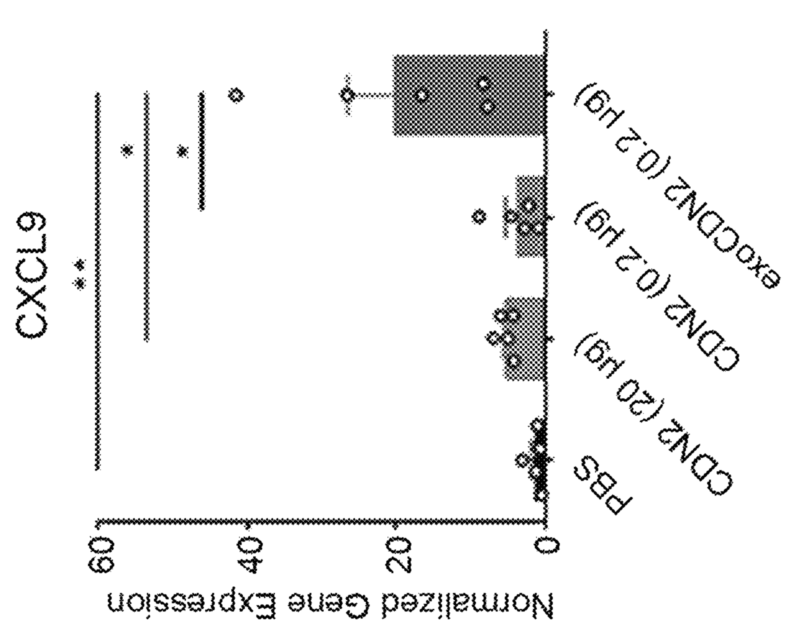
Figure 14C:
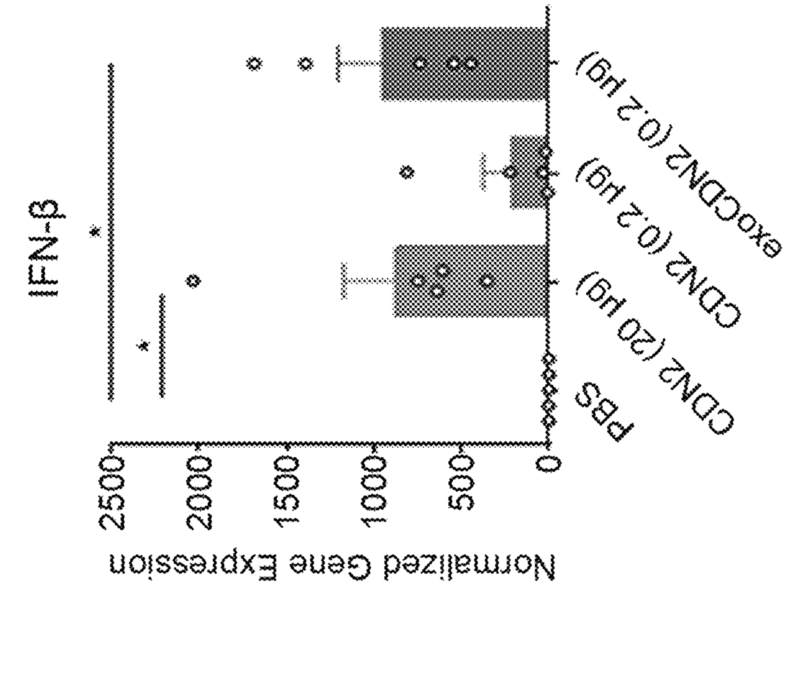
Figure 14F:
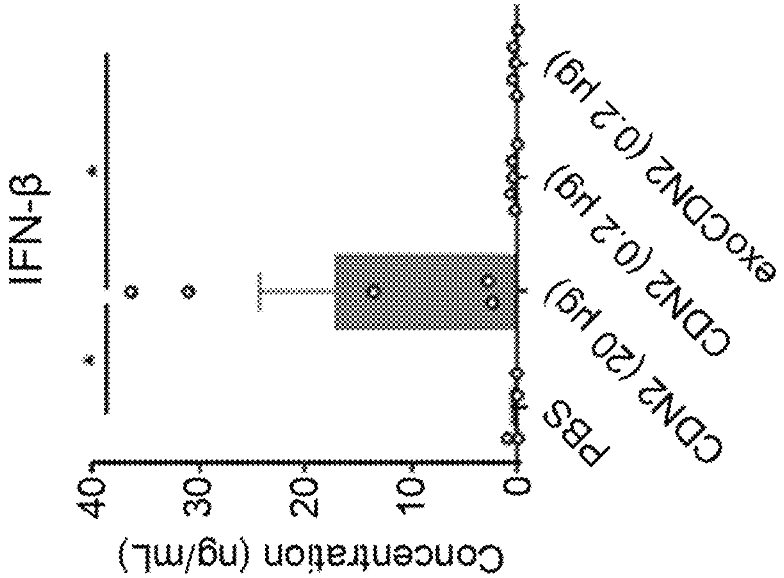
Figure 14E:
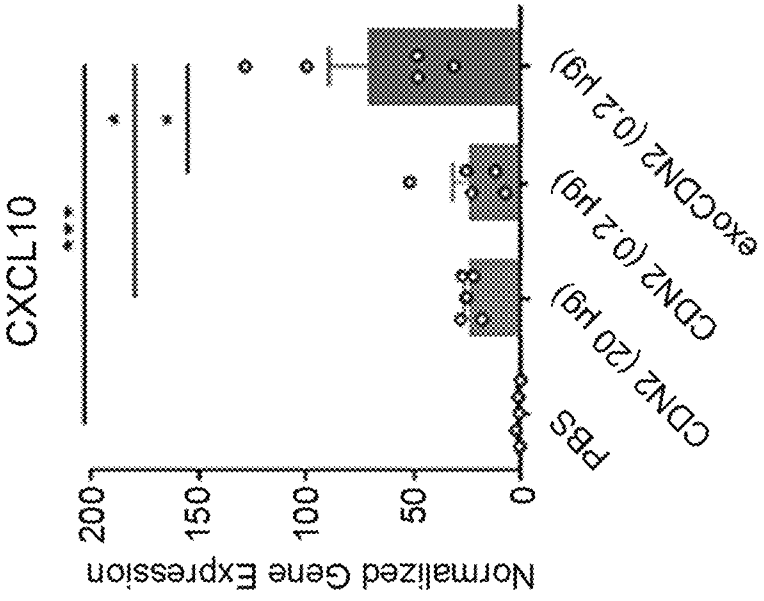

To measure the pharmacodynamic impact of prolonged CDN retention and STING activation in exoSTING injected tumors, we analyzed intra-tumoral mRNA levels of IFN-β, as well as the T cell attractant chemokines CXCL9 and CXCL10 four hours post-injection of exoSTING or free CDN. ExoSTING induced four-fold higher levels of IFN-β in the TME compared to equivalent doses of free CDN. To achieve comparable levels of intra-tumoral IFN-β, free CDN treatment required a 100-fold higher dose than exoSTING (FIG. 14C). ExoSTING also induced substantially higher levels of CXCL9 (5-fold vs free CDN) and CXCL10 (3-fold vs free CDN) mRNA than a comparable amount of free CDN (FIGS. 14D and 14E). Doses of free CDN, even when dosed 100-fold higher than exoSTING, failed to induce comparable mRNA levels of CXCL9 and CXCL10. These data demonstrate tumor retention and sustained IFN-β production by exoSTING in the TME which is required for induction of chemokines essential for T cell recruitment.

Figure 14G:
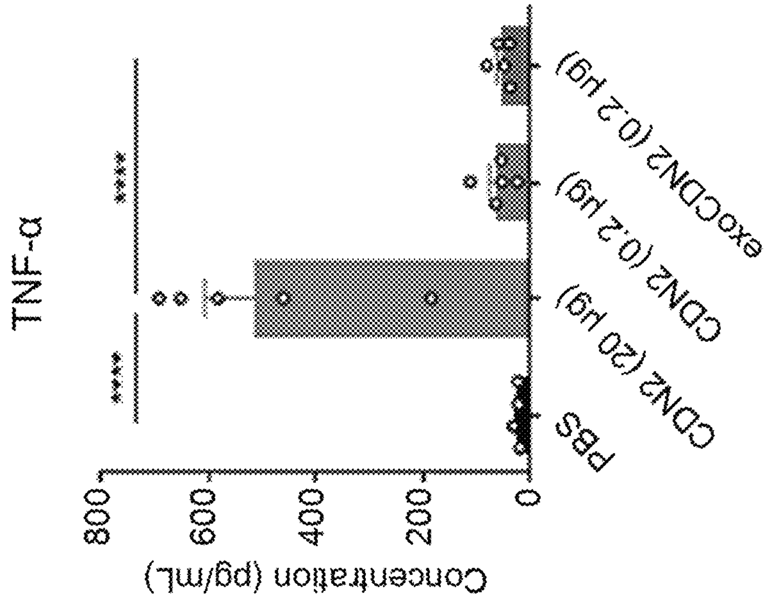
Figure 14H:
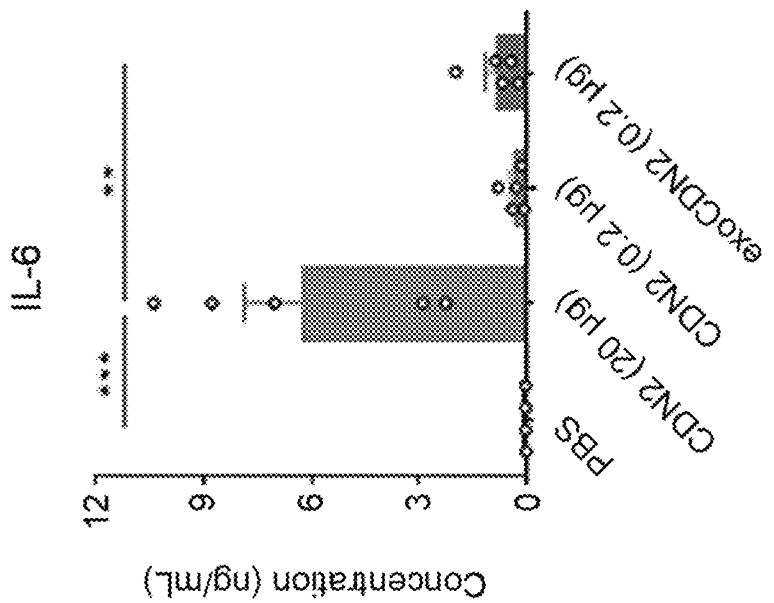

We compared inflammatory cytokine levels in the blood following IT administration of exoSTING or free CDN and found that 0.2 μg of exoSTING, or an equivalent dose of free CDN, failed to induce systemic cytokines following IT injection. However, the efficacious dose of free CDN (20 μg) resulted in pronounced induction of serum inflammatory cytokines (IFN-β, TNF-α, and IL-6) (FIG. 14F-H). In addition, cytokine upregulation was observed in distal organs such as draining lymph nodes and spleen by high dose free CDN (20 μg) but not by low dose free CDN or exoSTING (data not shown). The lack of systemic inflammatory cytokine induction following an efficacious dose of exoSTING may reduce adverse events noted in early clinical testing with free CDNs while maximizing exposure in the TME (Corrales et al., *Cell Rep.* 11, 1018-1030 (2015); Meric-Bernstam et al., *J. Clin. Oncol.* 37(15_suppl), 2507 (2019)).

Figure 15A:
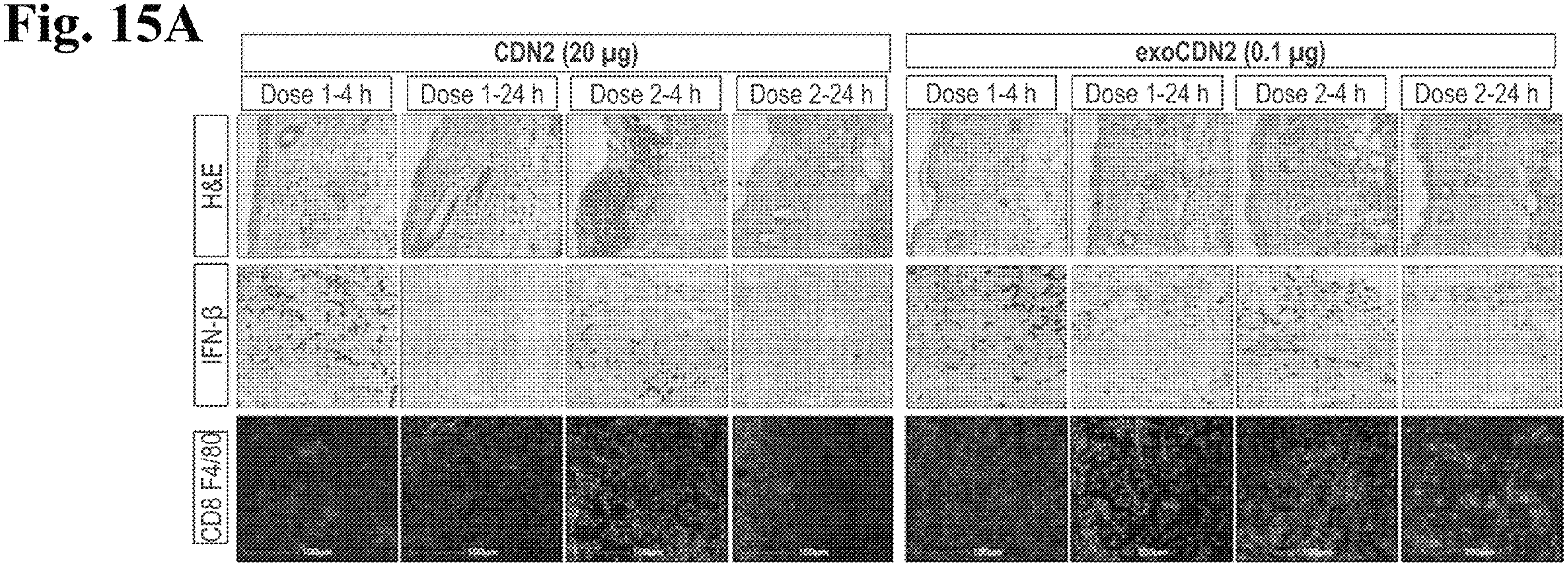
Figure 15B:
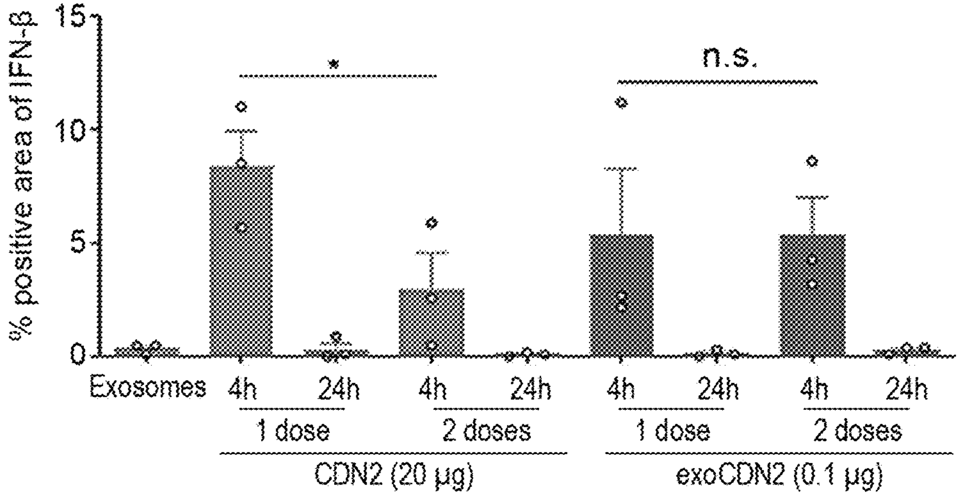

Example 10: exoSTING Preserves Immune Cell Viability and Enhances DC Activation and T Cell Recruitment In order to distinguish the immune stimulatory versus immune ablative mechanisms of action between free CDN2 and exoSTING, we compared the effects of efficacious doses of free CDN2 (20 μg) or exoSTING (0.1 μg) after IT dosing in a therapeutic setting with the B16F10 model. We histologically examined immune infiltration in injected B16F10 tumors four or 24 hours after one or two efficacious doses of free CDN2 compared to one or two efficacious doses of exoSTING. H&E staining of B16F10 tumors showed significant evidence of tissue damage in the skin and tumor cell death with free CDN2 treatment both 4 and 24 hours after two injections while there was limited tissue damage observed in exoSTING treated tissues (FIG. 15A, top row). At 4 hours after the first injection, free CDN and exoSTING induced comparable levels of IFN-β, and 24 hours after the second dose there was minimal IFN-β remaining (FIG. 15A, middle row and FIG. 15B) which is consistent with the tight regulation of IFN-β production following STING agonism. At 4 hours after the second injection, exoSTING induced comparable levels of IFN-β as the first injection, but lower induction was observed with free CDN, suggesting that the tissue damage induced by high dose free CDN impairs IFN-β production with a resultant reduction in immune cell infiltration (FIG. 15A, middle row and FIG. 15B). We observed that tumors treated with 20 μg of free CDN had significantly lower levels of T cell infiltration and numbers of $F4/80^+$ APCs than tumors treated with exoSTING (FIG. 15A, bottom row). Specifically, we observed that exoSTING treated tumors had a four-fold increase in the infiltration of $CD8^+$ T cells (FIG. 15C) than tumors treated with control non-CDN-loaded exosomes.

Figure 15D:
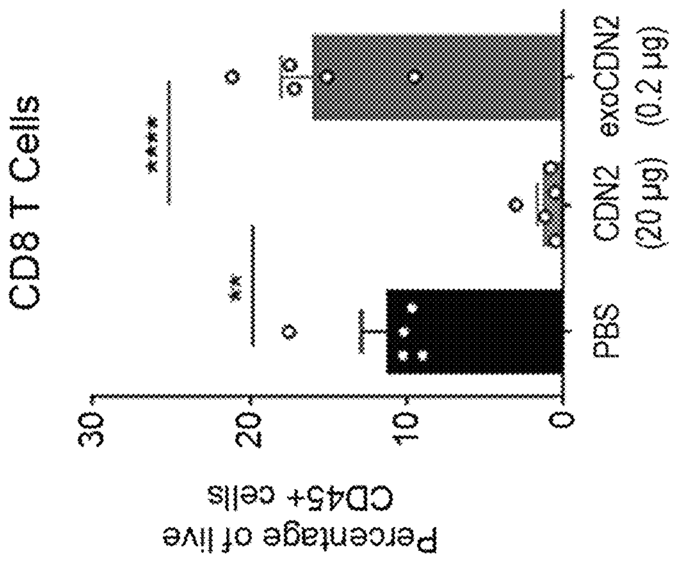
Figure 15C:
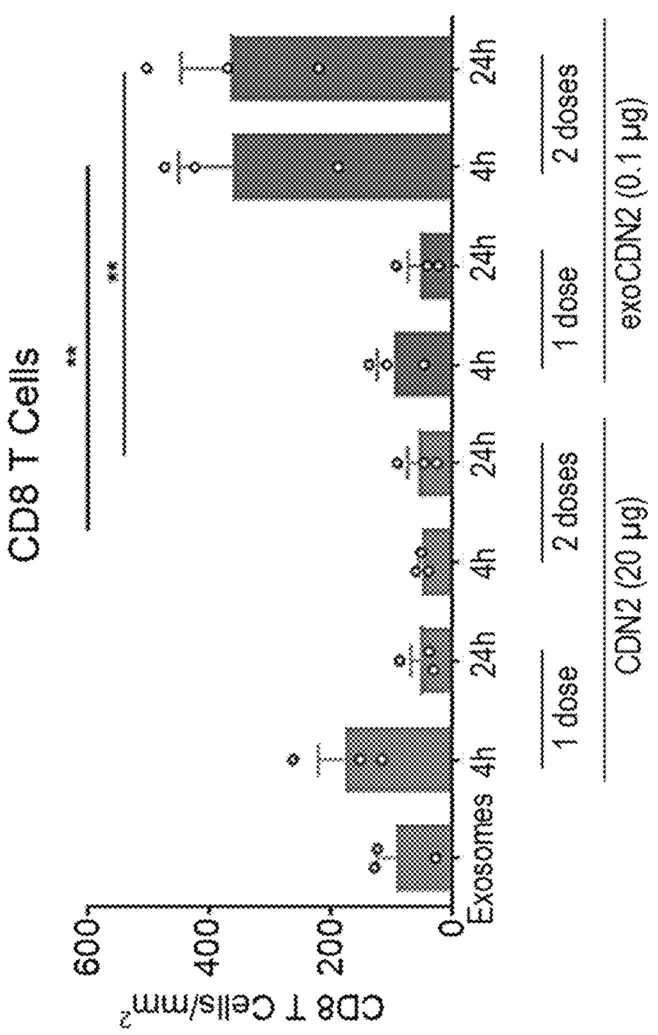
Figure 15E:
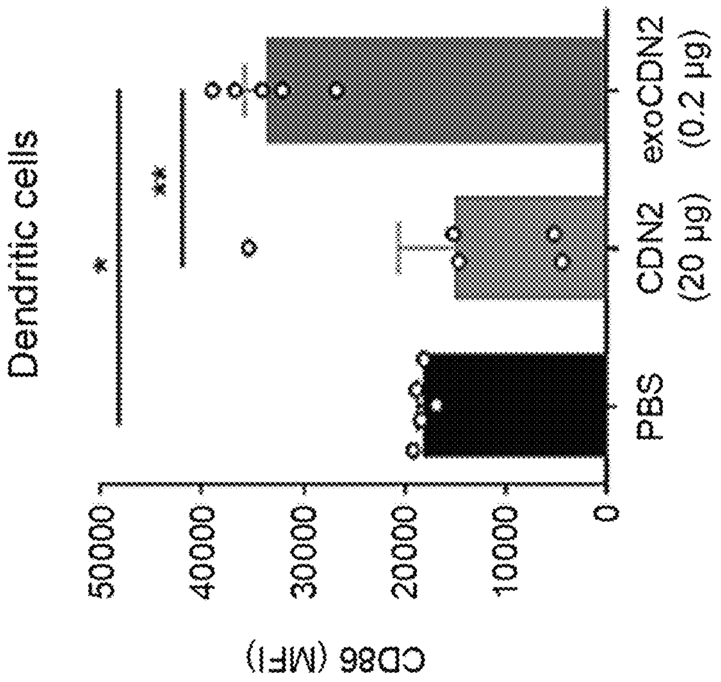

We also assessed $CD8^+$ T cell and $XCR1^+$ DC activation after two IT injections of exoSTING and free CDN2 by flow cytometry. Free CDN2 treatment at the high efficacious doses (20 μg) resulted in T cell ablation as the number of viable $CD8^+$ T cells was significantly decreased compared PBS control (FIG. 15D). In addition to $CD8^+$ T cells both F4/80 positive macrophages and DCs were also reduced by the 20 μg dose of free CDN2 (data not shown). In contrast, efficacious doses of exoSTING demonstrated a modest increase (>1.5 fold) in $CD8^+$ T cells over control treatment (FIG. 15D). This increase in $CD8^+$ T cell is consistent with the increased CXCL9 and CXCL10 production following exoSTING treatment (FIGS. 14D and 14E). ExoSTING treatment resulted in significant activation of $XCR1^+$ BATF3 lineage DCs as measured by CD86 expression, whereas free CDN did not activate these DCs (FIG. 15E). This DC population has been shown to be essential for establishing a systemic anti-tumor immune response (Corrales et al., J. Clin Invest 126, 2404-2411 (2016)). The enhanced activation of this DC subset seen with exoSTING but to a lesser degree with free CDN, is consistent with the observed superiority of anti-tumor activity of exoSTING in the B16F10 model (FIGS. 12 and 13). These data demonstrate the immune ablative effects of free CDN and highlight the improved immune stimulatory effects of exoSTING.

Figure 16A:
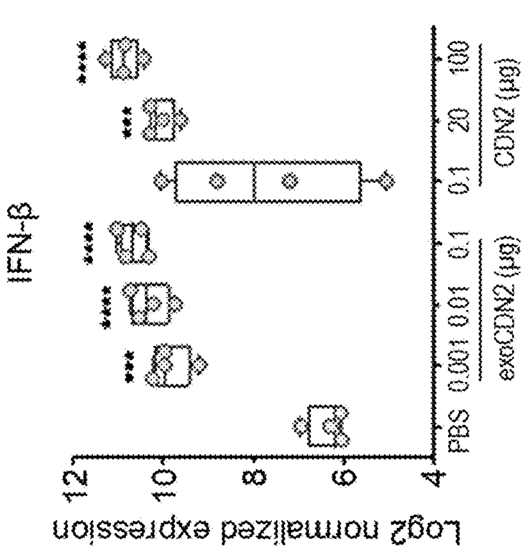
Figure 16B:
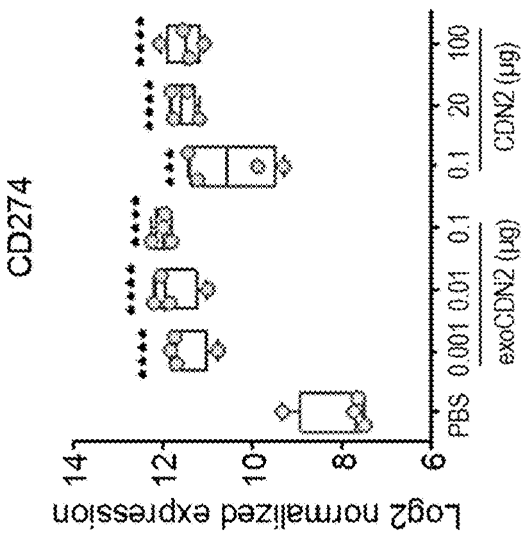
Figure 16C:
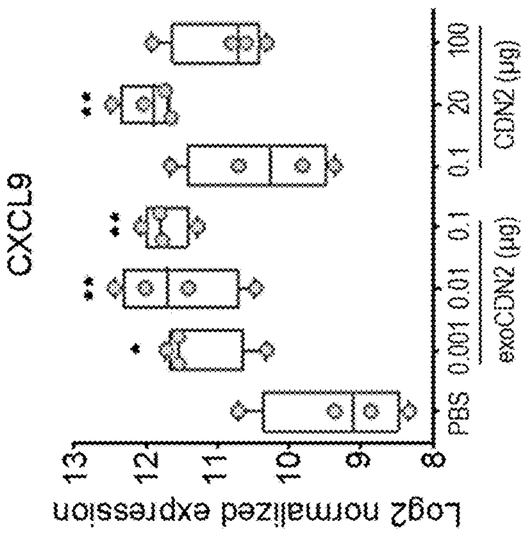

Example 11: Differential Gene Expression Studies Confirm Potent Immune Stimulation by exoSTING We evaluated the expression of immune related genes in the TME that are immediately altered (4 hours) after IT injection with increasing doses of exoSTING (0.001, 0.01, and 0.1 μg) and free CDN2 (0.1, 20, and 100 μg) by NanoString analysis. The immediate target gene for STING pathway activation, IFN-β, is induced in a dose-dependent manner by both exoSTING and free CDN (FIG. 16A). Very low doses of exoSTING (0.001 μg) upregulated IFN-β mRNA by 8-fold compared to PBS treatment. In contrast, a 100-fold higher dose of free CDN (0.1 μg) did not induce IFN-β to a similar extent, demonstrating the improved potency of exoSTING. Similar improvements in potency were also observed in the levels of CD274 (PD-L1), a key IFN-γ-regulated gene (FIG. 16B). This data is consistent with the anti-tumor activity observed with exoSTING at these low doses (0.001 ug; FIG. 12E). Expression of CXCL9 increased with exoSTING treatment (FIG. 12C). In contrast, free CDN treatment demonstrated a bell-shaped dose response for CXCL9. Peak expression was observed at the 20 μg free CDN dose while the higher dose of 100 μg that was required for distal non-injected tumor control (FIG. 13D) and led to immune ablation (FIG. 13E) resulted in decreased CXCL9 production (FIG. 16C).

Figure 16E:
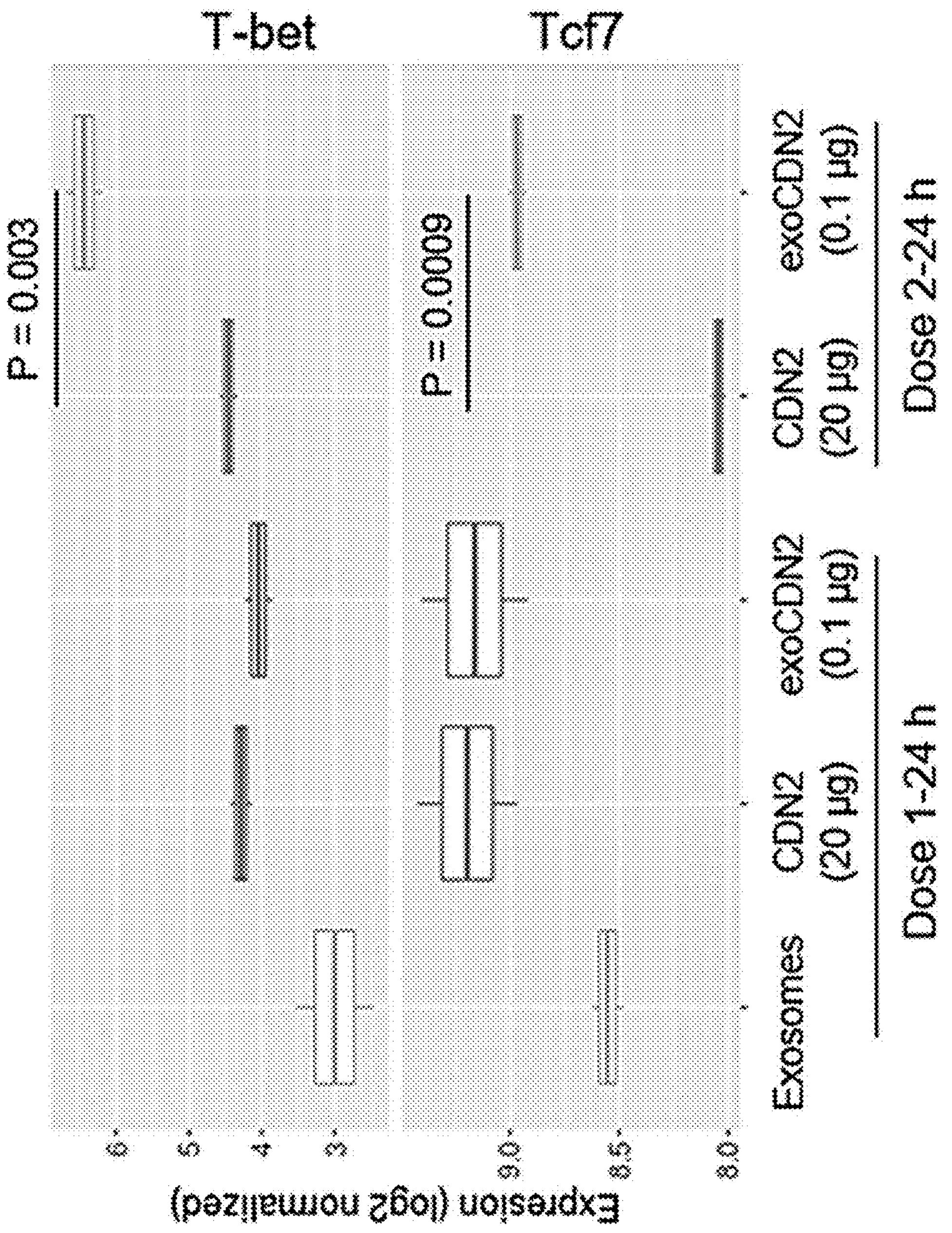

To further characterize the immune pathway activation, we evaluated the global gene expression changes after 1 or 2 IT injections of efficacious doses of exoSTING (0.1 μg) and free CDN2 (20 μg) by RNA sequencing. All samples were compared to PBS treatment. Expression profiles after IT injection of exosomes not loaded with CDN were not significantly changed demonstrating that empty exosomes do not elicit significant global gene expression changes (FIG. 16D). Genes belonging to Th1 activation pathways were enriched only in exoSTING treated tumors, but not in free CDN treated tumors (FIG. 16D), confirming the immune ablative effects of free CDN. T-bet (Tbx21), an immune cell transcription factor originally described as the master regulator of Th1 cell development (see Szabo et al., *Cell* 100, 655-669 (2000)), was significantly upregulated (adjusted p-value<0.005) by exoSTING compared to free CDN after 2 doses (FIG. 16E). Tcf7 (which encodes TCF1) is a key transcription factor expressed in the stem-like progenitor $CD8^+$ T cells (Siddiqui et al., Immunity. 50, 195-211.e10 (2019)). This cell subset is required for response to checkpoint inhibitor therapies. (Siddiqui, 2019). Free CDN2 treatment after 2 does resulted in a significant (adjusted p-value<0.001) decrease in Tcf7 levels, suggesting a loss of this key subset of T cells. This loss may underlie the lack of immunological memory response to free CDN. In contrast, exoSTING treatment resulted in the upregulation of the T-bet and sustained expression of Tcf7 demonstrating potent Th1 reprogramming.

Figure 16G:
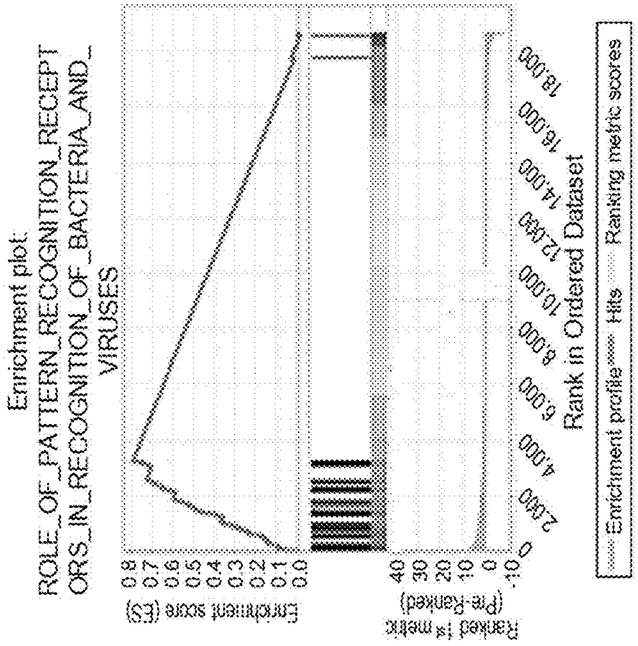
Figure 16F:
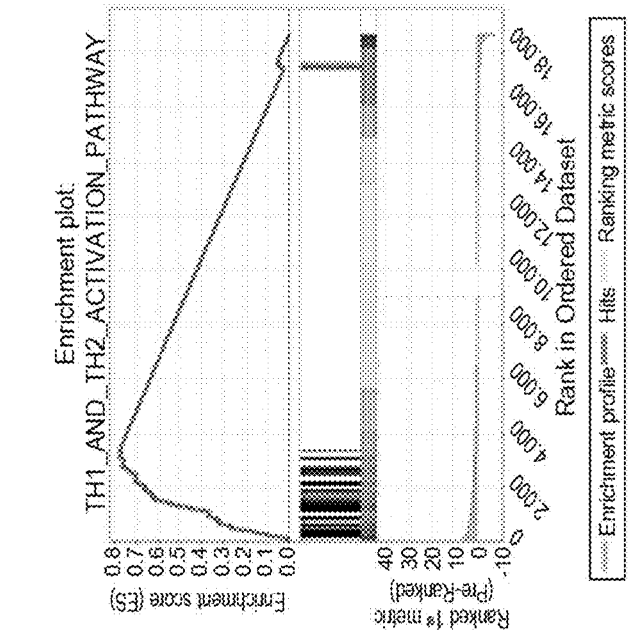
Figure 16H:
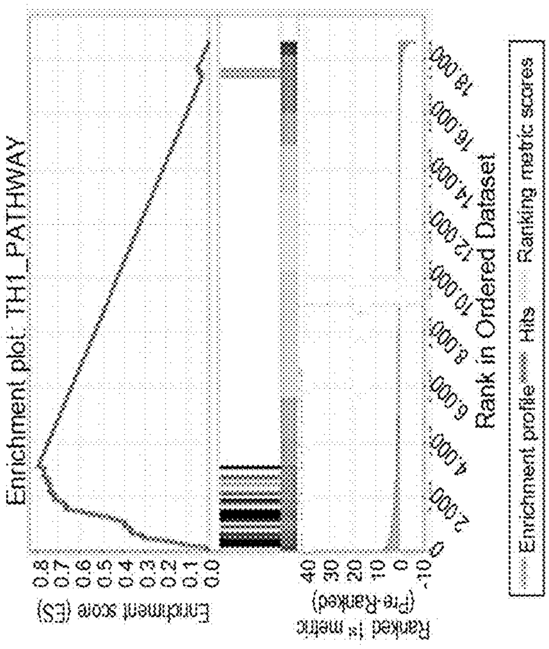

Gene Set Enrichment Analysis (GSEA) showed that genes involved in pattern recognition receptors in recognition of bacteria and viruses were upregulated by 1 dose of both exoSTING and free CDN (FIG. 16D) to a similar degree. However, those genes were further upregulated by exoSTING, but decreased by free CDN after the $2^{nd}$ dose. ExoSTING-treated tumors (after 2 doses) were significantly enriched in "Th1 and Th2 activation pathway" (adjusted p-value<1e-12), "Role of pattern recognition receptors in recognition of bacteria and viruses" (adjusted p-value<1e-12), and "Th1 pathway" (adjusted p-value<1e-12) transcripts FIG. 16F-H). This data supports the potency improvement and immune stimulatory effects of exoSTING compared to free CDN. Collectively, these data suggest that exoSTING activates differential pathways at lower doses than free CDN, and results in activation of IFN-γ and downstream chemokines CXCL9 and CXCL10 involved in T cell recruitment. In contrast, high doses of free CDN decrease the expression of these key genes as well as reducing the expression of APC markers.

Example 12: exoSTING Preferentially Activates STING Pathway in APCs In Vitro

We assessed uptake of exosome across immune cell subtypes using $PTGFRN^{+/+}$ exosomes engineered to express luminal GFP. Analysis of cellular uptake and association with GFP containing exosomes in PBMCs revealed a dose dependent increase in $PTGFRN^{+/+}$ exosomes association with monocytes (40-fold over baseline at highest dose), dendritic cells (cDC=4-fold, pDC=2-fold), and T cells (2-fold) (data not shown). The GFP uptake in NK cells (1.5-fold) and B cells (0.8-fold) was close to the background control levels demonstrating a preferential association of exosomes with APCs. To assess the distinct immune cell subsets activated by free CDN or exoSTING, we evaluated immune cell activation markers by flow cytometry with purified immune cells from PBMCs. CD86 expression was assessed as a cell activation marker for monocytes, whereas CD69 was used as an activation marker for T cells, NK cells, and B cells. ExoSTING treatment resulted in a dose dependent activation of monocytes with an $EC_{50}$ of ~0.001 μM, but no activation of purified B cells, T cells, and NK cells was observed at the maximal concentrations evaluated (FIG. 17A). In contrast, free CDN activated not only monocytes ($EC_{50}$ 0.06 μM), but at higher drug concentrations required for anti-tumor activity also activated T cells ($EC_{50}$~3.6 μM) and NK cells ($EC_{50}$~2.4 μM) (FIG. 17B). These data suggest that exoSTING preferentially taken up by monocytes and activate them.

Macrophages as well as DCs represent an important class of APC in the TME. Many human tumors have been reported to be enriched in M2 immunosuppressive macrophages (Ugel et al., J Clin. Invest. 125, 3365-3376 (2015)). Both DCs and Macrophages play an important role in STING agonist mediated anti-tumor immunity (Ohkuri et al., Hum. Vaccin. Immunother. 14, 285-287 (2018)). To assess the effect of exoSTING on human APCs, we compared the potency of exoSTING and free CDN on DCs, M1 or M2 polarized macrophages as assessed by IFN-β production. ExoSTING induced IFN-β production at an $EC_{50}$~2.9 nM in purified human DCs compared to 222 nM with free CDN (FIG. 17C). In addition, exoSTING induced IFN-β production at an $EC_{50}$~0.05 μM in M2 polarized macrophages compared to 2.4 μM with free CDN (FIG. 17D). In contrast, exoSTING failed to induce IFN-β production at all doses tested in M1 polarized macrophages (FIG. 17E). The preferential activation of DCs and M2 macrophages by exoSTING may at least in part be associated with more efficient delivery of CDN to DCs and M2 macrophages. M2 polarized macrophages show ~5-fold greater uptake of exosomes compared to M1 polarized macrophages (data not shown). Phagocytosis alone does not account for the uptake of exosomes by M2 macrophages as the phagocytosis inhibitor Cytochalasin D does not completely block exosome uptake or IFNβ production from M2 polarized human macrophages (data not shown).

Next, we characterized the effect of exoSTING for free CDN on naïve or TCR stimulated T cells. We purified T cells and treated them with a dose titration of exoSTING or free CDN and compared IFNβ production in the presence or absence of TCR stimulation. At the higher dose levels, free CDN2-induced IFN-β production at an $EC_{50}$~8.2 μM (FIG. 17F) in T cells stimulated by anti-CD3 and anti-CD28, but no IFN-β production was observed in the naïve T cells (data not shown). In contrast, exoSTING did not induce IFN-β production at any dose tested from both naïve and anti-CD3 and anti-CD28 stimulated T cells (FIG. 17F). We next characterized induction of T cell death using Cytotox dye staining following exoSTING or free CDN2 treatment in T cells stimulated with anti-CD3 and anti-CD28. Following free CDN2 treatment, we observed a dose dependent increase in T cell death (up to ~20% of T cells) as measured by Cytotox dye staining (FIG. 17G). No dose dependent increase in the T cell death was observed at any dose levels tested with exoSTING. These results demonstrate that exoSTING can preferentially activate M2 macrophages with a significantly improved potency as compared to free CDN2 and does not induce activation of other immune cells. Importantly, exoSTING preserves the viability of TCR stimulated T cells.

We have previously identified and characterized exosome-specific surface glycoproteins using unbiased proteomic analysis and identified the immunoglobulin super family member PTGFRN as a protein that is enriched on human exosomes and contains nine predicted N-linked glycosylation sites (see Dooley et al., Cancer Res. 79(13 Suppl), Abstract nr 2150 (2019), which is incorporated by reference herein in its entirety). DCs and macrophages are known to express several carbohydrate receptors on their surface, and exosomes, via the surface glycoproteins, have been shown to bind to these sialic acid glycoprotein receptors such as Siglec-9 to facilitate internalization (Dusoswa et al., *J. Extracell. Vesicles* 8, 1648995 (2019), which is incorporated by reference herein in its entirety). To understand the contribution of PTGFRN on activation of immune cells, exosomes were engineered to express high levels of $PTGFRN^{+/+}$, normal levels of PTGFRN (WT), or PTGFRN null exosomes ($PTGFRN^{-/-}$) were produced in HEK293SF cells as described previously (Dooley, et al., *Cancer Res.* 79(13 Suppl), Abstract nr 2150, 2019, which is incorporated by reference herein in its entirety). All exosome populations were approximately 50-200 nm in size (data not shown). These populations of exosomes were next examined for their capacity activate STING pathway as measured by IFN-β production. WT, $PTGFRN^{+/+}$, or $PTGFRN^{-/-}$ exosomes were loaded with CDN1 (data not shown). These CDN-loaded exosomes were assayed in vitro for their potential to induce IFN-β production in PBMC cultures. $EC_{50}$ values and maximal IFN-β cytokine production ($C_{max}$) were assessed from multiple donors. As compared to the free CDN, the exosome-loaded CDN significantly enhanced potency. IFN-β $C_{max}$ was greatest in the $PTGFRN^{+/+}$ exosomes (mean 133-fold induction of IFN-β over background, n=4) compared to the WT (mean 59-fold induction) and $PTGFRN^{-/-}$ exosomes (mean 29-fold induction) with progressively lower $C_{max}$ levels of IFN-β correlating with the levels of exosomal PTGFRN (FIG. 17H). In addition, we compared the in vivo activity of different exosomes (WT, $PTGFRN^{-/-}$ and $PTGFRN^{+/+}$) loaded with equal amounts of CDN in the B16F10 tumor model. We observed that anti-tumor activity was correlated with exosomal PTGFRN density with $PTGFRN^{-/-}$ exosomes having minimal anti-tumor activity (FIG. 17I). Although the precise role of PTGFRN in mediating exoSTING potency is yet to be delineated, these data suggest that glycoprotein PTGFRN on exosomes may plays on a role on maximal activation of immune cells and in vivo anti-tumor activity, which may be contributed by cellular tropism and immune cell signaling activity of PTGFRN (Luan et al., *Acta Pharmacol. Sin.* 38, 754-763 (2017); Dusoswa et al., *J. Extracell. Vesicles* 8, 1648995 (2019), which is incorporated by reference herein in its entirety).

Example 13: Preferential Activation of APCs by exoSTING In Vivo

To explore whether exoSTING and the preferential activation observed in vitro would have an impact on these observed actions of free CDN, we implemented a micro-dosing IT injection study using the CIVO (Comparative In Vivo Oncology) Platform paired with multiplexed immunofluorescence-based histology analysis to compare the effects of these therapeutic approaches simultaneously in a single tumor. CIVO allows for a single tumor to be injected with multiple microdose treatments to enable comparisons of the effects of different analytes in a single mouse tumor (Klinghoffer et al., *Sci. Transl. Med.* 7, 284ra56 (2015)). The A20 subcutaneous B cell lymphoma model was selected to evaluate the selective uptake of exosomes and cell activation parameters by histological examination of the tumors. B cells are a good surrogate to assess the "off-target" activity of pleiotropic STING activation as these cells undergo apoptosis (Tang et al. *Cancer Res.,* 2137-2152 (2016)). A20 tumors were injected with exoSTING (0.02 μg CDN), 0.02 μg or 2 μg of free CDN, and empty exosomes not loaded with CDN as a control. Four hours after dosing, we found that 2 μg CDN treatment resulted in widespread phosphorylation of TBK1 (pTBK1) in CD19 positive B cells as well as APCs suggesting uptake of the CDN and broad activation of the STING pathway in both tumor and immune cells, whereas 0.02 μg exoSTING induced pTBK1 expression selectively in subset of immune cells that are CD19 negative (FIG. 18A, top row). Despite broad activation of pTBK1 with 2 μg of free CDN, only modest induction of IFN-β was observed (FIGS. 14A and 14B). Most of IFN-β production correlated with F4/80 in the exoSTING-treated tumors, whereas IFN-β production was observed in both F4/80 positive and F4/80 negative cells in free CDN (2 μg)-treated tumors (FIG. 18D). Free CDN at a dose of 2 μg resulted in dramatic histologic changes in the injected tumor, characterized by areas of apoptotic cells around the injection site (apoptotic scars). These apoptotic scars were associated with high levels of cleaved caspase 3 (CC3). ExoSTING showed markedly less pTBK1 induction and CC3 around the injection site following injection (FIG. 18A, bottom row and FIG. 18C). Together, these data demonstrate that IT injections of high dose free CDN (which are required for anti-tumor effects in preclinical models) induced widespread STING activation, induction of pTBK1 and apoptotic cell death. In contrast, exoSTING induces preferential activation of the STING pathway in $F4/80^{+}$ APCs and dramatically reduces generalized apoptosis and tissue damage.

Example 14: Preferential Activation of APCs by exoSTING In Vivo

A clinical study will be conducted to test the safety and efficacy of treating a cancer in a human subject by administering engineered exosomes expressing PTGFRN and containing a STING agonist (exoSTING) (FIG. 19). In part A, healthy volunteers will be administered varying doses of exoSTING and monitored of adverse events and biomarkers. In part B, subjects diagnosed with HNSCC will be administered various doses of exoSTING and monitored for safety and biomarkers (FIG. 20). Clinical activity will be monitored by one or more CT scan. Subjects having TNBC, sCSS, and ATC will be eligible for part B of the trial. Additional indications for part B include leptomeningeal cancer or glioblastoma.

Example 15: Analysis of Biodistribution, Pharmacodynamics, and Anti-Tumor Activity of exoSTING First, to evaluate the biodistribution of exosomes after intravenous (IV) administration, $^{89}$Zr-DFO labeled exosomes were injected intravenously into mice and radioactivity was visualized in the animals with PET/CT. To quantify the distribution data from the PET/CT scan, % of the injected exosome dose was measured in different tissues. As shown in FIGS. 21A and 21B, after intravenous administration, majority of the administered exosomes were found in the liver (67% of the injected dose) and partly in the spleen (3% of injected dose).

Next, to assess the pharmacodynamic impact of STING activation after IV administration, animals were treated with one of the following: (i) exosome not loaded with any CDN; (ii) free CDN2 (0.2 μg); and (iii) exosomes loaded with STING agonist (0.2 μg). Then, at four hours post-injection, the mRNA levels of IFN-β, CXCL9, and CXCL10 were assessed in the liver. As shown in FIG. 22A, ExoSTING treatment induced approximately 10,000-fold higher levels of IFN-β in the liver compared to equivalent doses of free CDN (FIG. 22A). ExoSTING also induced substantially higher levels of CXCL9 (200-fold vs free CDN) and CXCL10 (500-fold vs free CDN) mRNA than a comparable amount of free CDN (FIGS. 22B and 22C).

Additionally, to assess anti-tumor activity of exoSTING after IV administration, a Hepa1-6 orthotopic hepatocellular carcinoma model (reference) was used. Hepa1-6 cells were injected into spleens to induce tumor development in the liver. Upon tumor establishment the animals were injected intravenously at day 4, 7, and 10 with one of the following: (i) exosomes not loaded with any CDN, (ii) free CDN (0.2 μg), and (iii) exoSTING (0.2 μg). Then, the animals were sacrificed at day 15 post-tumor induction, and anti-tumor response was assessed in the liver.

ExoSTING treatment resulted in 3 complete remission (CR) and 1 partial response (PR) out of 8 mice, which was assessed by liver weight/body weight ratio (FIG. 23A) and % lesions score (FIG. 23B). In contrast, no response was observed with the equivalent amount of free CDN. Representative images showed that exoSTING treated liver was similar with sham control without signs of tumors, whereas evident tumor growth was observed in exosomes and free CDN treated liver (FIG. 23C). In addition, there was no apparent change in liver enzymes, ALT and AST, in a serum (FIGS. 24A and 24B).

Collectively, these data demonstrated superior activation of STING pathway in the liver and anti-tumor activity in a hepatocellular carcinoma by exoSTING.

It is to be appreciated that the Detailed Description section, and not the Summary and Abstract sections, is intended to be used to interpret the claims. The Summary and Abstract sections can set forth one or more but not all exemplary aspects of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary aspects, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, can need to be revisited. Further, the Examiner is also reminded that any disclaimer made in the instant application should not be read into or against the parent application.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific aspects have been illustrated and described, the above specification is not restrictive. It will be appreciated that various changes can be made without departing from the spirit and scope of the disclosure(s).

The invention claimed is:

1. A method of preparing a composition comprising extracellular vesicles (EVs) associated with one or more cyclic dinucleotides (CDNs), comprising incubating the EVs with a loading concentration of cyclic dinucleotides (CDNs) in a mixture, wherein, after the incubation, the composition comprises EVs with loaded CDNs and free CDNs and wherein the free CDNs are removed by a multimodal chromatography.

2. The method of claim 1, wherein:

(i) the composition after the chromatography comprises CDNs at a final concentration between 1 μM and 10 μM;

(ii) the loading concentration of the CDNs is at least 500 μM;

(iii) after the multimodal chromatography, the percentage of free CDNs present in the composition is less than about 90 percent;

(iv) a loading concentration of the EVs is at least $2\times10^{12}$ particles/mL;

(v) the loading concentration of CDNs is between 0.9 mM and 1.1 mM;

(vi) after the incubation, the percentage of EVs loaded with a CDN is about 99%; or (vii) any combination of (i)-(vi).

3. A method of improving potency of cyclic dinucleotides (CDNs) in association with an EV, comprising:

incubating the EV with the CDNs at a loading concentration of at least about 0.5 mM in a composition, wherein the composition, after the incubation, comprises the EVs with loaded CDNs and free CDNs, and removing the free CDNs from the EVs, wherein after the separation, the loaded CDNs are at a concentration between about 0.5 μM and about 10 μM, wherein the free CDNs are separated from the EVs by a multimodal chromatography.

4. The method of claim 3, wherein:

(i) the loading concentration of CDNs is between about 700 UM and about 2 mM;

(ii) the final concentration after the chromatography is between about 2 μM and about 10 μM;

(iii) a loading concentration of the EVs is at least $2\times10^{12}$ particles/mL;

(iv) the loading concentration of CDNs is between 0.9 mM and 1.1 mM;

(v) after the incubation, the percentage of EVs loaded with a CDN is about 99%; or (vi) any combination of (i) to (v).

5. The method of claim 1, wherein the multimodal chromatography is a CaptoCore 700, Capto MMC, or Capto MMC ImpRes.

6. The method of claim 3, wherein the multimodal chromatography is a CaptoCore 700, Capto MMC, or Capto MMC ImpRes.

7. The method of claim 1, wherein the removing the free CDNs is at a pH lower than 7.6 in a multimodal chromatography.

8. The method of claim 2, wherein the removing the free CDNs is at a pH lower than about 7.5.

9. The method of claim 3, wherein the removing the free CDNs is at a pH lower than about 7.5.

10. The method of claim 8, wherein the pH is about 6.8.

11. The method of claim 1, wherein the EV comprises a scaffold protein.

12. The method of claim 11, wherein the scaffold protein is a prostaglandin F2 receptor negative regulator (PTGFRN) protein or a fragment thereof.

13. The method of claim 11, wherein the scaffold protein is not associated with the one or more CDNs.

14. The method of claim 1, wherein the EVs are exosomes.

15. The method of claim 1, wherein the cyclic dinucleotide (CDN) is a STING agonist.

16. The method of claim 1, wherein the EVs overexpress a PTGFRN protein.

17. The method of claim 15, wherein the STING agonist comprises:

Formula 1

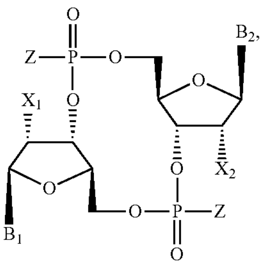

or

-continued

Formula 2

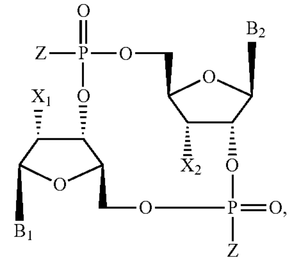

wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is pivaloyloxymethyl;

B1 and B2 are bases chosen from:

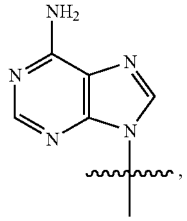

Adenine

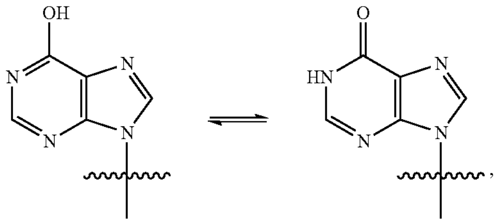

or

Hypoxanthine

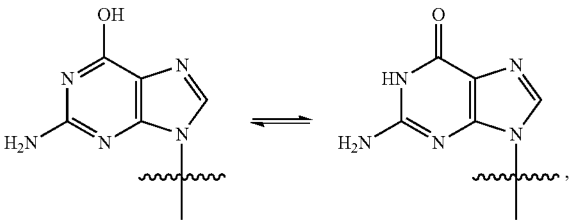

Guanine

With the proviso that:

in Formula (I): $X_1$ and $X_2$ are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH, or a pharmaceutically acceptable salt thereof.

18. The method of claim 17, wherein the STING agonist is selected from the group consisting of:

-continued
CL606
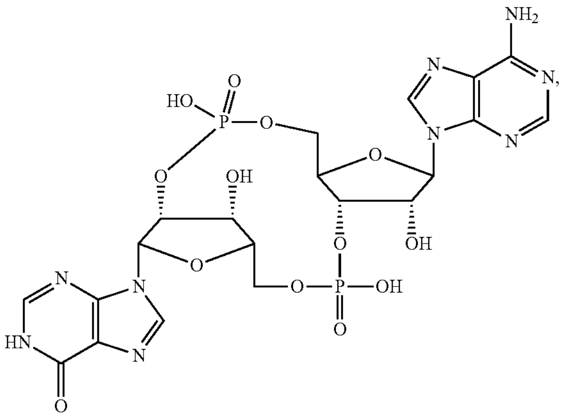
(3′,2′)c-AIMP
CL611
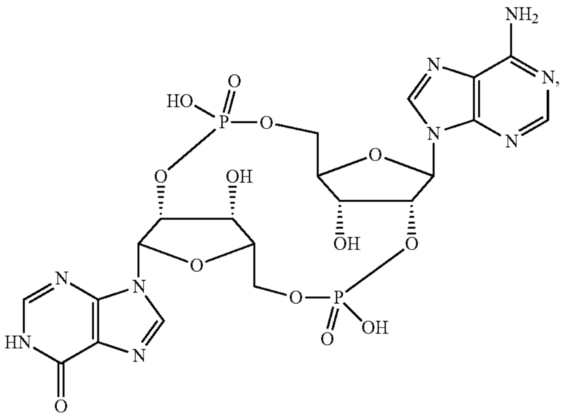
(2′,2′)c-AIMP
CL602
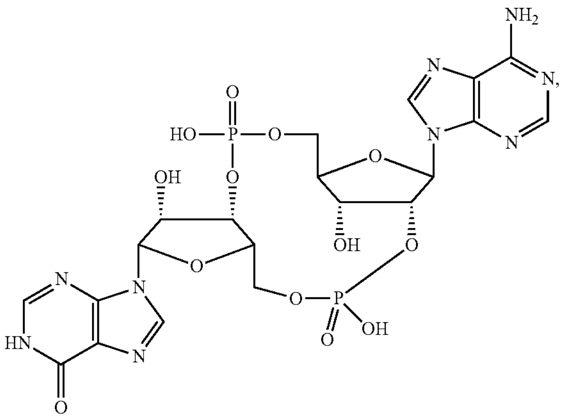
(2′,3′)c-AIMP
CL655
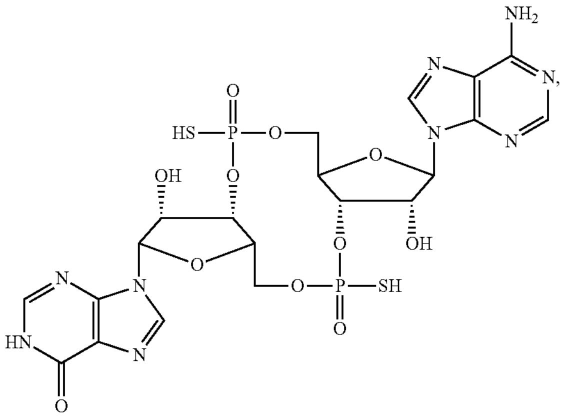
c-AIMP(S)
CL604
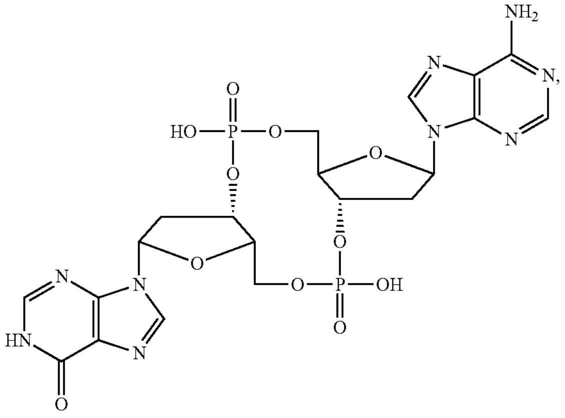
c-(dAMP-dIMP)
CL609
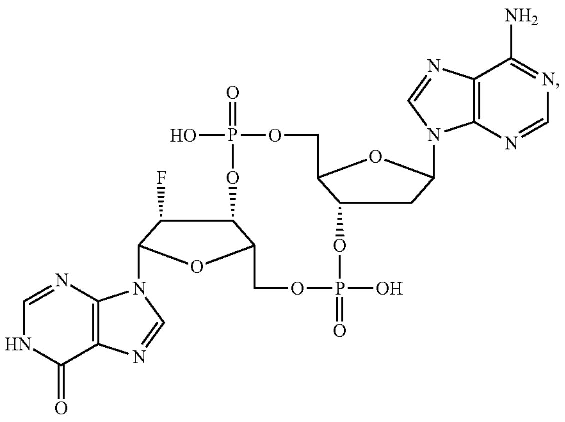
c-(dAMP-2′FdIMP)

-continued
CL614
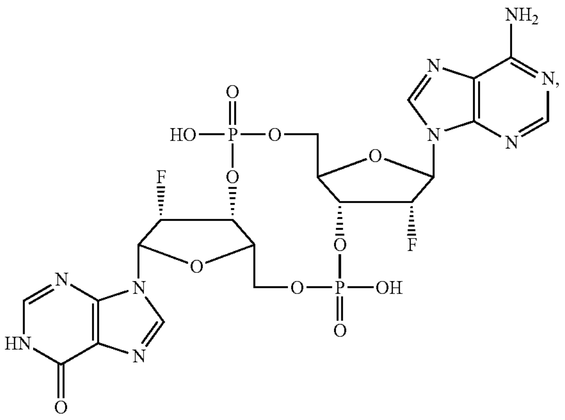
c-(2-FdAMP-2′FdIMP)
CL656
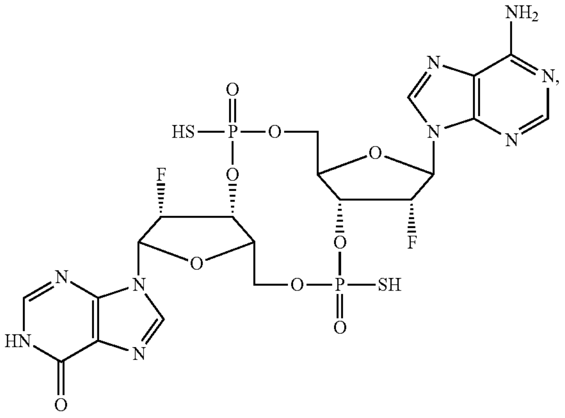
c-[2′-FdAMP(S)-2′FdIMP(S)]
CL647
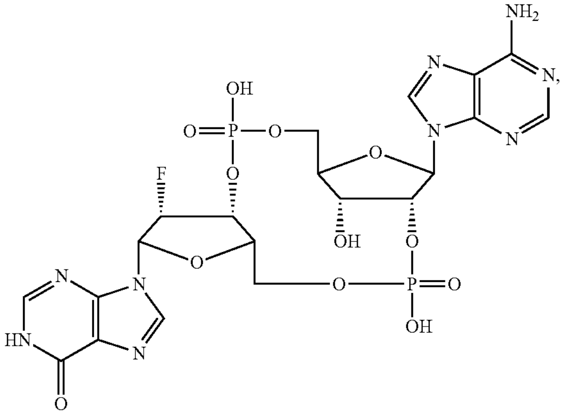
(2′,3′)c-(AMP-2′FdIMP)
-continued
CL626
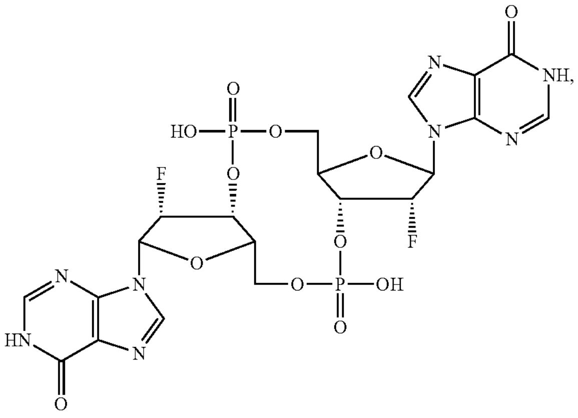
c-di(2′-FdIMP)
CL629
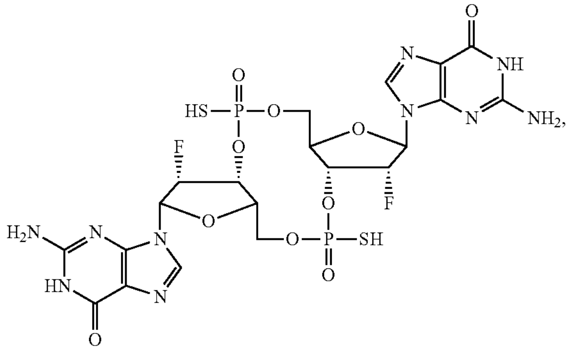
c-di(2′-FdGMP)
CL603
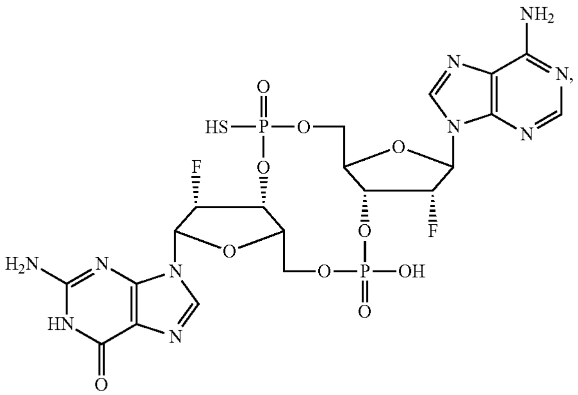
c-(2′-FdGMP-2′FdAMP)

-continued

CL632

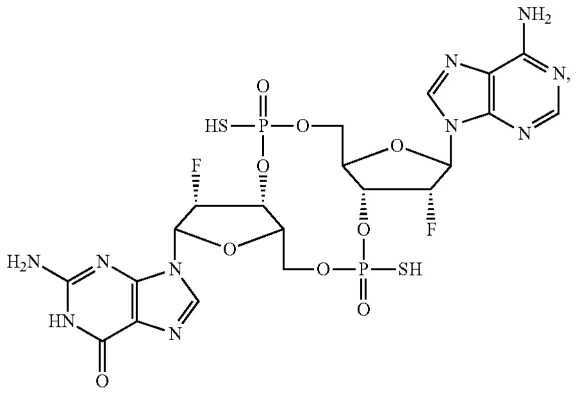

c-[2'FdGMP(S)-2'FdAMP(S)]

CL633

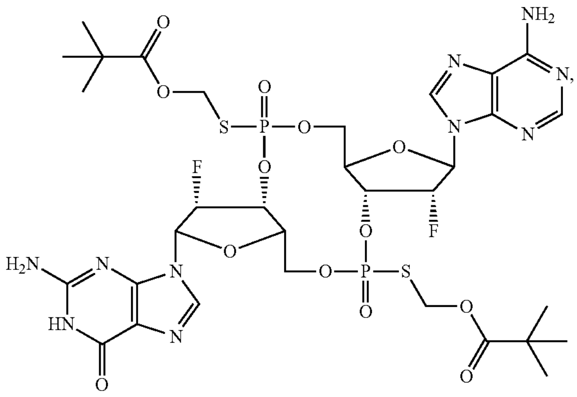

c-[2'FdGMP(S)-2'FdAMP(S)](POM)2

-continued

CL659

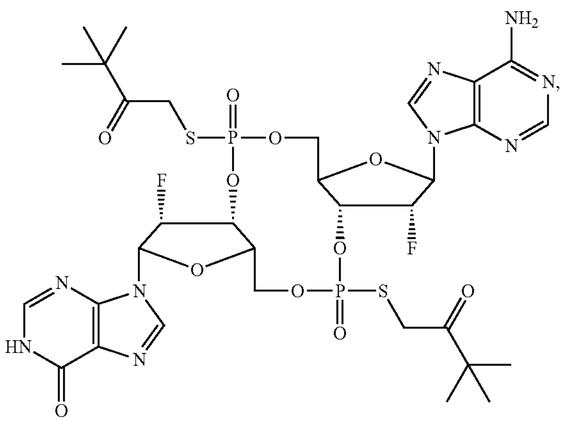

c-[2'FdGMP(S)-2'FdIMP(S)](POM)2

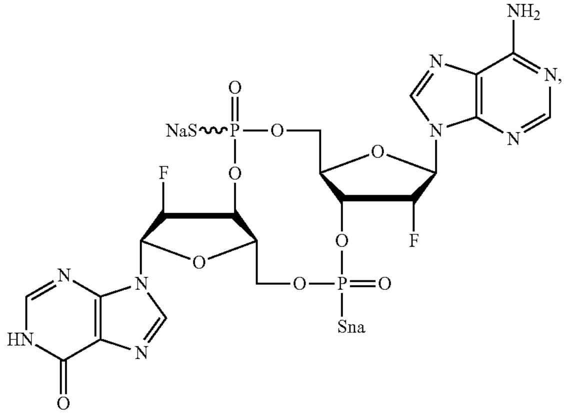

and a pharmaceutically acceptable salt thereof.

19. The method of claim 1, wherein the EVs are formulated in a pharmaceutical composition, comprising:

(i) at least 1 μM of CDNs;

(ii) a monosaccharide, a disaccharide, a trisaccharide, an oligosaccharide, a polysaccharide, a sugar alcohol, or any combination thereof;

(iii) sodium chloride;

(iv) phosphate-buffered saline, phosphate, citrate, formate, acetate, or Tris (hydroxymethyl)-aminomethane ("Tris") buffer;

(v) an anti-oxidant; or (vi) any combination of (i) to (v).

* * * * *